(12) United States Patent
Lipford et al.

(10) Patent No.: US 9,353,115 B2
(45) Date of Patent: May 31, 2016

(54) IMMUNE SYSTEM MODULATORS

(75) Inventors: Grayson B. Lipford, Watertown, MA (US); Charles M. Zepp, Hardwick, MA (US)

(73) Assignee: JANUS BIOTHERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 14/122,435

(22) PCT Filed: Jun. 1, 2012

(86) PCT No.: PCT/US2012/040425
§ 371 (c)(1),
(2), (4) Date: Nov. 26, 2013

(87) PCT Pub. No.: WO2012/167053
PCT Pub. Date: Dec. 6, 2012

(65) Prior Publication Data
US 2014/0107115 A1   Apr. 17, 2014

Related U.S. Application Data

(60) Provisional application No. 61/491,966, filed on Jun. 1, 2011.

(51) Int. Cl.
| C07D 473/40 | (2006.01) |
| C07D 473/38 | (2006.01) |
| C07D 473/34 | (2006.01) |
| C07D 473/32 | (2006.01) |
| C07D 473/30 | (2006.01) |
| C07D 473/24 | (2006.01) |

(52) U.S. Cl.
CPC ............ *C07D 473/34* (2013.01); *C07D 473/24* (2013.01); *C07D 473/30* (2013.01); *C07D 473/32* (2013.01); *C07D 473/38* (2013.01); *C07D 473/40* (2013.01)

(58) Field of Classification Search
CPC .. C07D 473/30; C07D 473/34; C07D 473/24; C07D 473/32; C07D 473/40; C07D 473/38
See application file for complete search history.

(56) References Cited

U.S. PATENT DOCUMENTS

| 3,854,480 | A |   | 12/1974 | Zaffaroni |  |
| 4,452,775 | A |   | 6/1984  | Kent |  |
| 4,675,189 | A |   | 6/1987  | Kent et al. |  |
| 4,728,644 | A | * | 3/1988  | Yuki et al. ............... 514/218 |
| 5,075,109 | A |   | 12/1991 | Tice et al. |  |
| 5,133,974 | A |   | 7/1992  | Paradissis et al. |  |
| 5,407,686 | A |   | 4/1995  | Patel et al. |  |
| 5,491,084 | A |   | 2/1996  | Chalfie et al. |  |
| 5,602,140 | A | * | 2/1997  | Isobe et al. ............. 514/263.3 |
| 5,736,152 | A |   | 4/1998  | Dunn |  |
| 6,194,388 | B1 |   | 2/2001 | Krieg et al. |  |
| 6,207,646 | B1 |   | 3/2001 | Krieg et al. |  |
| 6,218,371 | B1 |   | 4/2001 | Krieg et al. |  |
| 6,239,116 | B1 |   | 5/2001 | Krieg et al. |  |
| 6,486,382 | B1 |   | 11/2002 | Gordan-Kamm et al. |  |
| 6,743,798 | B1 |   | 6/2004 | Straub et al. |  |
| 2003/0148976 | A1 |   | 8/2003 | Krieg et al. |  |
| 2005/0227933 | A1 | * | 10/2005 | Benkovic ................ C07F 5/025 514/44 R |
| 2010/0210598 | A1 |   | 8/2010 | Carson et al. |  |

FOREIGN PATENT DOCUMENTS

| EP | 0286425 A2     | 10/1988 |
| WO | WO-9837919 A1  | 9/1998  |
| WO | WO-9840100 A1  | 9/1998  |
| WO | WO-9850547 A2  | 11/1998 |
| WO | WO-9852581 A1  | 11/1998 |
| WO | WO-9956755 A1  | 11/1999 |
| WO | WO-0006569 A1  | 2/2000  |
| WO | WO-0109134 A1  | 2/2001  |
| WO | WO-0122990 A2  | 4/2001  |
| WO | WO-0149688 A1  | 7/2001  |
| WO | WO-0190151 A2  | 11/2001 |
| WO | WO-2010059401 A2 | 5/2010 |

OTHER PUBLICATIONS

Marumoto et al., Chem. Pharm. Bull. 27(4) 990-1003(1979).*
Examination Report issued by the Australian Patent Office in Australian Patent Application No. 2012262021 dated Sep. 24, 2015 (12 pgs.).
Adachi, et al., "Targeted Disruption of the MyD88 Gene Results in Loss of IL-1- and IL-18-mediated Function," Immunity, vol. 9, pp. 143-150 (1998).
Aderem, et al., "Toll-like Receptors in the Induction of the Innate Immune Response," Nature, vol. 406, pp. 782-787 (2000).
Alexopoulou, et al., "Recognition of Double-stranded RNA and Activation of NF-kappaB by Toll-like Receptor 3," Nature, vol. 413, pp. 732-738 (2001).

(Continued)

*Primary Examiner* — Rebecca Anderson
(74) *Attorney, Agent, or Firm* — Wilmer Cutler Pickering Hale and Dorr LLP

(57) ABSTRACT

The present invention relates to a compound of Formula I: or a pharmaceutically acceptable salt thereof, wherein the symbols are as defined in the specification; a pharmaceutical composition comprising the same; and a method for treating or preventing autoimmunity disease using the same.

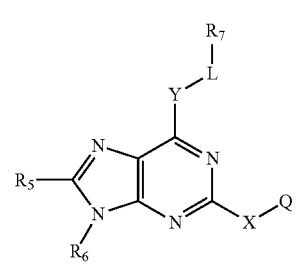

19 Claims, No Drawings

(56) References Cited

OTHER PUBLICATIONS

Aliprantis, et al., "Cell activation and apoptosis by bacterial lipoproteins through toll-like receptor-2," Science, vol. 285, pp. 736-739 (1999).
Bauer, et al. "Human TLR9 confers responsiveness to bacterial DNA via species-specific CpG motif recognition," Proc Natl Acad Sci USA, vol. 98, pp. 9237-9242 (2001).
Berge, et al., "Pharmaceutical Salts", J. Pharm. Sci., vol. 66, pp. 1-19 (1977).
Brightbill, et al., "Host defense mechanisms triggered by microbial lipoproteins through toll-like receptors," Science, vol. 285, pp. 732-736 (1999).
Cao, et al., "TRAF6 is a signal transducer for interleukin-1," Nature, vol. 383, pp. 443-446 (1996).
Extended European Search Report issued by the European Patent Office in European Patent Application No. 12793946.0 dated Oct. 24, 2014 (5 pgs.).
Hacker, et al., "Cell type-specific activation of mitogen-activated protein kinases by CpG-DNA controls interleukin-12 release from antigen-presenting cells," EMBO J, vol. 18, pp. 6973-6982 (1999).
Hayashi, et al. "The innate immune response to bacterial flagellin is mediated by Toll-like receptor 5," Nature, vol. 410, pp. 1099-1103 (2001).
Heil, et al., "Species-specific recognition of single-stranded RNA via toll-like receptor 7 and 8," Science, vol. 303, pp. 1526-1529 (2004).
Hemmi, et al., "A Toll-like receptor recognizes bacterial DNA," Nature, vol. 408, pp. 740-745 (2000).
Hemmi, et al., "Small anti-viral compounds activate immune cells via the TLR7 MyD88-dependent signaling pathway," Nat Immunol, vol. 3, No. 2, pp. 196-200 (2002).
Hoshino, et al., "Cutting edge: Toll-like receptor 4 (TLR4)-deficient mice are hyporesponsive to lipopolysaccharide: evidence for TLR4 as the Lps gene product," Immunol, vol. 162, pp. 3749-3752 (1999).
International Search Report and Written Opinion issued by the U.S. Patent and Trademark Office in International Application No. PCT/US12/40425 mailed Aug. 28, 2012 (9 pgs.).
International Search Report and Written Opinion issued by the U.S. Patent and Trademark Office as International Searching Authority in International Application No. PCT/US12/40417 mailed Aug. 21, 2012 (12 pgs.).
Jurk, et al., "Human TLR7 or TLR8 independently confer responsiveness to the antiviral compound R-848," Nat Immunol vol. 3, p. 499 (2002).
Kalvegren, et al., "Toll-like receptor 2 Stimulation of Platelets is Mediated by Purinergic P2X1-dependent Ca2+ Mobilisation, Cyclooxygenase and Purinergic P2Y1 and P2Y12 Receptor Activation," Thrombosis and Haemostasis, vol. 103, No. 2, pp. 398-407 (Dec. 18, 2009).
Kawai, et al. "Unresponsiveness of MyD88-deficient mice to endotoxin," Immunity, vol. 11, pp. 115-122 (1999).
Langer, R., "New methods of drug delivery," Science, vol. 249, 1527-1533 (1990).
Leadbetter E. A. et al. "Chromatin-IgG complexes activate B cells by dual engagement of IgM and Toll-like receptors," Nature, vol. 416, pp. 603-607 (2002).
Lomaga, et al., "TRAF6 deficiency results in osteopetrosis and defective interleukin-1, CD40, and LPS signaling," Genes Dev, vol. 13, pp. 1015-1024 (1999).
Matsuoka, et al., "Production of free light chains of immunoglobulin by a hematopoietic cell line derived from a patient with multiple myeloma," Proc Soc Exp Biol Med, vol. 125, pp. 1246-1250 (1967).
Medzhitov, et al., "A human homologue of the *Drosophila* Toll protein signals activation of adaptive immunity," Nature, vol. 388, pp. 394-397 (1997).
Medzhitov, et al., "MyD88 is an adaptor protein in the hToll/IL-1 receptor family signaling pathways," Mol Cell, vol. 2, pp. 253-258 (1998).
Murphy, et al., "Regulation of interleukin 12 p40 expression through an NF-kappa B half-site," Mol Cell Biol, vol. 15, pp. 5258-5267 (1995).
Muzio, et al., "IRAK (Pelle) family member IRAK-2 and MyD88 as proximal mediators of IL-1 signaling," Science, vol. 278, 1612-1615 (1997).
Ozinsky, et al., "The repertoire for pattern recognition of pathogens by the innate immune system is defined by cooperation between toll-like receptors," Proc Natl Acad Sci USA, vol. 97, No. 25, pp. 13766-13771 (2000).
Poltorak, et al., "Defective LPS signaling in C3H/HeJ and C57BL/10ScCr mice: mutations in Tlr4 gene," Science, vol. 282, pp. 2085-2088 (1998).
Sun, et al., "TLR7/9 antagonists as therapeutics for immune-mediated inflammatory disorders," Inflammation and Allergy Drug Targets, vol. 6, pp. 223-235 (2007).
Takeshita, et al., "CpG ODN-mediated regulation of IL-12 p40 transcription," Eur J Immunol, vol. 30, pp. 1967-1976 (2000).
Takeshita, et al., "Positive and negative regulatory elements contribute to CpG oligonucleotide-mediated regulation of human IL-6 gene expression," Eur J Immunol, vol. 30, pp. 108-116 (2000).
Takeuchi, et al., "Differential roles of TLR2 and TLR4 in recognition of gram-negative and gram-positive bacterial cell wall components," Immunity, vol. 11, pp. 443-451 (1999).
Takeuchi, et al., "Discrimination of bacterial lipoproteins by Toll-like receptor 6" Int Immunol, vol. 13, pp. 933-940 (2001).
Taylor, E.C., Jr., "Pteridines, VIII. the Synthesis of 2,4-bis(alkylamino)-6,7-diphenylpteridines," Journal of the American Chemical Society, vol. 74, pp. 1648-1650 (1952).
Underhill, et al., "The Toll-like receptor 2 is recruited to macrophage phagosomes and discriminates between pathogens," Nature, vol. 401, pp. 811-815 (1999).
Vollmer, et al., "Characterization of three CpG oligodeoxynucleotide classes with distinct immunostimulatory activities," Eur J Immunol, vol. 34, pp. 251-262 (2004).
Wei, et al., "Homology modeling of human Toll-like receptors TLR7, 8, and 9 ligand-binding domains," Protein Science, vol. 18, pp. 1684-1691 (2009).
Wesche, et al., "MyD88: an adapter that recruits IRAK to the IL-1 receptor complex," Immunity, vol. 7, pp. 837-847 (1997).
Yoshimura, et al., "Cutting edge: recognition of Gram-positive bacterial cell wall components by the innate immune system occurs via Toll-like receptor 2," J. Immunol, vol. 163, pp. 1-5 (1999).

\* cited by examiner

SEQUENCE LISTING

<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tcgtcgtttt gtcgttttgt cgtt                                          24

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage between positions
<220> FEATURE:
<221> NAME/KEY: misc_feature
<222> LOCATION: (15)..(20)
<223> OTHER INFORMATION: Phosphorothioate linkage between positions

<400> SEQUENCE: 2
gggggacgat cgtcggggggg                                              20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcgtcgtttt cggcgcgcgc cg                                            22

IMMUNE SYSTEM MODULATORS

RELATED APPLICATIONS

This application claims priority to U.S. Provisional Patent Application No. 61/491,966, filed Jun. 1, 2011, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Sep. 30, 2015, is named 2205963_122US2_SL.txt and is 1,227 bytes in size.

FIELD OF THE INVENTION

The invention relates to generally to the field of immunology. More particularly, the invention relates to compositions and methods for altering immune function. More specifically, the invention relates to compositions and methods for affecting immune stimulation mediated through Toll-like receptor (TLR) molecules.

BACKGROUND OF THE INVENTION

Stimulation of the immune system, which includes stimulation of either or both innate immunity and adaptive immunity, is a complex phenomenon that can result in either protective or adverse physiologic outcomes for the host. In recent years there has been increased interest in the mechanisms underlying innate immunity, which is believed to initiate and support adaptive immunity. This interest has been fueled in part by the recent discovery of a family of highly conserved pattern recognition receptor proteins known as Toll-like receptors (TLRs) believed to be involved in innate immunity as receptors for pathogen-associated molecular patterns (PAMPs) and danger associated molecular patterns (DAMPs). Compositions and methods useful for modulating innate immunity are therefore of great interest, as they may affect therapeutic approaches to conditions involving autoimmunity, inflammation, atherosclerosis, allergy, asthma, graft rejection, graft versus host disease (GvHD), infection, cancer, and immunodeficiency.

Toll-like receptors (TLRs) are a family of pattern recognition and signaling molecules involved in innate immunity. This family includes at least twelve members, designated TLR1-TLR13, for which the function and specificity are known for most but not all members. Certain of these TLRs are known to signal in response to encounter with particular types of nucleic acid molecules. For example, TLR9 signals in response to CpG-containing DNA, TLR3 signals in response to double-stranded RNA, and TLR7 and TLR8 signal in response to certain single-stranded RNA. There have been a number of reports describing the immunostimulatory effect of certain types of nucleic acid molecules, including CpG nucleic acids and double-stranded RNA. Of note, it was reported that Toll-like receptor 9 (TLR9) recognizes bacterial DNA and CpG DNA while TLR7 and 8 recognize single stranded RNA: Hemmi H et al. (2000) Nature 408:740-5; Bauer S. et al. (2001) Proc Natl Acad Sci USA 98:9237-42; Heil et al. (2004) Science, 303:1526. In addition to their natural ligands, certain synthetic or artificial ligands for these nucleic-acid responsive TLRs are also known. These include certain CpG oligodeoxyribonucleotides (CpG ODN), oligoribonucleotides (ORN) and certain ORN analogs, and certain small molecules including imiquimod (R-837) and resiquimod (R-848). Imiquimod and resiquimod are classified as imidazoaminoquinoline-4-amines; the former is currently marketed as Aldara™ by 3M Pharmaceuticals for topical treatment of anogenital warts associated with papillomavirus infection. In addition to their use in the treatment of certain viral infections such as papillomavirus, certain TLR agonists are also believed to be useful as adjuvants, antitumor agents, and anti-allergy agents. Because a number of diseases and conditions can be treated by enhancing innate immunity, there is a continued need for additional and improved TLR agonists.

It was also recently reported that immune complexes containing IgG and nucleic acid can stimulate TLR9 and participate in B-cell activation in certain autoimmune diseases. Leadbetter E. A. et al. (2002) Nature 416:595-8. Similar and additional documentation of these claims have been made for TLR7, 8 and 9: reviewed in Sun S. et al. (2007) Inflammation and Allergy—Drug Targets 6:223-235.

SUMMARY OF THE INVENTION

Compounds as immune system modulators bearing a purine core are described. The molecules described herein can alter TLR-mediated immunostimulatory signaling by inhibiting TLR signaling and thus can be useful as inhibitors of immune stimulation. Compositions and methods described herein are useful for inhibiting immune stimulation in vitro and in vivo. Such compositions and methods thus are useful in a number of clinical applications, including as pharmaceutical agents and methods for treating conditions involving unwanted immune activity, including inflammatory and autoimmune disorders. The compositions of the invention can also be used in methods for the preparation of medicaments for use in the treatment of conditions involving unwanted immune activity, including a variety of inflammatory and autoimmune disorders.

In one aspect, the present invention provides a compound of Formula I, or a pharmaceutically acceptable salt thereof,

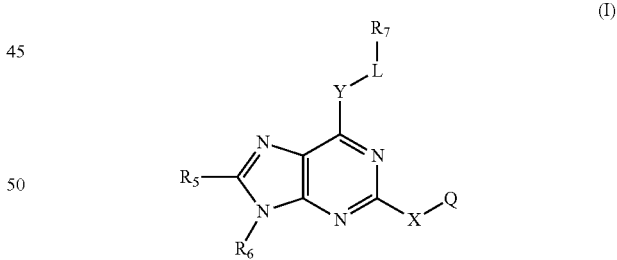

(I)

wherein

X is absent or is an alkyl, alkylamino, cycloalkyl, aryl, or heterocycle;

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl or $NR_3R_4$, wherein the heteroaryl is optionally substituted by $(C_1\text{-}C_4)$alkyl;

$R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

L is alkyl or alkenyl containing from 2 to 10 carbon atoms;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1\text{-}C_4)$alkyl, aryl, aralkyl, benzyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle;

provided that when $R_5$ and $R_6$ are H or $C_1\text{-}C_3$ alkyl, then Q is not H.

In some embodiments, X is absent. In other embodiments, X is alkyl or alkylamino. In yet other embodiments, X is cycloalkyl. In yet other embodiments, X is aryl. In yet other embodiments, X is heterocycle.

In some embodiments, Y is oxygen. In other embodiments, Y is sulfur. In yet other embodiments, Y is $NR_{11}$.

In some embodiments, L is alkyl or alkenyl containing from 2 to 4 carbon atoms.

In some embodiments, the compound of Formula I has the structure of Formula II:

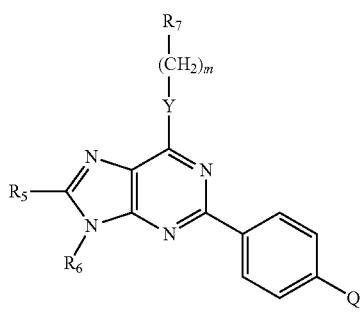

(II)

wherein

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1\text{-}C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl, wherein the heteroaryl is optionally substituted by $(C_1\text{-}C_4)$alkyl;

m is 2-6;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1\text{-}C_4)$alkyl, aryl, aralkyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle;

provided that when $R_5$ and $R_6$ are H or $C_1\text{-}C_3$ alkyl, then Q is not H.

In some embodiments, the compound of Formula I has the structure of Formula III:

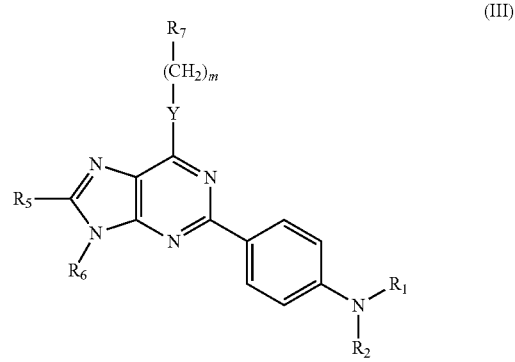

(III)

wherein $R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1\text{-}C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl, wherein the heteroaryl is optionally substituted by $(C_1\text{-}C_4)$alkyl;

m is 2-6;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1\text{-}C_4)$alkyl, aryl, aralkyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

In some embodiments, the compound of Formula I has the structure of Formula IV:

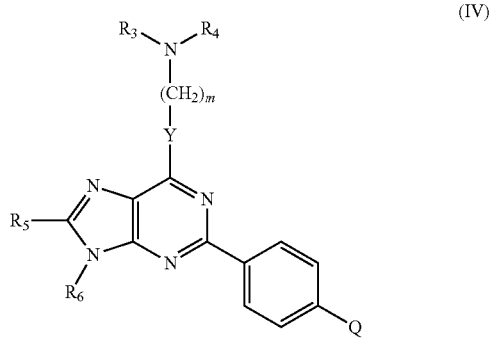

(IV)

wherein

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1$-$C_4)$alkyl, phenyl, benzyl, $C(=O)R_{12}$, $(CH_2)_pOR_a$, and $(CH_2)_pNR_bR_c$, in which p is 2-4;

n is 2-6;

$R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1$-$C_4)$alkyl, aryl, aralkyl, heterocycle, $(CH_2)_pNR_bR_c$, or alkylheterocycle, wherein r is 0-4;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle;

provided that when $R_5$ and $R_6$ are H or $C_1$-$C_3$ alkyl, then Q is not H.

In some embodiments, Q is H, $OR_1$, or $SR_1$.

In some embodiments, $R_1$ and $R_2$ are each independently hydrogen, alkyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1$-$C_4)$alkyl, phenyl, benzyl, $C(=O)R_{12}$, $(CH_2)_pOR_a$, and $(CH_2)_pNR_bR_c$, in which p is 2-4.

In some embodiments, $NR_1R_2$, $NR_3R_4$, and $NR_bR_c$ are each independently a heterocycle selected from

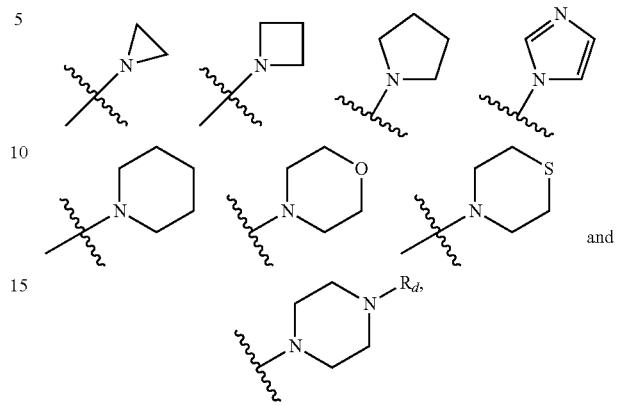

and in which $R_d$ is H, Me, Et, n-Pr, i-Pr, n-Bu, i-Bu, t-Bu, $CH_2CMe_3$, Ph, $CH_2Ph$, $C(=O)R_{12}$, $(CH_2)_pOR_a$, and $(CH_2)_pNR_bR_c$, wherein $R_{12}$ is alkyl, phenyl, or heterocycle; $R_a$, $R_b$ and $R_c$ are each independently hydrogen, or $(C_1$-$C_4)$ alkyl, or $R_b$ and $R_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4.

In some embodiments, $R_5$ is hydrogen, halogen, $(C_1$-$C_4)$ alkyl, hydroxy, $(C_1$-$C_4)$alkoxy, $SR_a$, $S(=O)R_a$, $S(=O)_2R_a$, $S(=O)_2NR_bR_c$, in which $R_a$, $R_b$ and $R_c$ are each independently hydrogen or $(C_1$-$C_4)$alkyl.

In some embodiments, $R_6$ is hydrogen

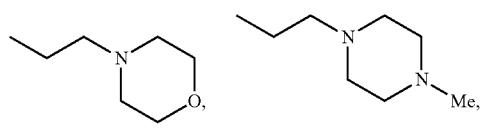

or $(C_1$-$C_4)$alkyl.

In some embodiments, the compound of Formula I is one or more compounds selected from the compounds in Tables 1-2.

In another aspect, a pharmaceutical composition is described, comprising at least one a compound of Formula I, or a pharmaceutically acceptable salt thereof, and a pharmaceutically-acceptable carrier or diluent,

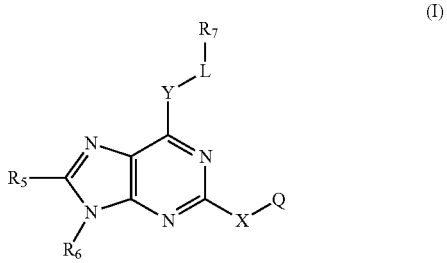

(I)

wherein
X is absent or is an alkyl, alkylamino, cycloalkyl, aryl, or heterocycle;

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl or $NR_3R_4$, wherein the heteroaryl is optionally substituted by $(C_1-C_4)$alkyl;

$R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

L is alkyl or alkenyl containing from 2 to 10 carbon atoms;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$alkyl, aryl, aralkyl, benzyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle;

provided that when $R_5$ and $R_6$ are H or $C_1-C_3$ alkyl, then Q is not H.

In yet another aspect, a method of treating an inflammatory or autoimmune disease in a mammalian species in need thereof is described, comprising administering to the mammalian species a therapeutically effective amount of at least one compound of Formula I,

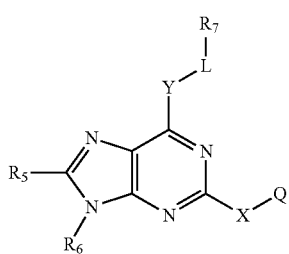

(I)

wherein
X is absent or is an alkyl, alkylamino, cycloalkyl, aryl, or heterocycle;

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl or $NR_3R_4$, wherein the heteroaryl is optionally substituted by $(C_1-C_4)$alkyl;

$R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

L is alkyl or alkenyl containing from 2 to 10 carbon atoms;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$alkyl, aryl, aralkyl, benzyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

In some embodiments, the autoimmune disease is selected from cutaneous and systemic lupus erythematosus, insulin-dependent diabetes mellitus, rheumatoid arthritis, multiple sclerosis, atherosclerosis, psoriasis, psoriatic arthritis, inflammatory bowel disease, atherosclerosis, ankylosing spondylitis, autoimmune hemolytic anemia, Behget's syndrome, Goodpasture's syndrome, Graves' disease, Guillain-Barre syndrome, Hashimoto's thyroiditis, idiopathic thrombocytopenia, io myasthenia gravis, pernicious anemia, polyarteritis nodosa, polymyositis/dermatomyositis, primary biliary sclerosis, sarcoidosis, sclerosing cholangitis, Sjogren's syndrome, systemic sclerosis (scleroderma and CREST syndrome), Takayasu's arteritis, temporal arteritis, and Wegener's granulomatosis. In some specific embodiments, the autoimmune disease is systemic lupus erythematosus. In some specific embodiments, the autoimmune disease is insulin-dependent diabetes mellitus. In some specific embodiments, the autoimmune disease is rheumatoid arthritis. In some specific embodiments, the autoimmune disease is multiple sclerosis. In some specific embodiments, the autoimmune disease is Sjogren's syndrome. In some specific embodiments, the autoimmune disease is psoriasis.

In yet another aspect, a method of inhibiting TLR-mediated immunostimulation in a mammalian species in need thereof is described, comprising administering to the mammalian species a therapeutically effective amount of at least one compound of Formula I,

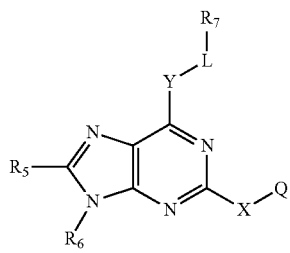

(I)

wherein

X is absent or is an alkyl, alkylamino, cycloalkyl, aryl, or heterocycle;

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl or $NR_3R_4$, wherein the heteroaryl is optionally substituted by $(C_1-C_4)$alkyl;

$R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

L is alkyl or alkenyl containing from 2 to 10 carbon atoms;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$ alkyl, aryl, aralkyl, benzyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

In yet another aspect, a method of inhibiting TLR-mediated immunostimulatory signaling is described, comprising contacting a cell expressing a TLR with an effective amount of at least one compound of Formula I,

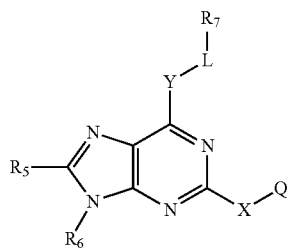

(I)

wherein

X is absent or is an alkyl, alkylamino, cycloalkyl, aryl, or heterocycle;

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl or $NR_3R_4$, wherein the heteroaryl is optionally substituted by $(C_1-C_4)$alkyl;

$R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

L is alkyl or alkenyl containing from 2 to 10 carbon atoms;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$ alkyl, aryl, aralkyl, benzyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

FURTHER DESCRIPTION OF THE INVENTION

Definitions

The following are definitions of terms used in the present specification. The initial definition provided for a group or term herein applies to that group or term throughout the present specification individually or as part of another group, unless otherwise indicated. Unless otherwise defined, all technical and scientific terms used herein have the same meaning as commonly understood by one of ordinary skill in the art.

The terms "alkyl" and "alk" refer to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "$(C_1-C_4)$alkyl" refers to a straight or branched chain alkane (hydrocarbon) radical containing from 1 to 4 carbon atoms, such as methyl, ethyl, propyl, isopropyl, n-butyl, t-butyl, and isobutyl. "Substituted alkyl" refers to an alkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $CCl_3$), cyano, nitro, oxo (i.e., $=O$), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_e$, $NR_bS(=O)_2R_e$, $NR_bP(=O)_2R_e$, $S(=O)_2NR_bR_e$, $P(=O)_2NR_bR_c$, $C(=O)OR_d$, $C(=O)R_a$, $C(=O)NR_bR_e$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. In the aforementioned exemplary substitutents, groups such as alkyl, cycloalkyl, alkenyl, alkynyl, cycloalkenyl, heterocycle and aryl can themselves be optionally substituted.

The term "alkenyl" refers to a straight or branched chain hydrocarbon radical containing from 2 to 12 carbon atoms and at least one carbon-carbon double bond. Exemplary such groups include ethenyl or allyl. The term "$C_2-C_6$ alkenyl" refers to a straight or branched chain hydrocarbon radical containing from 2 to 6 carbon atoms and at least one carbon-carbon double bond, such as ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. "Substituted alkenyl" refers to an alkenyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $CCl_3$), cyano, nitro, oxo (i.e., $=O$), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_e$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted.

The term "alkynyl" refers to a straight or branched chain hydrocarbon radical containing from 2 to 12 carbon atoms and at least one carbon to carbon triple bond. Exemplary such groups include ethynyl. The term "$C_2-C_6$ alkynyl" refers to a straight or branched chain hydrocarbon radical containing from 2 to 6 carbon atoms and at least one carbon-carbon triple bond, such as ethynyl, prop-1-ynyl, prop-2-ynyl, but-1-ynyl, but-2-ynyl, pent-1-ynyl, pent-2-ynyl, hex-1-ynyl, hex-2-ynyl, hex-3-ynyl. "Substituted alkynyl" refers to an alkynyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $CCl_3$), cyano, nitro, oxo (i.e., $=O$), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted.

The term "cycloalkyl" refers to a fully saturated cyclic hydrocarbon group containing from 1 to 4 rings and 3 to 8 carbons per ring. "$C_3-C_7$ cycloalkyl" refers to cyclopropyl, cyclobutyl, cyclopentyl, cyclohexyl, or cycloheptyl. "Substituted cycloalkyl" refers to a cycloalkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $CCl_3$), cyano, nitro, oxo (i.e., $=O$), $CF_3$, $OCF3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted. Exemplary substituents also include spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substitutents can themselves be optionally substituted.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $CCl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted. Exemplary substituents also include spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1 to 3 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $CCl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted. Exemplary substituents also include fused cyclic groups, especially fused cycloalkyl, fused cycloalkenyl, fused heterocycle, or fused aryl, where the aforementioned cycloalkyl, cycloalkenyl, heterocycle and aryl substituents can themselves be optionally substituted.

The term "carbocycle" refers to a fully saturated or partially saturated cyclic hydrocarbon group containing from 1 to 4 rings and 3 to 8 carbons per ring, or cyclic, aromatic hydrocarbon groups that have 1 to 5 aromatic rings, especially monocyclic or bicyclic groups such as phenyl, biphenyl or naphthyl. The term "carbocycle" encompasses cycloalkyl, cycloalkenyl, cycloalkynyl and aryl as defined hereinabove. The term "substituted carbocycle" refers to carbocycle or carbocyclic groups substituted with one or more substituents, preferably 1 to 4 substituents, at any available point of attachment. Exemplary substituents include, but are not limited to, those described above for substituted cycloalkyl, substituted cycloalkenyl, substituted cycloalkynyl and substituted aryl. Exemplary substituents also include spiro-attached or fused cyclic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 8 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

"Substituted heterocycle" and "substituted heterocyclic" (such as "substituted heteroaryl") refer to heterocycle or heterocyclic groups substituted with one or more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $CCl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include spiro-attached or fused cyclic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "alkylamino" refers to a group having the structure —NHR', wherein R' is hydrogen, alkyl or substituted alkyl, cycloalkyl or substituted cyclolakyl, as defined herein. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each independently alkyl or substituted alkyl, cycloalkyl or substituted cycloalkyl, cycloalkenyl or substituted cyclolakenyl, aryl or substituted aryl, heterocylyl or substituted heterocyclyl, as defined herein. R and R' may be the same or different in an dialkyamino moiety. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

The terms "halogen" or "halo" refer to chlorine, bromine, fluorine or iodine.

Unless otherwise indicated, any heteroatom with unsatisfied valences is assumed to have hydrogen atoms sufficient to satisfy the valences.

The compounds of the present invention may form salts which are also within the scope of this invention. Reference to a compound of the present invention is understood to include reference to salts thereof, unless otherwise indicated. The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the present invention may be formed, for example, by reacting a compound I with an amount of acid or base, such as an equivalent amount, in a medium such as one in which the salt precipitates or in an aqueous medium followed by lyophilization.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention which contain an acidic moiety, such but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds of the invention are also contemplated herein. The term "prodrug" as employed herein denotes a compound that, upon administration to a subject, undergoes chemical conversion by metabolic or chemical processes to yield a compound of the present invention, or a salt and/or solvate thereof. Solvates of the compounds of the present invention include, for example, hydrates.

Compounds of the present invention, and salts or solvates thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the International Union of Pure and Applied Chemistry (IUPAC) 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

Compounds of the present invention are, subsequent to their preparation, preferably isolated and purified to obtain a composition containing an amount by weight equal to or greater than 90%, for example, equal to greater than 95%, equal to or greater than 99% of the compounds ("substantially pure" compounds), which is then used or formulated as described herein. Such "substantially pure" compounds of the present invention are also contemplated herein as part of the present invention.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Throughout the specifications, groups and substituents thereof may be chosen to provide stable moieties and compounds.

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

The present invention also includes isotopically labeled compounds, which are identical to the compounds disclosed herein, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^{2}$H, $^{3}$H, $^{13}$C, $^{11}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, or an enantiomer, diastereomer, tautomer, or pharmaceutically acceptable salt or solvate thereof, which contain the aforementioned isotopes and/or other isotopes of other atoms are within the scope of this invention. Certain isotopically labeled compounds of the present invention, for example those into which radioactive isotopes such as $^{3}$H and $^{14}$C are incorporated, are useful in drug and/or substrate tissue distribution assays. Tritiated, i.e., $^{3}$H, and carbon-14, i.e., $^{14}$C, isotopes are particularly preferred for their ease of preparation and detectability. Further, substitution with heavier isotopes such as deuterium, i.e., $^{2}$H, can afford certain therapeutic advantages resulting from greater metabolic stability, for example increased in vivo half-life or reduced dosage requirements and, hence, may be preferred in some circumstances. Isotopically labeled compounds can generally be prepared by carrying out the procedures disclosed in the Schemes and/or in the Examples below, by substituting a readily available isotopically labeled reagent for a non-isotopically labeled reagent.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

As used herein, the term "adaptive immune response" refers to any type of antigen-specific immune response. Adaptive immune responses, which are also known in the art as specific immune responses, involve lymphocytes are also characterized by immunological memory, whereby response to a second or subsequent exposure to antigen is more vigorous than the response to a first exposure to the antigen. The term adaptive immune response encompasses both humoral (antibody) immunity and cell-mediated (cellular) immunity.

As used herein, "allergy" refers to acquired hypersensitivity to a substance (allergen). Allergic conditions include eczema, allergic rhinitis or coryza, hay fever, asthma, urticaria (hives) and food allergies, and other atopic conditions.

As used herein, the term "antigenic substance" refers to any substance that induces an adaptive (specific) immune response. An antigen typically is any substance that can be specifically bound by a T-cell antigen receptor, antibody, or B-cell antigen receptor. Antigenic substances include, without limitation, peptides, proteins, carbohydrates, lipids, phospholipids, nucleic acids, autacoids, and hormones. Antigenic substances further specifically include antigens that are classified as allergens, cancer antigens, and microbial antigens.

As used herein, "asthma" refers to a disorder of the respiratory system characterized by inflammation, narrowing of the airways and increased reactivity of the airways to inhaled agents. Asthma is frequently, although not exclusively associated with atopic or allergic symptoms. For example, asthma can be precipitated by exposure to an allergen, exposure to cold air, respiratory infection, and exertion.

As used herein, the terms "autoimmune disease" and, equivalently, "autoimmune disorder" and "autoimmunity", refer to immunologically mediated acute or chronic injury to a tissue or organ derived from the host. The terms encompass both cellular and antibody-mediated autoimmune phenomena, as well as organ-specific and organ-nonspecific autoimmunity. Autoimmune diseases include insulin-dependent diabetes mellitus, rheumatoid arthritis, systemic lupus erythematosus, multiple sclerosis, atherosclerosis, psoriasis and inflammatory bowel disease. Autoimmune diseases also include, without limitation, ankylosing spondylitis, autoimmune hemolytic anemia, Beget's syndrome, Goodpasture's syndrome, Graves' disease, Guillain-Barre syndrome, Hashimoto's thyroiditis, idiopathic thrombocytopenia, myasthenia gravis, pernicious anemia, polyarteritis nodosa, polymyositis/dermatomyositis, primary biliary sclerosis, sarcoidosis, sclerosing cholangitis, Sjögren's syndrome, systemic sclerosis (scleroderma and CREST syndrome), Takayasu's arteritis, temporal arteritis, and Wegener's granulomatosis. Autoimmune diseases also include certain immune complex-associated diseases.

As used herein, the terms "cancer" and, equivalently, "tumor" refer to a condition in which abnormally replicating cells of host origin are present in a detectable amount in a subject. The cancer can be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric (stomach) cancer; intraepithelial neoplasms; leukemias; lymphomas; liver cancer; lung cancer (e. g., small cell and non-small cell); melanoma; neuroblastomas; oral cancer; ovarian cancer; pancreatic cancer; prostate cancer; rectal cancer; renal (kidney) cancer; sarcomas; skin cancer; testicular cancer; thyroid cancer; as well as other carcinomas and sarcomas. Cancers can be primary or metastatic.

As used herein, the term "CpG DNA" refers to an immunostimulatory nucleic acid which contains a cytosine-guanine (CG) dinucleotide, the C residue of which is unmethylated. The effects of CpG nucleic acids on immune modulation have been described extensively in U.S. patents such as U.S. Pat. Nos. 6,194,388; 6,207,646; 6,239,116; and 6,218,371, and published international patent applications, such as WO98/37919, WO98/40100, WO98/52581, and WO99/56755. The entire contents of each of these patents and published patent applications is hereby incorporated by reference. The entire immunostimulatory nucleic acid can be unmethylated or portions may be unmethylated but at least the C of the 5'-CG-3' must be unmethylated.

In one embodiment the CpG DNA is a CpG ODN that has a base sequence provided by 5'-TCGTCGTTTTGTCGTTTTGTCGTT-3' (ODN 2006; SEQ ID NO:1). CpG ODN have been further classified by structure and function into at least the following three classes or types, all of which are intended to be encompassed within the term CpG DNA as used herein: B-class CpG ODN such as ODN 2006 include the originally described immunostimulatory CpG ODN and characteristically activate B cells and NK cells but do not induce or only weakly induce expression of type I interferon (e. g., IFN-a). A-class CpG ODN, described in published PCT international application WO 01/22990, incorporate a CpG motif, include a chimeric phosphodiester/phosphorothioate backbone, and characteristically activate NK cells and induce plasmacytoid dendritic cells to express large amounts of IFN-a but do not activate or only weakly activate B cells. An example of an A-class CpG ODN is 5'-G*G*GGGACGATCGTCG*G*G*G*G-3' (ODN 2216, SEQ ID NO: 2), wherein "*" represents phosphorothioate and " " represents phosphodiester. C-class CpG ODN incorporate a CpG, include a wholly phosphorothioate backbone, include a GC-rich palindromic or nearly-palindromic region, and are capable of both activating B cells and inducing expression of IFN-a. C-class CpG ODN have been described, for example, in published U.S. patent application 2003/0148976. An example of a C-class CpG ODN is 5'-TCGTCGTTTTCGGCGCGCGCCG-3' (ODN 2395; SEQ ID NO: 3). For a review of the various classes of CpG ODN, see also Vollmer J et al. (2004) Eur J Immunol 34: 251-62.

As used herein, "cytokine" refers to any of a number of soluble proteins or glycoproteins that act on immune cells through specific receptors to affect the state of activation and function of the immune cells. Cytokines include interferons, interleukins, tumor necrosis factor, transforming growth factor beta, colony-stimulating factors (CSFs), chemokines, as well as others. Various cytokines affect innate immunity, acquired immunity, or both. Cytokines specifically include, without limitation, IFN-a, IFN-p, IFN-y, IL-1, IL-2, IL-3, IL-4, IL-5, IL-6, IL-9, IL-10, IL-12, IL-13, IL-18, TNF-α, TGF-β, granulocyte colony-stimulating factor (G-CSF), and granulocyte-macrophage colony-stimulating factor (GM-CSF). Chemokines specifically include, without limitation, IL-8, IP-10, I-TAC, RANTES, MIP-1a, MIP-1p, Gro-a, Gro-, Gro-y, MCP-1, MCP-2, and MCP-3.

Most mature CD4+ T helper cells can be categorized into cytokine-associated, cross-regulatory subsets or phenotypes: Th1, Th2, Th17, or Treg. Th1 cells are associated with IL-2, IL-3, IFN, GM-CSF and high levels of TNF-a. Th2 cells are associated with IL-3, IL-4, IL-5, IL-6, IL-9, IL-10, IL-13, GM-CSF and low levels of TNF-a. The Th1 subset promotes both cell-mediated immunity and humoral immunity that is characterized by immunoglobulin class switching to IgG2a in mice. Th1 responses can also be associated with delayed-type hypersensitivity and autoimmune disease. The Th2 subset induces primarily humoral immunity and induces immunoglobulin class switching to IgE and IgGl in mice. The antibody isotypes associated with Th1 responses generally have good neutralizing and opsonizing capabilities, whereas those associated with Th2 responses are associated more with allergic responses.

Several factors have been shown to influence commitment to Th1 or Th2 profiles. The best characterized regulators are cytokines IL-12 and IFN-y are positive Th1 and negative Th2 regulators. IL-12 promotes IFN-y production, and IFN-y provides positive feedback for IL-12. IL-4 and IL-10 appear to be required for the establishment of the Th2 cytokine profile and to down-regulate Th1 cytokine production; the effects of IL-4 are in some cases dominant over those of IL-12. IL-13 was shown to inhibit expression of inflammatory cytokines, including IL-12 and TNF-a by LPS-induced monocytes, in a way similar to IL-4.

As used herein, "effective amount" refers to any amount that is necessary or sufficient for achieving or promoting a desired outcome. In some instances an effective amount is a therapeutically effective amount. A therapeutically effective amount is any amount that is necessary or sufficient for promoting or achieving a desired biological response in a subject. The effective amount for any particular application can vary depending on such factors as the disease or condition being treated, the particular agent being administered, the size of the subject, or the severity of the disease or condition. One of ordinary skill in the art can empirically determine the effective amount of a particular agent without necessitating undue experimentation.

As used herein, "graft rejection" refers to immunologically mediated hyperacute, acute, or chronic injury to a tissue or organ derived from a source other than the host. The term thus encompasses both cellular and antibody-mediated rejection, as well as rejection of both allografts and xenografts.

As used herein, the term "immune cell" refers to a cell belonging to the immune system. Immune cells include T lymphocytes (T cells), B lymphocytes (B cells), natural killer (NK) cells, granulocytes, neutrophils, macrophages, monocytes, dendritic cells, and specialized forms of any of the foregoing, e. g., plasmacytoid dendritic cells, plasma cells, NKT, T helper, and cytotoxic T lymphocytes (CTL).

As used herein, the term "immune complex" refers to any conjugate including an antibody and an antigen specifically bound by the antibody. In one embodiment, the antigen is an autoantigen.

As used herein, the term "immune complex comprising a nucleic acid" refers to any conjugate including an antibody and a nucleic acid-containing antigen specifically bound by the antibody. The nucleic acid-containing antigen can include chromatin, ribosomes, small nuclear proteins, histones, nucleosomes, DNA, RNA, or any combination thereof. The antibody can but need not necessarily bind specifically to a nucleic acid component of the nucleic acid-containing antigen. In some embodiments, the term "immune complex comprising a nucleic acid" refers also to non-antibody complexes such as HMGB1, LL-37, and other nucleic acid binding proteins such as histones, transcription factors and enzymes complexed with nucleic acids.

As used herein, the term "immune complex-associated disease" refers to any disease characterized by the production and/or tissue deposition of immune complexes, including, but not limited to systemic lupus erythematosus (SLE) and related connective tissue diseases, rheumatoid arthritis, hepatitis C- and hepatitis B-related immune complex disease (e. g., cryoglubulinemia), Beget's syndrome, autoimmune glomerulonephritides, and vasculopathy associated with the presence of LDL/anti-LDL immune complexes.

As used herein, "immunodeficiency" refers to a disease or disorder in which the subject's immune system is not functioning in normal capacity or in which it would be useful to boost a subject's immune response for example to eliminate a tumor or cancer (e. g., tumors of the brain, lung (e. g., small cell and non-small cell), ovary, breast, prostate, colon, as well as other carcinomas and sarcomas) or an infection in a subject. The immunodeficiency can be acquired or it can be congenital.

As used herein, "immunostimulatory nucleic acid-associated response in a subject" refers to a measurable response in a subject associated with administration to the subject of an immunostimulatory nucleic acid. Such responses include, without limitation, elaboration of cytokines, chemokines, growth factors, or immunoglobulin; expression of immune cell surface activation markers; Th1/Th2 skewing; and clinical disease activity.

As used herein, the terms "infection" and, equivalently, "infectious disease" refer to a condition in which an infectious organism or agent is present in a detectable amount in the blood or in a normally sterile tissue or normally sterile compartment of a subject. Infectious organisms and agents include viruses, bacteria, fungi, and parasites. The terms encompass both acute and chronic infections, as well as sepsis.

As used herein, the term "innate immune response" refers to any type of immune response to certain pathogen-associated molecular patterns (PAMPs) or danger associated molecular patterns (DAMPs) Innate immunity, which is also known in the art as natural or native immunity, involves principally neutrophils, granulocytes, mononuclear phagocytes, dendritic cells, NKT cells, and NK cells. Innate immune responses can include, without limitation, type I interferon production (e, g., IFN-a), neutrophil activation, macrophage activation, phagocytosis, opsonization, complement activation, and any combination thereof.

As used herein, the term "self-DNA" refers to any DNA derived from the genome of a host subject. In one embodiment, self-DNA includes complementary DNA (cDNA) derived from a host subject. Self-DNA includes intact and degraded DNA.

As used herein, the term "self-RNA" refers to any RNA derived from the genome of a host subject. In one embodiment self-RNA is a messenger RNA (mRNA) derived from a host subject. In another embodiment self-RNA is a regulatory RNA such as micro RNAs. In one embodiment self-RNA includes ribosomal RNA (rRNA) derived from a host subject. Self-RNA includes intact and degraded RNA.

As used herein, the term "subject" refers to a vertebrate animal. In one embodiment the subject is a mammal. In one embodiment the subject is a human. In other embodiments the subject is a non-human vertebrate animal, including, without limitation, non-human primates, laboratory animals, livestock, domesticated animals, and non-domesticated animals.

As used herein, "subject having or at risk of developing TLR-mediated immunostimulation" refers to a subject exposed to or at risk of exposure to a PAMPs, DAMPs or other TLR ligand.

As used herein, the terms "Toll-like receptor" and, equivalently, "TLR" refer to any member of a family of at least thirteen highly conserved mammalian pattern recognition receptor proteins (TLR1-TLR13) which recognize PAMPs, DAMPs and act as key signaling elements in innate immunity. TLR polypeptides share a characteristic structure that includes an extracellular (extracytoplasmic) domain that has leucine-rich repeats, a transmembrane domain, and an intracellular (cytoplasmic) domain that is involved in TLR signaling. TLRs include but are not limited to human TLRs.

Nucleic acid and amino acid sequences for all ten currently known human TLRs are available from public databases such as GenBank. Similarly, nucleic acid and amino acid sequences for various TLRs from numerous non-human species are also available from public databases including GenBank. For example, nucleic acid and amino acid sequences for human TLR9 (hTLR9) can be found as GenBank accession numbers AF245704 (coding region spanning nucleotides 145-3243) and AAF78037, respectively. Nucleic acid and amino acid sequences for murine TLR9 (mTLR9) can be found as GenBank accession numbers AF348140 (coding region spanning nucleotides 40-3138) and AAK29625, respectively. The deduced human TLR9 protein contains 1,032 amino acids and shares an overall amino acid identity of 75.5% with mouse TLR9. Like other TLR proteins, human TLR9 contains extracellular leucine-rich repeats (LRRs) and a cytoplasmic Toll/interleukin-1R (TIR) domain. It also has a signal peptide (residues 1-25) and a transmembrane domain (residues 819-836).

Nucleic acid and amino acid sequences for human TLR8 (hTLR8) can be found as GenBank accession numbers AF245703 (coding region spanning nucleotides 49-3174) and AAF78036, respectively. Nucleic acid and amino acid sequences for murine TLR8 (mTLR8) can be found as GenBank accession numbers AY035890 (coding region spanning nucleotides 59-3157) and AAK62677, respectively.

Nucleic acid and amino acid sequences for human TLR7 (hTLR7) can be found as GenBank accession numbers AF240467 (coding region spanning nucleotides 135-3285) and AAF60188, respectively. Nucleic acid and amino acid sequences for murine TLR7 (mTLR7) can be found as GenBank accession numbers AY035889 (coding region spanning nucleotides 49-3201) and AAK62676, respectively.

Nucleic acid and amino acid sequences for human TLR3 (hTLR3) can be found as GenBank accession numbers NM003265 (coding region spanning nucleotides 102-2816) and NP003256, respectively. Nucleic acid and amino acid sequences for murine TLR3 (hTLR3) can be found as GenBank accession numbers AF355152 (coding region spanning nucleotides 44-2761) and AAK26117, respectively.

While hTLR1 is ubiquitously expressed, hTLR2, hTLR4 and hTLR5 are present in monocytes, polymorphonuclear phagocytes, and dendritic cells. Muzio M et al. (2000) J Leukoc Biol 67: 450-6. Recent publications reported that hTLR1, hTLR6, hTLR7, hTLR9 and hTLR10 are present in human B cells. Human TLR7 and hTLR9 are present in plasmacytoid dendritic cells (pDCs), while myeloid dendritic cells express hTLR7 and hTLR8 but not hTLR9. Human TLR8, however, appears not to be expressed in pDCs.

As members of the pro-inflammatory interleukin-1 receptor (IL-1R) family, TLRs share homologies in their cytoplasmic domains called Toll/IL-1R homology (TIR) domains. See PCT published applications PCT/US98/08979 and PCT/US01/16766. Intracellular signaling mechanisms mediated by TLRs appear generally similar, with MyD88 and tumor necrosis factor receptor-associated factor 6 (TRAF6) believed to have critical roles. Wesche H et al. (1997) Immunity 7: 837-47; Medzhitov R et al. (1998) Mol Cell 2: 253-8; Adachi O et al. (1998) Immunity 9: 143-50; Kawai T et al. (1999) Immunity 11: 115-22); Cao Z et al. (1996) Nature 383: 443-6; Lomaga M A et al. (1999) Genes Dev 13: 1015-24. Signal transduction between MyD88 and TRAF6 is known to involve members of the serine-threonine kinase IL-1 receptor-associated kinase (IRAK) family, including at least IRAK-1 and IRAK-2. Muzio M et al. (1997) Science 278: 1612-5.

Briefly, MyD88 is believed to act as an adapter molecule between the TIR domain of a TLR or IL-1R and IRAK (which includes at least any one of IRAK-1, IRAK-2, IRAK-4, and IRAK-M). MyD88 includes a C-terminal Toll homology domain and an N-terminal death domain. The Toll homology domain of MyD88 binds the TIR domain of TLR or IL-1R, and the death domain of MyD88 binds the death domain of the serine kinase IRAK IRAK interacts with TRAF6, which acts as an entryway into at least two pathways, one leading to activation of the transcription factor NF-KB and another leading to activation of Jun and Fos, members of the activator protein-1 (AP-1) transcription factor family. Activation of NF-KB involves the activation of TAK-1, a member of the MAP 3 kinase (MAPK) family, and IKB kinases. The IoB kinases phosphorylate IKB, leading to its-degradation and the translocation of NF-KB to the nucleus. Activation of Jun and Fos is believed to involve MAP kinase kinases (MAPKKs) and MAP kinases ERK, p38, and JNK/SAPK. Both NF-KB and AP-1 are involved in controlling the transcription of a number of key immune response genes, including genes for various cytokines and costimulatory molecules. See Aderem A et al. (2000) Nature 406: 782-7; Hacker H et al. (1999) EMBO J 18: 6973-82.

As used herein, the terms "TLR ligand" and, equivalently, "ligand for a TLR" and "TLR signaling agonist", refer to a molecule, other than a small molecule according to Formula I described herein that interacts, directly or indirectly, with a TLR through a TLR domain other than a TIR domain and induces TLR-mediated signaling. In one embodiment a TLR ligand is a natural ligand, i. e., a TLR ligand that is found in nature. In one embodiment a TLR ligand refers to a molecule other than a natural ligand of a TLR, e. g., a molecule prepared by human activity. In one embodiment the TLR is TLR9 and the TLR signal agonist is a CpG nucleic acid.

Ligands for many but not all of the TLRs have been described. For instance, it has been reported that TLR2 signals in response to peptidoglycan and lipopeptides. Yoshimura A et al. (1999) J Immunol 163: 1-5; Brightbill H D et al. (1999) Science 285: 732-6; Aliprantis A O et al. (1999) Science 285: 736-9; Takeuchi O et al. (1999) Immunity 11: 443-51; Underhill D M et al. (1999) Nature 401: 811-5. TLR4 has been reported to signal in response to lipopolysaccharide (LPS). See Hoshino K et al. (1999) Immunol 162: 3749-52; Poltorak A et al. (1998) Science 282: 2085-8; Medzhitov R et al. (1997) Nature 388: 394-7. Bacterial flagellin has been reported to be a natural ligand for TLR5. See Hayashi F et al. (2001) Nature 410: 1099-1103. TLR6, in conjunction with TLR2, has been reported to signal in response to proteoglycan. See Ozinsky A et al. (2000) Proc Natl Acad Sci USA 97: 13766-71; Takeuchi O et al. (2001) Int Immunol 13: 933-40.

Recently it was reported that TLR9 is a receptor for CpG DNA. Hemmi H et al. (2000) Nature 408: 740-5; Bauer S et al. (2001) Proc Natl Acad Sci USA 98: 9237-42. CpG DNA, which includes bacterial DNA and synthetic DNA with CG dinucleotides in which cytosin is unmethylated, is described in greater detail elsewhere herein. Marshak-Rothstein and colleagues also recently reported their finding that TLR9 signaling can occur in certain autoimmune diseases in response to immune complexes containing IgG and chromatin. Leadbetter E A et al. (2002) Nature 416: 595-8. Thus, in a broader sense it appears that TLR9 can signal in response to self or non-self nucleic acid, either DNA or RNA, when the nucleic acid is presented in a suitable context, e. g., as part of an immune complex.

Recently it was reported that certain imidazoquinoline compounds having antiviral activity are ligands of TLR7 and TLR8. Hemmi H et al. (2002) Nat Immunol 3: 196-200; Jurk M et al. (2002) Nat Immunol 3: 499. Imidazoquinolines are potent synthetic activators of immune cells with antiviral and antitumor properties. Using macrophages from wildtype and MyD88-deficient mice, Hemmi et al. recently reported that two imidazoquinolines, imiquimod and resiquimod (R848), induce tumor necrosis factor (TNF) and interleukin-12 (IL-12) and activate NF-KB only in wildtype cells, consistent with activation through a TLR. Hemmi H et al. (2002) Nat Immunol 3: 196-200. Macrophages from mice deficient in TLR7 but not other TLRs produced no detectable cytokines in response to these imidazoquinolines. In addition, the imidazoquinolines induced dose-dependent proliferation of splenic B cells and the activation of intracellular signaling cascades in cells from wildtype but not TLR7−/− mice. Luciferase analysis established that expression of human TLR7, but not TLR2 or TLR4, in human embryonic kidney cells results in NF-KB activation in response to resiquimod. The findings of Hemmi et al. thus suggested that these imidazoquinoline compounds are non-natural ligands of TLR7 that can induce signaling through TLR7. Recently it was reported that R848 is also a ligand for human TLR8. See Jurk M et al. (2002) Nat Immunol 3:499. Nat Immunol 3: 499. It has also been reported that ssRNA is natural ligand and that aberrant stimulation of TLR7 and or TLR8 by RNA:complexes is involved in autoimmunity.

It was recently reported that ligands of TLR3 include poly (I: C) and double-stranded RNA (dsRNA). For purposes of this invention, poly (I: C) and double-stranded RNA (dsRNA) are classified as oligonucleotide molecules. By stimulating kidney cells expressing one of a range of TLRs with poly (I: C), Alexopoulou et al. reported that only cells expressing TLR3 respond by activating NF-aB. See Alexopoulou L et al. (2001) Nature 413: 732-8.

Alexopoulou et al. also reported that wildtype cells stimulated with poly (I: C) activate NF-KB and produce inflammatory cytokines IL-6, IL-12, and TNF-a, whereas the corresponding responses of TLR3−/−cells were significantly impaired. In contrast, TLR3−/−cells responded equivalently to wildtype cells in response to lipopolysaccharide, peptidoglycan, and CpG dinucleotides. Analysis of MyD88−/− cells indicated that this adaptor protein is involved in dsRNA-induced production of cytokines and proliferative responses, although activation of NF-KB and MAP kinases are not affected, indicating distinct pathways for these cellular responses. Alexopoulou et al. proposed that TLR3 may have a role in host defense against viruses.

As used herein, a "cell expressing a TLR" refers to any cell which expresses, either naturally or artificially, a functional TLR. A functional TLR is a full-length TLR protein or a fragment thereof capable of inducing a signal in response to interaction with its ligand.

Generally, the functional TLR will include at least a TLR ligand-binding fragment of the extracellular domain of the full-length TLR and at least a fragment of a TIR domain capable of interacting with another Toll homology domain-containing polypeptide, e. g., MyD88. In various embodiments the functional TLR is a full-length TLR selected from TLR1, TLR2, TLR3, TLR4, TLR5, TLR6, TLR7, TLR8, TLR9, and TLR10.

Compounds

In one aspect, novel purine compounds are described. Applicants have surprisingly discovered purine compounds as immune system modulators. It is unexpected that the purine compounds as disclosed herein are useful in methods for inhibiting an immune response, both in vitro and in vivo, including methods for treating immune complex associated diseases and autoimmune disorders. In another aspect, the invention provides novel purine compositions. As described further below, these compositions and other purine compositions have been discovered to be useful in methods for inhibiting an immune response, both in vitro and in vivo, including methods for treating immune complex associated diseases and autoimmune disorders. It is also believed that the novel purine compositions as described herein can be used for prevention and treatment of malaria, as well as for treatment of other diseases.

In one aspect, a compound of Formula I or a pharmaceutically acceptable salt thereof is described:

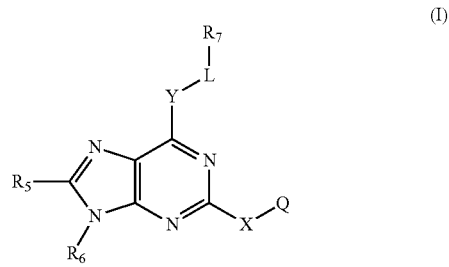

wherein
X is absent or is an alkyl, alkylamino, cycloalkyl, aryl, or heterocycle;

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl or $NR_3R_4$, wherein the heteroaryl is optionally substituted by $(C_1-C_4)$alkyl;

$R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

L is alkyl or alkenyl containing from 2 to 10 carbon atoms;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$ alkyl, aryl, aralkyl, benzyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$ and $R_c$ is independently hydrogen, alkyl, cycloalkyl, heterocycle, aryl, or said $R_b$ and $R_c$ together with the nitrogen atom to which they are bonded optionally form a heterocycle;

provided that when $R_5$ and $R_6$ are H or $C_1$-$C_3$ alkyl, then Q is not H.

In certain embodiments, X is absent. In other embodiments, X is selected from the group consisting of alkyl, alkylamino, cycloalkyl, aryl, and heterocycle. In some embodiments, X is —$(CH_2)_m$—, wherein m is 2-4. In other embodiments, X is aryl. Non-limiting examples of aryl include optionally substituted phenyl and napthyl. In still other embodiments, X is a heterocycle. In some embodiments, X is a saturated heterocycle. Non-limiting examples of saturated heterocycle includes piperizine. In other embodiments, X is an unsaturated hyterocycle. Non-limiting examples of unsaturated heterocycle includes pyridine, pyrazine, pyrimidine, and pyridazine.

In certain embodiments, Q is H, $(CH_2)_qNR_1R_2$, $NR_1(CH_2)_pNR_bR_c$, $OR_1$, $SR_1$, or $CHR_1R_2$, in which q is 0 or 1 and p is 2-4. $R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from ($C_1$-$C_4$) alkyl, phenyl, benzyl, $C(=O)R_{12}$, $(CH_2)_pOR_a$, and $(CH_2)_pNR_bR_c$, in which p is 2-4. In some embodiments, Q is H, $OR_1$, $SR_1$, or $CHR_1R_2$. In other embodiments, Q is —$(CH_2)_qNR_1R_2$. In some specific embodiments, Q is —$(CH_2)_2NR_1R_2$. In some specific embodiments, Q is

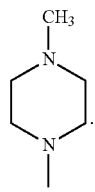

In other embodiments, Q is

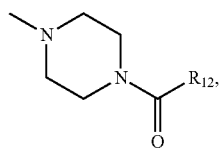

wherein $R_{12}$ is alkyl, aryl, or heterocycle. In some embodiments, $C(=O)R_{12}$ is

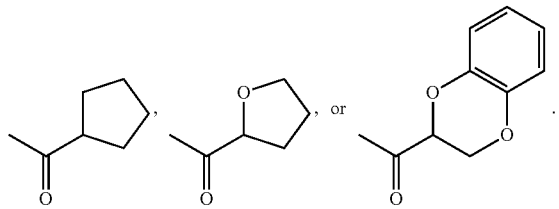

In still other embodiments, Q is $NH(CH_2)_pNR_bR_c$. In some specific embodiments, Q is $NH(CH_2)_2N(CH_3)_2$, $NH(CH_2)_2N(CH_2CH_3)_2$, or $NH(CH_2)_2N(CH_3)(CH_2CH_3)$. In still other embodiments, Q is alkyl. Non-limiting examples of alkyl include methyl, ethyl, propyl, iso-propyl, butyl, sec-butyl, and tert-butyl.

In some embodiments, X is a phenyl group. In these embodiments, Q is attached to phenyl group at the ortho, meta, or para position relative to the purine core. In some specific embodiments, Q is

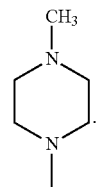

In some specific embodiments, Q is

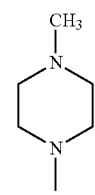

attached to the phenyl group at the para position relative to the purine core. In some specific embodiments, $R_7$ is $NR_3R_4$ and $R_3$ and $R_4$ are combined with the nitrogen atom as a morpholino group. In other specific embodiments, $R_7$ is $NR_3R_4$ and $R_3$ and $R_4$ are each alkyl group such as methyl. In some specific embodiments, each of $R_5$ and $R_6$ is a hydrogen. In some specific embodiments, $R_5$ is halogen such as F, Cl, or Br.

In some embodiments, X is a phenyl group. In these embodiments, Q is attached to phenyl group at the ortho, meta, or para position relative to the purine core. In some specific embodiments, Q is

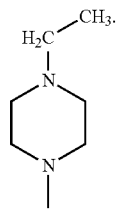

In some specific embodiments, Q is

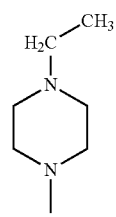

attached to the phenyl group at the para position relative to the purine core. In some specific embodiments, $R_7$ is $NR_3R_4$ and $R_3$ and $R_4$ are combined with the nitrogen atom as a morpholino group. In other specific embodiments, $R_7$ is $NR_3R_4$ and $R_3$ and $R_4$ are each alkyl group such as methyl. In some specific embodiments, each of $R_5$ and $R_6$ is a hydrogen.

In some embodiments, X is a phenyl group. In these embodiments, Q is attached to phenyl group at the ortho, meta, or para position relative to the purine core. In some specific embodiments, Q is

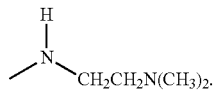

In some specific embodiments, Q is

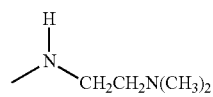

attached to the phenyl group at the ortho position relative to the purine core. In some specific embodiments, $R_7$ is $NR_3R_4$ and $R_3$ and $R_4$ are combined with the nitrogen atom as a morpholino group. In other specific embodiments, $R_7$ is $NR_3R_4$ and $R_3$ and $R_4$ are each alkyl group such as methyl. In some specific embodiments, each of $R_5$ and $R_6$ is a hydrogen. In some specific embodiments, $R_5$ is halogen such as F, Cl, or Br.

In some embodiments, Y is oxygen. In other embodiments, Y is sulfur. In yet other embodiments, Y is $NR_{11}$, where $R_{11}$ is hydrogen, alkyl, cycloalkyl, alkenyl, or aryl group. In some embodiments, L is alkyl or alkenyl containing from 2 to 4 carbon atoms.

In other embodiments, X is a phenyl group and Q is hydrogen. In some specific embodiments, Y is NH. In some specific embodiments, L is —(CH$_2$)$_2$—. In some specific embodiments, $R_7$ is $NR_3R_4$. In still some specific embodiments, $R_3$ and $R_4$ are combined as a morpholino group. In some specific embodiments, $R_6$ is benzyl or

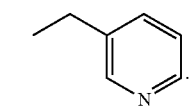

In some specific embodiments, $R_5$ is hydrogen. In other specific embodiments, $R_5$ is halogen.

In certain embodiments, $R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$. In certain specific embodiments, $R_5$ is hydrogen, halogen, (C$_1$-C$_4$)alkyl, hydroxy, (C$_1$-C$_4$)alkoxy, $SR_a$, $S(=O)R_a$, $S(=O)_2R_a$, $S(=O)_2NR_bR_c$, in which $R_a$, $R_b$ and $R_c$ are each independently hydrogen or (C$_1$-C$_4$)alkyl. In some embodiments, $R_5$ is a halogen such as F, Cl, Br, or I. In other embodiments, $R_5$ is OH or SH. In still other embodiments, $R_5$ is S-alkyl or SO$_2$-alkyl. In still other embodiments, $R_5$ is alkyl. In still other embodiments, $R_5$ is

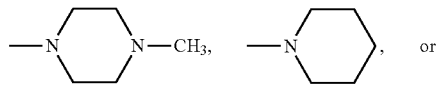

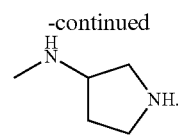

In some specific embodiments, —X-Q is

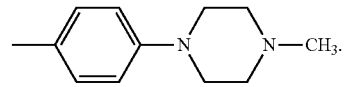

In other specific embodiments, —X-Q is

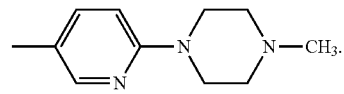

In still other specific embodiments, —X-Q is

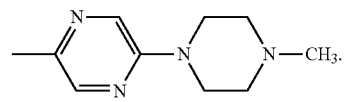

In still other specific embodiments, —X-Q is

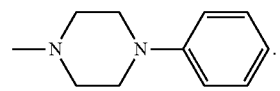

In these embodiments, Y is NH, S, or O and L is —(CH$_2$)$_m$— wherein m is 2-6. Other substituent groups are as described herein.

In some embodiments, $R_7$ is H, alkyl, heteroaryl or $NR_3R_4$, wherein the heteroaryl is optionally substituted by (C$_1$-C$_4$) alkyl and $R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle. In some specific embodiments, $R_7$ is $NR_3R_4$. In some specific embodiments, $R_3$ and $R_4$ are alkyl groups. In some specific embodiments, $R_7$ is $N(CH_3)_2$. In other specific embodiments, $R_7$ is morpholino group. In still other specific embodiments, $R_7$ is

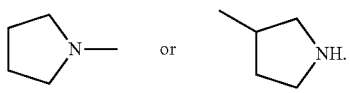

In other specific embodiments, $R_7$ is alkyl. In still other specific embodiments, $R_7$ is aryl or heteroaryl. Non-limiting examples of aryl and heteroaryl group for $R_7$ include

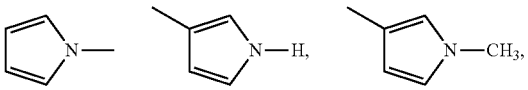

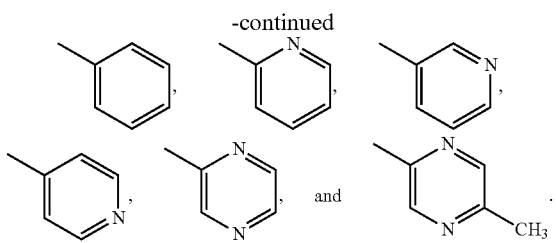

In some embodiments, $R_6$ is hydrogen, alkyl, alkenyl, $(CH_2)_rC(=O)O(C_1-C_4)$alkyl aryl, aralkyl, benzyl, heterocycle, $(CH_2)_pNR_bR_c$, or alkylheterocycle, wherein r is 0-4. In some specific embodiments, $R_6$ is benzyl or

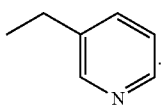

In other embodiments, $R_6$ is hydrogen,

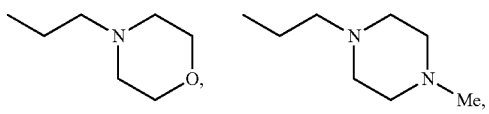

or alkyl.

In other embodiments, the compound of Formula (I) has the structure of Formula (II):

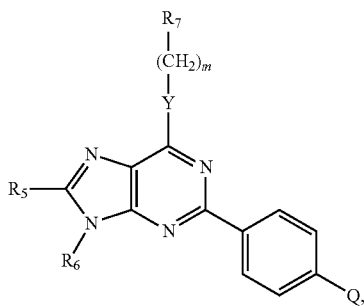

wherein

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl, wherein the heteroaryl is optionally substituted by $(C_1-C_4)$alkyl;

m is 2-6;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$alkyl, aryl, aralkyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle;

provided that when $R_5$ and $R_6$ are H or $C_1-C_3$ alkyl, then Q is not H.

In yet other embodiments, the compound of Formula (I) has the structure of Formula (III):

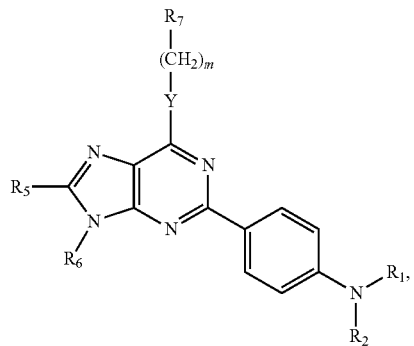

wherein $R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl, wherein the heteroaryl is optionally substituted by $(C_1-C_4)$alkyl;

m is 2-6;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$alkyl, aryl, aralkyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

In yet other embodiments, the compound of Formula (I) has the structure of Formula (IV):

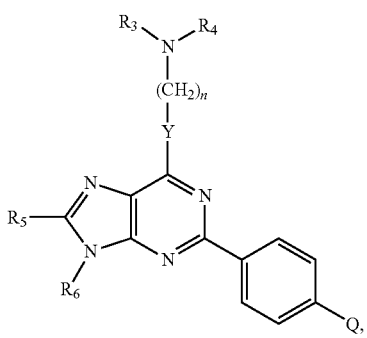

(IV)

wherein

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

n is 2-6;

$R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$alkyl, aryl, aralkyl, heterocycle, $(CH_2)_pNR_bR_c$, or alkylheterocycle, wherein r is 0-4;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle;

provided that when $R_5$ and $R_6$ are H or $C_1-C_3$ alkyl, then Q is not H.

In some embodiments, Q is H, $OR_1$, or $SR_1$. In some embodiments, $R_1$ and $R_2$ are each independently hydrogen, alkyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$ alkyl, phenyl, benzyl, $C(=O)R_{12}$, $(CH_2)_pOR_a$, and $(CH_2)_pNR_bR_c$, in which p is 2-4.

In some embodiments, $NR_1R_2$, $NR_3R_4$, and $NR_bR_c$ are each independently a heterocycle selected from in which $R_d$ is H, Me, Et, n-Pr, i-Pr, n-Bu, i-Bu, t-Bu, $CH_2CMe_3$, Ph, $CH_2Ph$, $C(=O)R_{12}$, $(CH_2)_pOR_a$, and $(CH_2)_pNR_bR_c$, wherein $R_{12}$ is alkyl, phenyl, or heterocycle; $R_a$, $R_b$ and $R_c$ are each independently hydrogen, or $(C_1-C_4)$ alkyl, or $R_b$ and $R_c$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4.

In one aspect, the present invention provides a compound selected from Examples 1 through 55 as described in Tables 1 and 2. The enumerated compounds in Tables 1 and 2 are representative and non-limiting purine compounds of the invention.

TABLE 1

Selected purine compositions, wherein $R_7 = NR_3R_4$

| Example No. | X | Q | Y | L | $R_3$ | $R_4$ | $R_5$ | $R_6$ |
|---|---|---|---|---|---|---|---|---|
| 1 | (4-methylphenyl) | (4-methylpiperazinyl)-$CH_3$ | NH | $-(CH_2)_2-$ | $NR_3R_4 =$ morpholinyl | | H | H |
| 2 | (6-methylpyridin-3-yl) | (4-methylpiperazinyl)-$CH_3$ | NH | $-(CH_2)_2-$ | $CH_3$ | $CH_3$ | H | H |

TABLE 1-continued
Selected purine compositions, wherein $R_7 = NR_3R_4$
| Example No. | X | Q | Y | L | $R_3$ | $R_4$ | $R_5$ | $R_6$ |
|---|---|---|---|---|---|---|---|---|
| 3 | 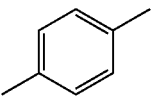 | 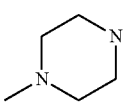 | NH | —(CH$_2$)$_2$— | CH$_3$ | CH$_3$ | H | CH$_3$ |
| 4 | 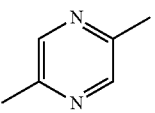 | 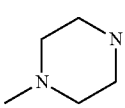 | NH | —(CH$_2$)$_2$— | CH$_3$ | CH$_3$ | CH$_3$ | H |
| 5 | —(CH$_2$)$_3$— | 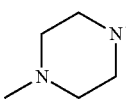 | S | —(CH$_2$)$_2$— | CH$_3$ | CH$_3$ | CH$_3$ | CH$_3$ |
| 6 | 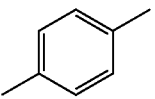 | 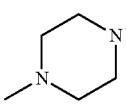 | NH | —(CH$_2$)$_2$— | CH$_3$ | CH$_3$ | 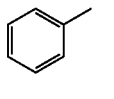 | CH$_3$ |
| 7 | 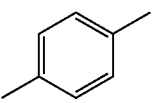 | 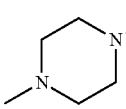 | O | —(CH$_2$)$_2$— | $NR_3R_4 =$ | 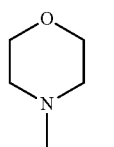 | OH | H |
| 8 | 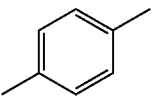 | 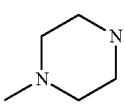 | NH | —(CH$_2$)$_2$— | $NR_3R_4 =$ | 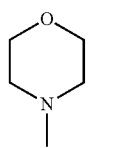 | SH | H |
| 9 | 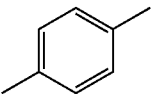 | 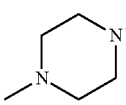 | NH | —(CH$_2$)$_2$— | $NR_3R_4 =$ | 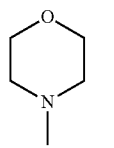 | Br | H |
| 10 | 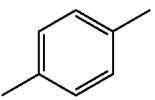 | 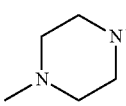 | NH | —(CH$_2$)$_2$— | $NR_3R_4 =$ | 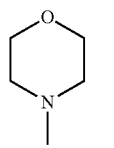 | Cl | H |
| 11 | —(CH$_2$)$_4$— | 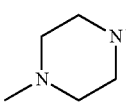 | NH | —(CH$_2$)$_2$— | $NR_3R_4 =$ | 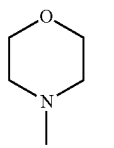 | SCH$_3$ | H |
| 12 | 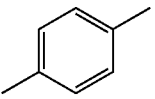 | 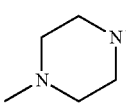 | NH | —(CH$_2$)$_2$— | $NR_3R_4 =$ | 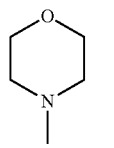 | SO$_2$CH$_3$ | H |

TABLE 1-continued

Selected purine compositions, wherein $R_7 = NR_3R_4$

| Example No. | X | Q | Y | L | $R_3$ | $R_4$ | $R_5$ | $R_6$ |
|---|---|---|---|---|---|---|---|---|
| 13 | 1,4-phenylene | 4-methylpiperazin-1-yl (N-CH₃) | NH | —(CH₂)₂— | $NR_3R_4 =$ | N-morpholinyl | OCH₃ | H |
| 14 | 1,4-phenylene | 4-methylpiperazin-1-yl (N-CH₃) | NH | —(CH₂)₂— | CH₃ | CH₃ | OH | benzyl (CH₂-C₆H₅) |
| 15 | 1,3-phenylene | 4-methylpiperazin-1-yl (N-CH₃) | NH | —(CH₂)₂— | $NR_3R_4 =$ | N-morpholinyl | H | 3-pyridylmethyl |
| 16 | 1,4-phenylene | 4-methylpiperazin-1-yl (N-CH₃) | NH | —(CH₂)₂— | $NR_3R_4 =$ | N-morpholinyl | CH₃ | H |
| 17 | 1,4-phenylene | 4-methylpiperazin-1-yl (N-CH₃) | NH | —(CH₂)₃— | $NR_3R_4 =$ | N-morpholinyl | H | CH₃ |
| 18 | 1,2-phenylene | —N(H)CH₂CH₂N(CH₃)₂ | NH | —(CH₂)₂— | $NR_3R_4 =$ | N-morpholinyl | H | H |
| 19 | 1,2-phenylene | —N(H)CH₂CH₂N(CH₃)₂ | NH | —(CH₂)₂— | $NR_3R_4 =$ | N-morpholinyl | H | CH₃ |
| 20 | 1,2-phenylene | —N(H)(CH₂)₃N(CH₃)₂ | NH | —(CH₂)₂— | CH₃ | CH₃ | H | H |
| 21 | 4-methylbenzyl (To Q) | 4-methylpiperazin-1-yl (N-CH₃) | NH | —(CH₂)₃— | CH₃ | CH₃ | H | H |
| 22 | 1,4-phenylene | 4-methylpiperazin-1-yl (N-CH₃) | NH | —(CH₂)₃— | CH₃ | CH₃ | CH₃ | CH₃ |
| 23 | 1,4-phenylene | 4-methylpiperazin-1-yl (N-CH₃) | NH | —(CH₂)₃— | CH₃ | CH₃ | H | CH₃ |

TABLE 1-continued

Selected purine compositions, wherein $R_7 = NR_3R_4$

| Example No. | X | Q | Y | L | $R_3$ | $R_4$ | $R_5$ | $R_6$ |
|---|---|---|---|---|---|---|---|---|
| 24 | 1,4-phenylene (p-tolyl linker) | 4-methylpiperazin-1-yl | S | —(CH$_2$)$_2$— | CH$_3$ | CH$_3$ | H | H |

TABLE 2

Additional Selected purine compositions of the Invention

| Example No. | X—Q | Y | L | $R_3$ | $R_4$ | $R_5$ | $R_6$ | $R_7$ |
|---|---|---|---|---|---|---|---|---|
| 25 | 4-(4-methylpiperazin-1-yl)-3-methylphenyl | O | —(CH$_2$)$_2$— | — | — | H | H | n-C$_4$H$_9$ |
| 26 | 4-(4-methylpiperazin-1-yl)-3-methylphenyl | S | —(CH$_2$)$_3$— | $NR_3R_4$ = 4-methylmorpholin-4-yl | | H | H | phenyl |
| 27 | 4-(4-methylpiperazin-1-yl)-3-methylphenyl | NH | —(CH$_2$)$_2$— | — | — | H | CH$_3$ | n-C$_4$H$_9$ |
| 28 | 4-(4-methylpiperazin-1-yl)-3-methylphenyl | NH | —(CH$_2$)$_5$— | CH$_3$ | CH$_3$ | H | H | $NR_3R_4$ |
| 29 | 4-(4-methylpiperazin-1-yl)-3-methylphenyl | NH | —(CH$_2$)$_2$— | CH$_3$ | CH$_3$ | H | CH$_3$ | $NR_3R_4$ |
| 30 | 3-methyl-4-(4-methylpiperazin-1-yl)phenyl | NH | —(CH$_2$)$_2$— | — | — | H | H | 2,5-dimethylpyrazinyl |
| 31 | 4-(4-methylpiperazin-1-yl)-3-methylphenyl | NH | —(CH$_2$)$_4$— | — | — | H | 3-ethylpyridinyl | n-C$_5$H$_{11}$ |
| 32 | 2-methyl-N-(2-(dimethylamino)ethyl)anilino | NH | —(CH$_2$)$_2$— | CH$_2$CH$_3$ | CH$_3$ | H | H | $NR_3R_4$ |

TABLE 2-continued

Additional Selected purine compositions of the Invention

| Example No. | X—Q | Y | L | $R_3$ | $R_4$ | $R_5$ | $R_6$ | $R_7$ |
|---|---|---|---|---|---|---|---|---|
| 33 | 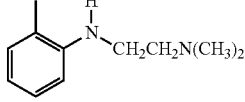 | NH | —(CH$_2$)$_2$— | CH$_3$ | CH$_3$ | CH$_3$ | CH$_3$ | NR$_3$R$_4$ |
| 34 | 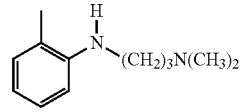 | S | —(CH$_2$)$_2$— | CH$_3$ | CH$_3$ | H | H | NR$_3$R$_4$ |
| 35 | 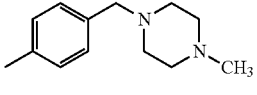 | NH | —(CH$_2$)$_3$— | CH$_3$ | CH$_3$ | H | H | NR$_3$R$_4$ |
| 36 | 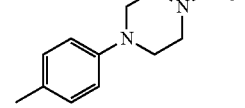 | NH | —(CH$_2$)$_4$— | NR$_3$R$_4$ = 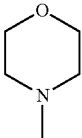 | | CH$_3$ | CH$_3$ | NR$_3$R$_4$ |
| 37 | 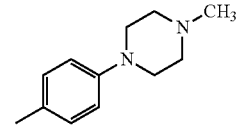 | NH | —(CH$_2$)$_4$— | — | — | CH$_3$ | CH$_3$ |  |
| 38 | 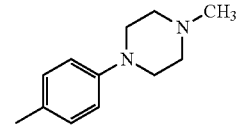 | S | —(CH$_2$)$_2$— | — | — | CH$_3$ | H |  |
| 39 | 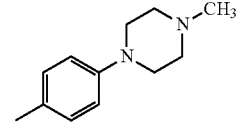 | N(CH$_3$) | —(CH$_2$)$_2$— | — | — | H | H | 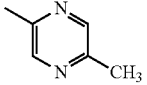 |
| 40 | 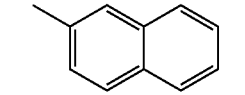 | NH | —(CH$_2$)$_2$— | CH$_3$ | CH$_3$ | 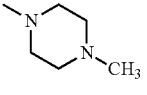 | H | NR$_3$R$_4$ |
| 41 | 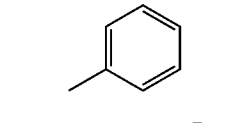 | NH | —(CH$_2$)$_2$— | CH$_3$ | CH$_3$ | 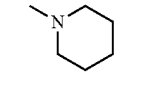 | H | NR$_3$R$_4$ |
| 42 | 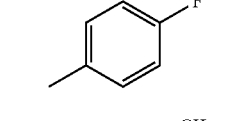 | NH | —(CH$_2$)$_2$— | CH$_3$ | CH$_3$ | 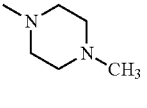 | H | NR$_3$R$_4$ |
| 43 | 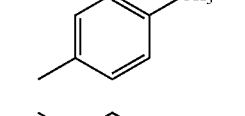 | NH | —(CH$_2$)$_2$— | CH$_3$ | CH$_3$ | 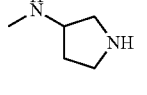 | H | NR$_3$R$_4$ |
| 44 | 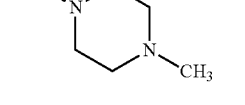 | NH | —(CH$_2$)$_2$— | CH$_3$ | CH$_3$ | H | H | NR$_3$R$_4$ |

TABLE 2-continued

Additional Selected purine compositions of the Invention

| Example No. | X—Q | Y | L | $R_3$ | $R_4$ | $R_5$ | $R_6$ | $R_7$ |
|---|---|---|---|---|---|---|---|---|
| 45 | 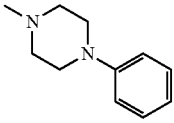 | NH | —(CH$_2$)$_2$— | CH$_3$ | CH$_3$ | H | H | NR$_3$R$_4$ |
| 46 | 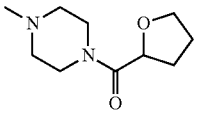 | NH | —(CH$_2$)$_2$— | NR$_3$R$_4$ = | 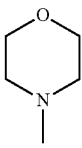 | H | H | NR$_3$R$_4$ |
| 47 | 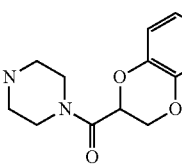 | NH | —(CH$_2$)$_2$— | CH$_3$ | H | H | H | NR$_3$R$_4$ |
| 48 | 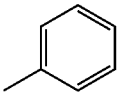 | NCH$_3$ | —(CH$_2$)$_3$— | CH$_2$CH$_3$ | CH$_2$CH$_3$ | 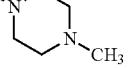 | H | NR$_3$R$_4$ |
| 49 | 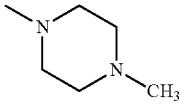 | NH | —(CH$_2$)$_2$— | 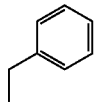 | H | H | H | NR$_3$R$_4$ |
| 50 | 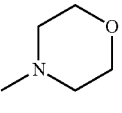 | NH | —(CH$_2$)$_3$— | 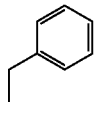 | H | H | H | NR$_3$R$_4$ |
| 51 | 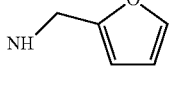 | NH | —(CH$_2$)$_2$— |  | H | H | H | NR$_3$R$_4$ |
| 52 | 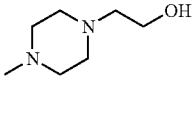 | NH | —(CH$_2$)$_2$— | 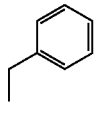 | CH$_3$ | H | H | NR$_3$R$_4$ |
| 53 | 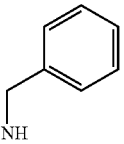 | NCH$_3$ | —(CH$_2$)$_2$— | CH$_3$ | H | H | H | NR$_3$R$_4$ |
| 54 | 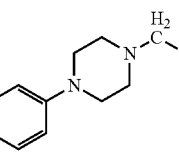 | NH | —(CH$_2$)$_2$— | NR$_3$R$_4$ = | 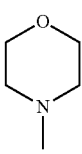 | H | H | NR$_3$R$_4$ |

TABLE 2-continued
Additional Selected purine compositions of the Invention
| Example No. | X—Q | Y | L | R₃ | R₄ | R₅ | R₆ | R₇ |
|---|---|---|---|---|---|---|---|---|
| 55 | 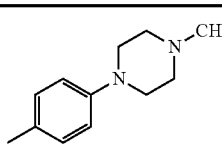 | NH | —(CH₂)₂— | NR₃R₄ = | 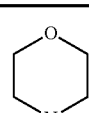 | H | 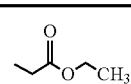 | NR₃R₄ |
| 56 | 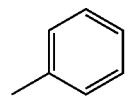 | NH | —(CH₂)₂— | NR₃R₄ = | 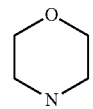 | OH | 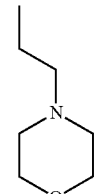 | NR₃R₄ |
| 57 | 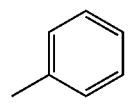 | NH | —(CH₂)₂— | NR₃R₄ = | 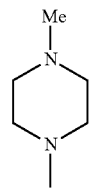 | OH | 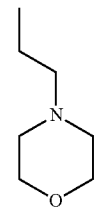 | NR₃R₄ |
| 58 | 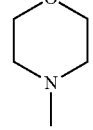 | NH | —(CH₂)₂— | NR₃R₄ = | 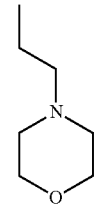 | OH | 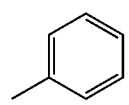 | NR₃R₄ |
| 59 | 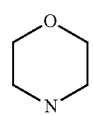 | NH | —(CH₂)₂— | NR₃R₄ = | 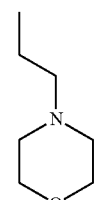 | H | 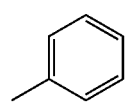 | NR₃R₄ |
| 60 | 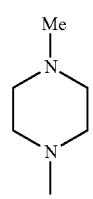 | NH | —(CH₂)₂— | NR₃R₄ = | 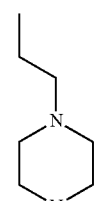 | H | 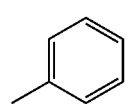 | NR₃R₄ |
| 61 | 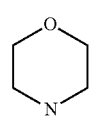 | NH | —(CH₂)₂— | NR₃R₄ = | 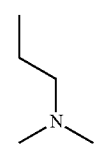 | H | | NR₃R₄ |

TABLE 2-continued

Additional Selected purine compositions of the Invention

| Example No. | X—Q | Y | L | $R_3$ | $R_4$ | $R_5$ | $R_6$ | $R_7$ |
|---|---|---|---|---|---|---|---|---|
| 62 | 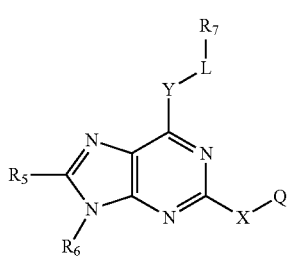 | NH | —$(CH_2)_2$— | $NR_3R_4 =$ | Me (N-methylpiperazinyl) | H | (morpholinoethyl) | $NR_3R_4$ |
| 63 | 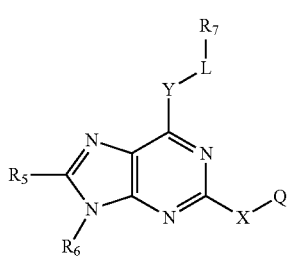 | NH | —$(CH_2)_2$— | $NR_3R_4 =$ | Me (N-methylpiperazinyl) | OH | (morpholinoethyl) | $NR_3R_4$ |

In another aspect, the present invention provides a pharmaceutical composition comprising at least one compound of formulae I, II, III, and IV as described herein and a pharmaceutically-acceptable carrier or diluent.

In yet another aspect, the present invention provides a method for treating an autoimmune disease in a mammalian species in need thereof, the method comprising administering to the mammalian species a therapeutically effective amount of at least one compound of Formula I, $$\text{(I)}$$

wherein

X is absent or is an alkyl, alkylamino, cycloalkyl, aryl, or heterocycle;

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl or $NR_3R_4$, wherein the heteroaryl is optionally substituted by $(C_1-C_4)$alkyl;

$R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

L is alkyl or alkenyl containing from 2 to 10 carbon atoms;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$alkyl, aryl, aralkyl, benzyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$ and $R_c$ is independently hydrogen, alkyl, cycloalkyl, heterocycle, aryl, or said $R_b$ and $R_c$ together with the nitrogen atom to which they are bonded optionally form a heterocycle.

In yet another aspect, the present invention provides a method for treating an autoimmune disease in a mammalian species in need thereof, the method comprising administering to the mammalian species a therapeutically effective amount of at least one compound of Formula II,

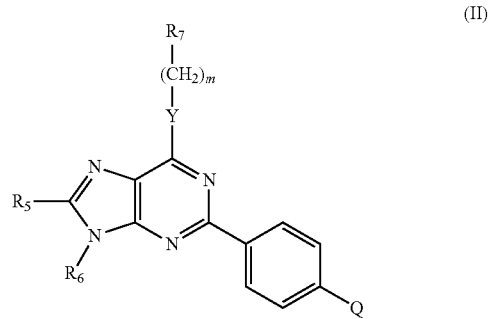

wherein

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl, wherein the heteroaryl is optionally substituted by $(C_1-C_4)$alkyl;

m is 2-6;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$alkyl, aryl, aralkyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

In yet another aspect, the present invention provides a method for treating an autoimmune disease in a mammalian species in need thereof, the method comprising administering to the mammalian species a therapeutically effective amount of at least one compound of Formula III,

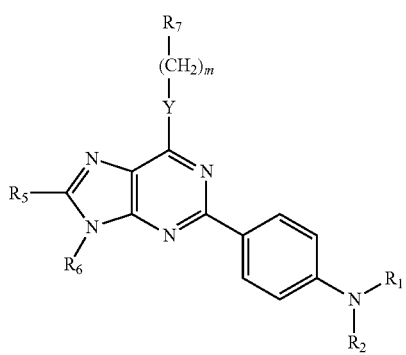

(III)

wherein $R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl, wherein the heteroaryl is optionally substituted by $(C_1-C_4)$alkyl;

m is 2-6;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$alkyl, aryl, aralkyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

In yet another aspect, the present invention provides a method for treating an autoimmune disease in a mammalian species in need thereof, the method comprising administering to the mammalian species a therapeutically effective amount of at least one compound of Formula IV,

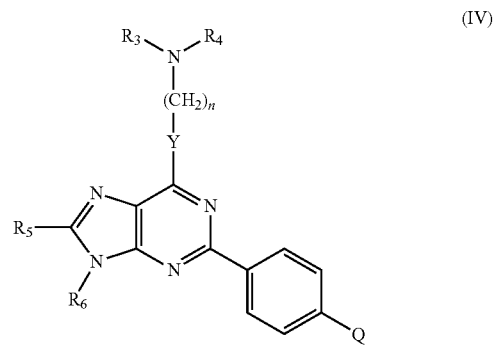

(IV)

wherein

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

n is 2-6;

$R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$alkyl, aryl, aralkyl, heterocycle, $(CH_2)_pNR_bR_c$, or alkylheterocycle, wherein r is 0-4;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

In certain embodiments, the purine composition is in the form a hydrate or pharmaceutically acceptable salt. The purine composition can be administered to the subject by any suitable route of administration, including, without limitation, oral and parenteral. Parenteral routes of administration are as described above with respect to substituted 4-primary amino purines.

In certain embodiments, the autoimmune disease is selected from cutaneous and systemic lupus erythematosus, insulin-dependent diabetes mellitus, rheumatoid arthritis, multiple sclerosis, atherosclerosis, psoriasis, psoriatic arthritis, inflammatory bowel disease, ankylosing spondylitis, autoimmune hemolytic anemia, Behget's syndrome, Goodpasture's syndrome, Graves' disease, Guillain-Barre syndrome, Hashimoto's thyroiditis, idiopathic thrombocytopenia, io myasthenia gravis, pernicious anemia, polyarteritis nodosa, polymyositis/dermatomyositis, primary biliary sclerosis, sarcoidosis, sclerosing cholangitis, Sjogren's syndrome, systemic sclerosis (scleroderma and CREST syndrome), Takayasu's arteritis, temporal arteritis, and Wegener's granulomatosis.

In some embodiments, the autoimmune disease is selected from the group consisting of systemic lupus erythematosus, rheumatoid arthritis, psoriasis, inflammatory bowel disease, Sjogren's syndrome, polymyositis, vasculitis, Wegener's granulomatosis, sarcoidosis, ankylosing spondylitis, Reiter's syndrome, psoriatic arthritis, and Behyet's syndrome. In one particular embodiment, the autoimmune disease is systemic lupus erythematosus. In another particular embodiment, the autoimmune disease is rheumatoid arthritis. In one particular embodiment the autoimmune disease is psoriasis. In yet another particular embodiment, the autoimmune disease is Sjogren's syndrome. In one embodiment, the subject is a human. In one embodiment the autoimmune disorder is an immune complex associated disease, as described above.

In yet another aspect, the present invention provides a method of inhibiting TLR-mediated immunostimulation in a mammalian species in need thereof, comprising administering to the mammalian species a therapeutically effective amount of at least one compound of Formula I,

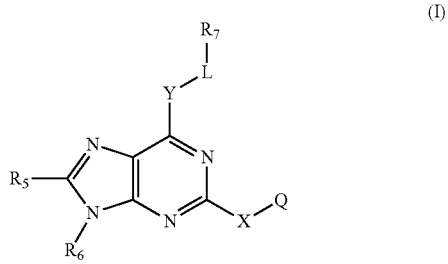

(I)

wherein

X is absent or is an alkyl, alkylamino, cycloalkyl, aryl, or heterocycle;

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1$-$C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl or $NR_3R_4$, wherein the heteroaryl is optionally substituted by $(C_1$-$C_4)$alkyl;

$R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

L is alkyl or alkenyl containing from 2 to 10 carbon atoms;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1$-$C_4)$ alkyl, aryl, aralkyl, benzyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

In yet another aspect, the present invention provides a method of inhibiting TLR-mediated immunostimulation in a mammalian species in need thereof, comprising administering to the mammalian species a therapeutically effective amount of at least one compound of Formula II,

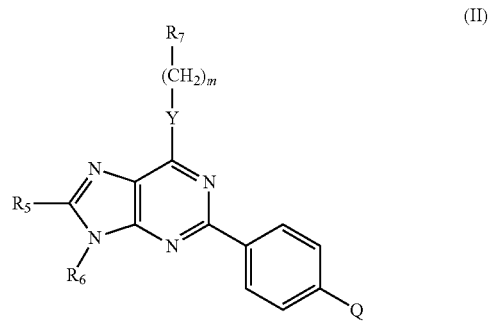

(II)

wherein

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1$-$C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl, wherein the heteroaryl is optionally substituted by $(C_1-C_4)$alkyl;

m is 2-6;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$alkyl, aryl, aralkyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

In yet another aspect, the present invention provides a method of inhibiting TLR-mediated immunostimulatory signaling, comprising contacting a cell expressing a TLR with an effective amount of at least one compound of Formula III,

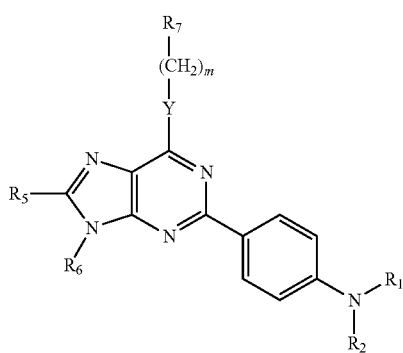

(III)

wherein $R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl, wherein the heteroaryl is optionally substituted by $(C_1-C_4)$alkyl;

m is 2-6;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$alkyl, aryl, aralkyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

In yet another aspect, the present invention provides a method of inhibiting TLR-mediated immunostimulatory signaling, comprising contacting a cell expressing a TLR with an effective amount of at least one compound of Formula IV,

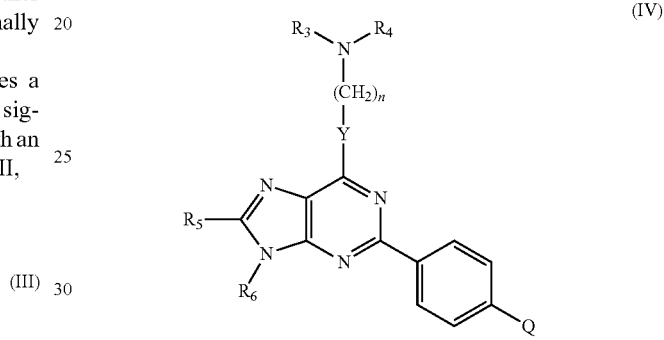

(IV)

wherein

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

n is 2-6;

$R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$alkyl, aryl, aralkyl, heterocycle, $(CH_2)_pNR_bR_c$, or alkylheterocycle, wherein r is 0-4;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

In some embodiments, the method of affecting TLR-mediated immunostimulation in a subject comprises administering to a subject having or at risk of developing TLR-mediated immunostimulation an effective amount of a compound of Formulae I-IV, as provided herein, to inhibit TLR-mediated immunostimulation in the subject.

In yet another aspect, the present invention provides a method of inhibiting TLR-mediated immunostimulatory signaling, comprising contacting a cell expressing a TLR with an effective amount of at least one compound of Formula I,

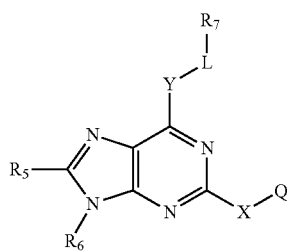

(I)

wherein

X is absent or is an alkyl, alkylamino, cycloalkyl, aryl, or heterocycle;

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl or $NR_3R_4$, wherein the heteroaryl is optionally substituted by $(C_1-C_4)$alkyl;

$R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

L is alkyl or alkenyl containing from 2 to 10 carbon atoms;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$alkyl, aryl, aralkyl, benzyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

In yet another aspect, the present invention provides a method of inhibiting TLR-mediated immunostimulatory signaling, comprising contacting a cell expressing a TLR with an effective amount of at least one compound of Formula II,

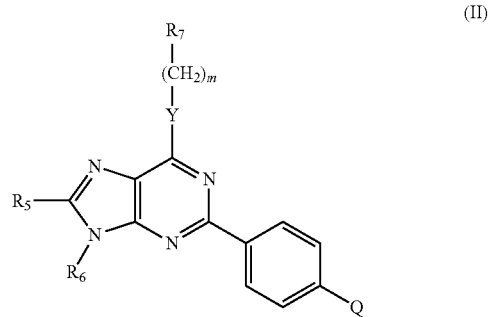

(II)

wherein

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl, wherein the heteroaryl is optionally substituted by $(C_1-C_4)$alkyl;

m is 2-6;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$alkyl, aryl, aralkyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

In yet another aspect, the present invention provides a method of inhibiting TLR-mediated immunostimulatory signaling, comprising contacting a cell expressing a TLR with an effective amount of at least one compound of Formula III,

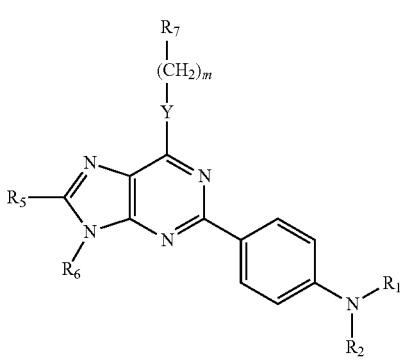

(III)

wherein $R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

$R_7$ is H, alkyl, heteroaryl, wherein the heteroaryl is optionally substituted by $(C_1-C_4)$alkyl;

m is 2-6;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$alkyl, aryl, aralkyl, heterocycle, $(CH_2)_pNR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

In yet another aspect, the present invention provides a method of inhibiting TLR-mediated immunostimulatory signaling, comprising contacting a cell expressing a TLR with an effective amount of at least one compound of Formula IV,

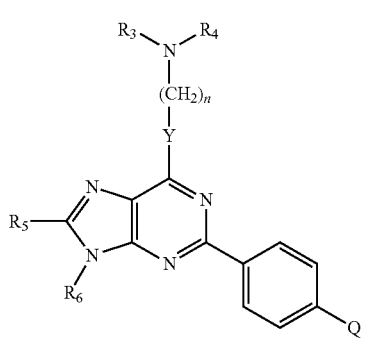

(IV)

wherein

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

n is 2-6;

$R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is hydrogen, alkyl, alkenyl, $(CH_2)_rC(=O)O(C_1-C_4)$alkyl, aryl, aralkyl, heterocycle, $(CH_2)_pNR_bR_c$, or alkylheterocycle, wherein r is 0-4;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

In some embodiments, the method of inhibiting TLR-mediated immunostimulatory signaling comprises contacting a cell expressing a TLR with an effective amount of a compound of Formulae I-IV, as provided above, to inhibit TLR-mediated immunostimulatory signaling in response to a ligand for the TLR.

In some embodiments, the method of inhibiting TLR-mediated immunostimulatory signaling comprises contacting an immune cell expressing a functional TLR with (a) an effective amount of a TLR signal agonist to stimulate signaling by the TLR in absence of a purine composition, and (b) an effective amount of a purine composition having structural Formula I, II, III, or IV, as described herein, to inhibit signaling by the TLR in response to the TLR signal agonist compared with the signaling by the TLR in response to the TLR signal agonist in absence of the purine composition.

In some specific embodiments, the purine composition used for inhibiting TLR-mediated immunostimulatory signaling has a structure of Formula IV. In some specific embodiments, the purine composition is in the form a hydrate or pharmaceutically acceptable salt. In some specific embodiments, the method for inhibiting TLR-mediated immunostimulatory signaling is performed in vitro or in vivo.

In some embodiments, the TLR is TLR9 and the TLR signal agonist is a TLR9 signal agonist. In these embodiments, the method is a method of inhibiting intracellular signaling by TLR9 in response to a TLR9 signal agonist. The TLR signal agonist in one embodiment is CpG DNA, which can be an oligodeoxynucleotide (ODN). In some embodiments, CpG ODN is ODN 2006. In other embodiments, CpG ODN belongs to any class of CpG ODN, including A-class (e.g., ODN 2216), B-class (e.g., ODN 2006), or C-class (e.g., ODN 2395).

In some embodiments, In one embodiment the TLR signal agonist is an immune complex that includes a nucleic acid.

In some embodiments, the method as described herein are useful for altering TLR-mediated signaling. The methods are used to alter TLR mediated signaling in response to a suitable TLR ligand or TLR signaling agonist. For example, the methods can be used to treat any of variety of conditions involving autoimmunity, inflammation, allergy, asthma, graft rejection, graft-versus host disease (GvHD), infection, sepsis, cancer, and immunodeficiency. Generally, methods useful in the treatment of conditions involving autoimmunity, inflammation, allergy, asthma, graft rejection, and GvHD will employ small molecules that inhibit TLR-mediated signaling in response to a suitable TLR ligand or TLR signaling agonist. Generally, methods useful in the treatment of conditions involving infection, cancer, and immunodeficiency will employ small molecules that augment TLR-mediated signaling in response to a suitable TLR ligand. In some embodiments, the methods are used to inhibit or promote TLR-mediated signaling in response to a TLR ligand or TLR signaling agonist. In some embodiments, the methods are used to inhibit TLR-mediated immunostimulatory signaling in response to a TLR ligand or TLR signaling agonist. In some embodiments, the methods are used to inhibit or promote TLR-mediated immunostimulation in a subject. In some embodiments, the methods are used to inhibit TLR-mediated immunostimulation in a subject. In some embodiments, the methods are used to inhibit an immunostimulatory nucleic acid-associated response in a subject.

In some embodiments, the method useful for altering TLR-mediated signaling uses small molecule compositions of compounds of Formulae I-IV. The compositions of the invention are used to alter TLR-mediated signaling in response to a suitable TLR ligand or TLR signaling agonist. For example, the small molecules can be used in methods to treat any of a variety of conditions involving autoimmunity, inflammation, allergy, asthma, graft rejection, GvHD, infection, sepsis, cancer, and immunodeficiency. Generally, methods useful in the treatment of conditions involving autoimmunity, inflammation, allergy, asthma, graft rejection, and GvHD will employ small molecules that inhibit TLR-mediated signaling in response to a suitable TLR ligand or TLR signaling agonist. Generally, methods useful in the treatment of conditions involving infection, cancer, and immunodeficiency will employ small molecules that augment TLR-mediated signaling in response to a suitable TLR ligand. In some instances the molecules can be used in a method to inhibit or promote TLR-mediated signaling in response to a TLR ligand or TLR signaling agonist. In some instances the small molecules can be used in a method to inhibit TLR-mediated immunostimulatory signaling in response to a TLR ligand or TLR signaling agonist. In some embodiments, the small molecules are used in a method to inhibit or promote TLR-mediated immunostimulation in a subject. In some embodiments, the small molecules are used in a method to inhibit TLR-mediated immunostimulation in a subject. In some embodiments, the small molecules are used to inhibit an immunostimulatory nucleic acid-associated response in a subject.

Furthermore, the methods as described herein can be combined with administration of additional agents to achieve synergistic effect on TLR-mediated immunostimulation. More specifically, whereas the agents described herein have been discovered to affect TLRs directly and thus directly affect TLR-bearing cells, e.g., antigen-presenting cells (APCs), such agents can be used in conjunction with additional agents which affect non-APC immune cells, e.g., T lymphocytes (T cells). Such an approach effectively introduces an immunomodulatory intervention at two levels: innate immunity and acquired immunity. Since innate immunity is believed to initiate and support acquired immunity, the combination intervention is synergistic.

In yet another aspect, a method of inhibiting an immunostimulatory nucleic acid-associated response in a subject is provided. The method comprises administering to a subject in need of such treatment an effective amount of a compound of Formulae I-IV, as provided above, to inhibit an immunostimulatory nucleic acid-associated response in the subject.

In some embodiments, the subject being treated with the purine compounds as described herein has symptoms indicating a immune system disease. In other embodiments, the subject being treated with the purine compounds as described herein is free of any symptoms indicating a immune system disease.

In some embodiments, the TLR is TLR9. In some specific embodiments, the ligand for the TLR is an immunostimulatory nucleic acid. In other specific embodiments, the immunostimulatory nucleic acid is a CpG nucleic acid. In still other specific embodiments, the immunostimulatory nucleic acid a DNA containing immune complex.

In some embodiments, the TLR is TLR8. In some specific embodiments, the ligand for the TLR is a natural ligand for TLR8. In other specific embodiments, the ligand for the TLR is RNA. In still other specific embodiments, the ligand for the TLR is an immunostimulatory nucleic acid. In still other specific embodiments, the immunostimulatory nucleic acid is an RNA containing immune complex. In still other specific embodiments, the ligand for the TLR is an immunostimulatory imidazoquinoline. In still other specific embodiments, the ligand for the TLR is resiquimod (R848).

In some embodiments, the TLR is TLR7. In some specific embodiments, the ligand for the TLR is a natural ligand for TLR7. In other specific embodiments, the ligand for the TLR is an immunostimulatory nucleic acid. In one embodiment the ligand for the TLR is an RNA. In still other specific embodiments, the immunostimulatory nucleic acid is an RNA containing immune complex. In still other specific embodiments, the ligand for the TLR is an immunostimulatory imidazoquinoline. In still other specific embodiments, the ligand for the TLR is R848.

In some embodiments, the TLR is TLR3. In some specific embodiments, the ligand for the TLR is a double stranded RNA. In other specific embodiments, the ligand for the TLR is the immune complex as described herein. In still other specific embodiments, the ligand for the TLR is poly(I:C). In still other specific embodiments, the TLR is TLR9 and the TLR signal agonist is a TLR9 signal agonist. In still other specific embodiments, the TLR signal agonist is CpG DNA, which can be an oligodeoxynucleotide (ODN).

In some embodiments, the TLR signal agonist is an immune complex comprising a nucleic acid.

In yet another aspect, a method for inhibiting an immune response to an antigenic substance is provided. The method comprises contacting an immune cell expressing a functional Toll-like receptor with:

(a) an effective amount of an antigenic substance to stimulate an immune response to the antigenic substance in the absence of a purine composition, and (b) an effective amount of a purine composition having structural Formulae I-IV, as defined above, to inhibit an immune response to the antigenic substance compared with the immune response to the antigenic substance in absence of the purine composition.

In some embodiments, the immune response is an innate immune response. In other embodiments, the immune response includes an adaptive immune response. In some specific embodiments, the purine composition is in the form a hydrate or pharmaceutically acceptable salt. In some specific embodiments, the method for inhibiting an immune response to an antigenic substance is performed in vitro or in vivo.

In some embodiments, the antigenic substance is an allergen. In other embodiments, the antigenic substance is an antigen that is or is derived from a microbial agent, including a bacterium, a virus, a fungus, or a parasite. In still other embodiments, the antigenic substance is a cancer antigen.

In certain embodiments, the functional TLR is naturally expressed by a cell. Non-limiting examples of cells expressing TLR include RPMI 8226 cell line.

In one embodiment, the cell naturally expresses functional TLR and is an isolated cell from human multiple myeloma cell line RPMI 8226 (ATCC CCL-155; American Type Culture Collection (ATCC), Manassas, Va.). This cell line was established from the peripheral blood of a 61 year old man at the time of diagnosis of multiple myeloma (IgG lambda type). Matsuoka Y et al. (1967) *Proc Soc Exp Biol Med* 125:1246-50. RPMI 8226 was previously reported as responsive to CpG nucleic acids as evidenced by the induction of IL-6 protein and IL-12p40 mRNA. Takeshita F et al. (2000) *Eur J Immunol* 30:108-16; Takeshita F et al. (2000) *Eur J Immunol* 30:1967-76. Takeshita et al. used the cell line solely to study promoter constructs in order to identify transcription factor binding sites important for CpG nucleic acid signaling. It is now known that RPMI 8226 cells secrete a number of other chemokines and cytokines including IL-8, IL-10 and IP-10 in response to immunostimulatory nucleic acids. Because this cell line expresses TLR9, through which immunostimulatory nucleic acids such as for example CpG nucleic acids mediate their effects, it is a suitable cell line for use in the methods of the invention relating to CpG nucleic acids as reference and test compounds, as well as to other TLR9 ligands.

Similar to peripheral blood mononuclear cells (PBMCs), the RPMI 8226 cell line has been observed to upregulate its cell surface expression of markers such as CD71, CD86 and HLA-DR in response to CpG nucleic acid exposure. This has been observed by flow cytometric analysis of the cell line. Accordingly, the methods provided herein can be structured to use appropriately selected cell surface marker expression as a readout, in addition to or in place of chemokine or cytokine production or other readouts described elsewhere herein.

The RPMI 8226 cell line has also been found to respond to certain small molecules including imidazoquinoline compounds. For example, incubation of RPMI 8226 cells with the imidazoquinoline compound R848 (resiquimod) induces IL-8, IL-10, and IP-10 production. It has recently been reported that R848 mediates its immunostimulatory effects through TLR7 and TLR8. The ability of RPMI 8226 to respond to R848 suggests that the RPMI 8226 cell line also expresses TLR7, as previously reported for normal human B cells.

The RPMI cell line can be used in unmodified form or in a modified form. In one embodiment, the RPMI 8226 cell is transfected with a reporter construct. Preferably, the cell is stably transfected with the reporter construct. The reporter construct generally includes a promoter, a coding sequence and a polyadenylation signal. The coding sequence can include a reporter sequence selected from the group consisting of an enzyme (e.g., luciferase, alkaline phosphatase, beta-galactosidase, chloramphenicol acetyltransferase (CAT), secreted alkaline phosphatase, etc.), a bioluminescence marker (e.g., green fluorescent protein (GFP, U.S. Pat. No. 5,491,084), etc.), a surface-expressed molecule (e.g., CD25), a secreted molecule (e.g., IL-8, IL-12 p40, TNF-α, etc.), and other detectable protein products known to those of skill in the art. Preferably, the coding sequence encodes a protein having a level or an activity that is quantifiable.

In certain embodiments, the functional TLR is artificially expressed (including over-expressed) by a cell, for example by introduction into the cell of an expression vector bearing a coding sequence for the functional TLR wherein the coding sequence is operably linked to a gene expression sequence. As used herein, a coding sequence and the gene expression sequence are said to be operably linked when they are covalently linked in such a way as to place the expression or transcription and/or translation of the coding sequence under the influence or control of the gene expression sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding sequence if the gene expression sequence were capable of effecting transcription of that coding sequence such that the resulting transcript is translated into the desired protein or polypeptide.

In some embodiments, a coding sequence refers to a nucleic acid sequence coding for a functional TLR. In some embodiments, a coding sequence refers to a nucleic acid sequence coding for a reporter.

A cell that artificially expresses a functional TLR can be a cell that does not express the functional TLR but for the TLR expression vector. For example, human 293 fibroblasts (ATCC CRL-1573) do not express TLR3, TLR7, TLR8, or TLR9. As described in the examples below, such cells can be transiently or stably transfected with suitable expression vector (or vectors) so as to yield cells that do express TLR3, TLR7, TLR8, TLR9, or any combination thereof. Alternatively, a cell that artificially expresses a functional TLR can be a cell that expresses the functional TLR at a significantly higher level with the TLR expression vector than it does without the TLR expression vector.

For use in the methods of the instant invention, a cell that artificially expresses a functional TLR is preferably a stably transfected cell that expresses the functional TLR. Such a cell can also be stably transfected with a suitable reporter construct.

Assays for Effectiveness

The methods of the invention can be assessed using any of a number of possible readout systems based upon a TLR/IL-1R signal transduction pathway. In some embodiments, the readout for the method is based on the use of native genes or, alternatively, transfected or otherwise artificially introduced reporter gene constructs which are responsive to the TLR/IL-1R signal transduction pathway involving MyD88, TRAF, p38, and/or ERK. Häcker H et al. (1999) *EMBO J* 18:6973-82. These pathways activate kinases including κB kinase complex and c-Jun N-terminal kinases. Thus reporter genes and reporter gene constructs particularly useful for the assays include, e.g., a reporter gene operatively linked to a promoter sensitive to NF-κB. Examples of such promoters include, without limitation, those for NF-κB, IL-1β, IL-6, IL-8, IL-12 p40, IP-10, CD80, CD86, and TNF-α. The reporter gene operatively linked to the TLR-sensitive promoter can include, without limitation, an enzyme (e.g., luciferase, alkaline phosphatase, β-galactosidase, chloramphenicol acetyltransferase (CAT), etc.), a bioluminescence marker (e.g., green-fluorescent protein (GFP, e.g., U.S. Pat. No. 5,491,084), blue fluorescent protein (BFP, e.g., U.S. Pat. No. 6,486,382), etc.), a surface-expressed molecule (e.g., CD25, CD80, CD86), and a secreted molecule (e.g., IL-1, IL-6, IL-8, IL-12 p40, TNF-α). In certain embodiments the reporter is selected from IL-8, TNF-α, NF-κB-luciferase (NF-κB-luc; Häcker H et al. (1999) EMBO J 18:6973-82), IL-12 p40-luc (Murphy T L et al. (1995) Mol Cell Biol 15:5258-67), and TNF-luc (Häcker H et al. (1999) EMBO J 18:6973-82). In assays relying on enzyme activity readout, substrate can be supplied as part of the assay, and detection can involve measurement of chemiluminescence, fluorescence, color development, incorporation of radioactive label, drug resistance, or other marker of enzyme activity. For assays relying on surface expression of a molecule, detection can be accomplished using flow cytometry (FACS) analysis or functional assays. Secreted molecules can be assayed using enzyme-linked immunosorbent assay (ELISA) or bioassays. Many of these and other suitable readout systems are well known in the art and are commercially available.

Reporter Constructs

A cell expressing a functional TLR and useful for the methods of the invention has, in some embodiments, an expression vector including an isolated nucleic acid which encodes a reporter construct useful for detecting TLR signaling. The expression vector including an isolated nucleic acid which encodes a reporter construct useful for detecting TLR signaling can include a reporter gene under control of a promoter response element (enhancer element). In some embodiments, the promoter response element is associated with a minimal promoter responsive to a transcription factor believed by the applicant to be activated as a consequence of TLR signaling. Examples of such minimal promoters include, without limitation, promoters for the following genes: AP-1, NF-κB, ATF2, IRF3, and IRF7. These minimal promoters contain corresponding promoter response elements sensitive to AP-1, NF-κB, ATF2, IRF3, and IRF7, respectively. In other embodiments the expression vector including an isolated nucleic acid which encodes a reporter construct useful for detecting TLR signaling can include a gene under control of a promoter response element selected from response elements sensitive to IL-6, IL-8, IL-12 p40 subunit, a type I IFN, RANTES, TNF, IP-10, I-TAC, and interferon-stimulated response element (ISRE). The promoter response element generally will be present in multiple copies, e.g., as tandem repeats. For example, in one reporter construct, coding sequence for luciferase is under control of an upstream 6× tandem repeat of NF-κB response element. In some embodiments, an ISRE-luciferase reporter construct useful in the invention is available from Stratagene (catalog no. 219092) and includes a 5×ISRE tandem repeat joined to a TATA box upstream of a luciferase reporter gene. As described herein, the reporter itself can be any gene product suitable for detection by methods recognized in the art. Such methods for detection can include, for example, measurement of spontaneous or stimulated light emission, enzyme activity, expression of a soluble molecule, expression of a cell surface molecule, etc.

Readouts typically involve usual elements of Toll/IL-1R signaling, e.g., MyD88, TRAF, and IRAK molecules, although in the case of TLR3 the role of MyD88 is less clear than for other TLR family members. As described herein, such responses include the induction of a gene under control of a specific promoter such as a NF-κB promoter, increases in particular cytokine levels, increases in particular chemokine levels, etc. The gene under the control of the NF-κB promoter can be a gene which naturally includes an NF-κB promoter or it can be a gene in a construct in which an NF-κB promoter has been inserted. Genes and constructs which include the NF-κB promoter include but are not limited to IL-8, IL-12 p40, NF-κB-luc, IL-12 p40-luc, and TNF-luc.

Increases in cytokine levels can result from increased production, increased stability, increased secretion, or any combination of the forgoing, of the cytokine in response to the TLR-mediated signaling. Cytokines generally include, without limitation, IL-1, IL-2, IL-3, IL-4, IL-5, IL-6, IL-7, IL-10, IL-11, IL-12, IL-13, IL-15, IL-18, IFN-α, IFN-β, IFN-γ, TNF-α, GM-CSF, G-CSF, M-CSF. Th1 cytokines include but are not limited to IL-2, IFN-γ, and IL-12. Th2 cytokines include but are not limited to IL-4, IL-5, and IL-10.

Increases in chemokine levels can result from increased production, increased stability, increased secretion, or any combination of the forgoing, of the chemokine in response to the TLR-mediated signaling. Chemokines of particular significance in the invention include but are not limited to CCL5 (RANTES), CXCL9 (Mig), CXCL10 (IP-10), and CXCL11 (I-TAC), IL-8, and MCP-1.

ABBREVIATIONS

ACN Acetonitrile
EA Ethyl acetate
DMF Dimethyl formamide
PE Petroleum ether
DCM Dichloromethane
THF Tetrahydrofuran
HOBT 1-Hydroxybenzotriazole
EDCI 1-Ethyl-3-(3-dimethylaminopropyl)carbodiimide
HBTU 2-(1H-Benzotriazole-1-yl)-1,1,3,3-tetramethyluronium hexafluorophosphate
HATU N-[(dimethylamino)(3H-1,2,3-triazolelo(4,4-b)pyridin-3-yloxy)methylene]-N-methylmethaneaminium hexafluorophosphate
PyBOP 1H-Benzotriazol-1-yloxytripyrrolidinophosphonium hexafluorophosphate
BOPCl Bis(2-oxo-3-oxazolidinyl)phosphinic chloride
BOP Benzotriazol-1-yloxytris(diethylamino)phosphonium hexafluorophosphate
TEA Triethylamine
DIPEA Diisopropylethylamine
DMAP 4-Dimethylaminopyridine
PCC Pyridinium chlorochromate
PDC Pyridinium dichromate
NBS N-bromosuccinimide
NCS N-chlorosuccinimide
NIS N-iodosuccinimide
9-BBN 9-Borabicyclo[3.3.1]nonane
TsOH p-Toluenesulfonic acid
TFA Trifluoroacetamide
CDI Carbonyldiimidazole Methods of Preparation Following are general synthetic schemes for manufacturing compounds of the present invention. These schemes are illustrative and are not meant to limit the possible techniques one skilled in the art any use to manufacture compounds disclosed herein. Different methods will be evident to those skilled in the art. Additionally, the various steps in the synthesis may be performed in an alternate sequence or order to give the desired compound(s). All documents cited herein are incorporated herein by reference in their entirety. For example, the following reactions are illustrations but not limitations of the preparation of some of the starting materials and examples used herein.

Schemes 1-6 describe various methods for the synthesis of intermediates that may be used to prepare compounds of the present invention. Various modifications to these methods may be envisioned by those skilled in the art to achieve similar results to that of the inventors given below.

Purine compound V' may be prepared as shown in Scheme 1.

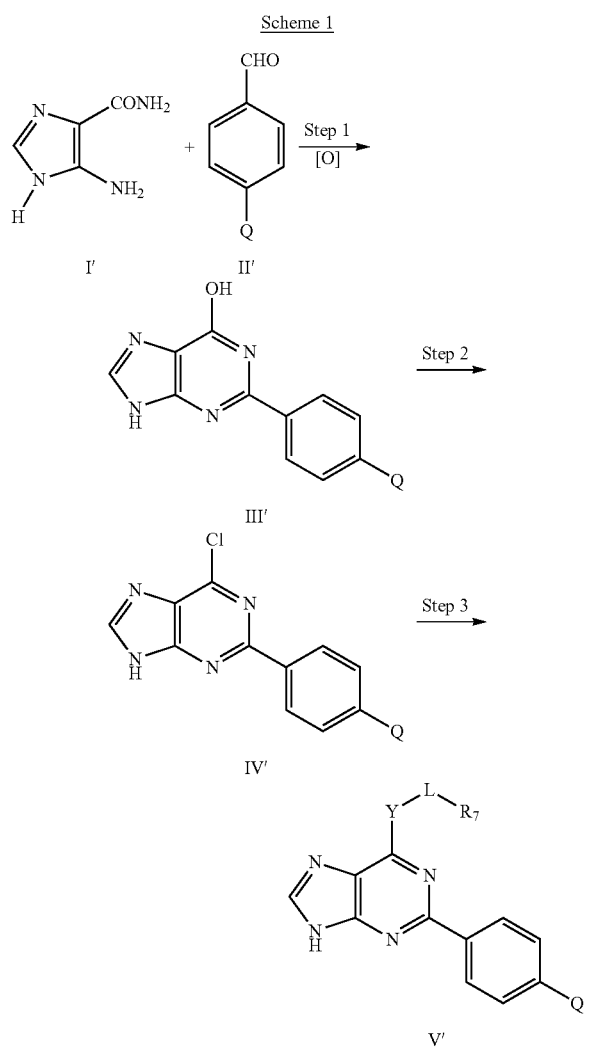

Step 1
Amide I' may undergo condensation reaction with aldehyde II', in the presence of oxidation agents such as Chloranil or bisulfite to afford hydroxylpurine III'. Suitable solvent for this reaction includes methylene chloride, Dimethylacetamide, DMF, methanol, and acetonitrile.

Step 2
Reaction of hydroxylpurine III' with chlorinating agent such as Phosphorous oxychloride or thionyl chloride affords chloropurine IV'. Suitable solvent for this reaction includes methylene chloride, acetonitrile, and tetrahydrofuran.

Step 3
Reaction of chloropurine IV' with nucleophile HYLR$_7$ affords Purine compound V'. Suitable solvent for this reaction includes methylene chloride, acetonitrile, chloroform, butanol, isopropyl alcohol, and tetrahydrofuran.

Purine compounds IX' and X' may be prepared as shown in Scheme 2.

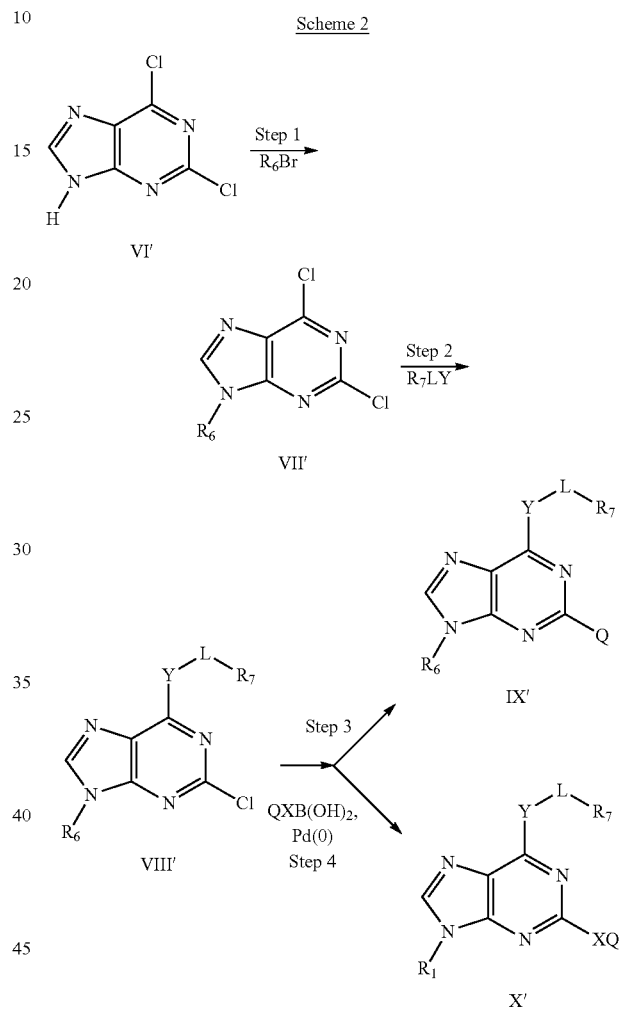

Step 1
Dichloropurine VI' may be reacted with electrophile R$_6$Br to afford N—R$_6$ dichloropurine VII', in the presence of base such as triethylamine, tetrabutylamonnium fluoride, and diisopropylethylamine. Other suitable electrophiles include R$_6$Cl, R$_6$I, R$_6$OTf, and R$_6$OTs. Generally, R$_6$OLG can be used here where LG is a good leaving group. Suitable solvents for this reaction include methylene chloride, acetonitrile, and tetrahydrofuran.

Step 2
Reaction of dichloropurine VII' with nucleophile HYLR$_7$, in the presence of base such as K$_2$CO$_3$, triethylamine, or diisopropylethylamine, affords purine VIII'. Suitable solvents for this reaction include methylene chloride, acetonitrile, acetone, chloroform, toluene, and tetrahydrofuran.

Steps 3 and 4
Reaction of purine VIII' with nucleophile QH or QB(OH)$_2$ affords purine IX'. Suitable solvents for this reaction include methylene chloride, acetonitrile, toluene, and tetrahydrofuran. Alternatively, reaction of purine VIII' with QXB(OH)$_2$, in the presence of catalyst such as Pd(0), affords purine compound X'.

Purine compounds XIV' and XV' may be prepared as shown in Scheme 3.

presence of base such as triethylamine and diisopropylethylamine affords purine XIV'. Suitable nucleophiles include R$_5$COCl. R$_5$CHO may also be used as nucleophile followed by oxidation using oxidant such as chloranil or iodine. Suitable solvents for this reaction include methylene chloride, acetonitrile, chloroform, and tetrahydrofuran.

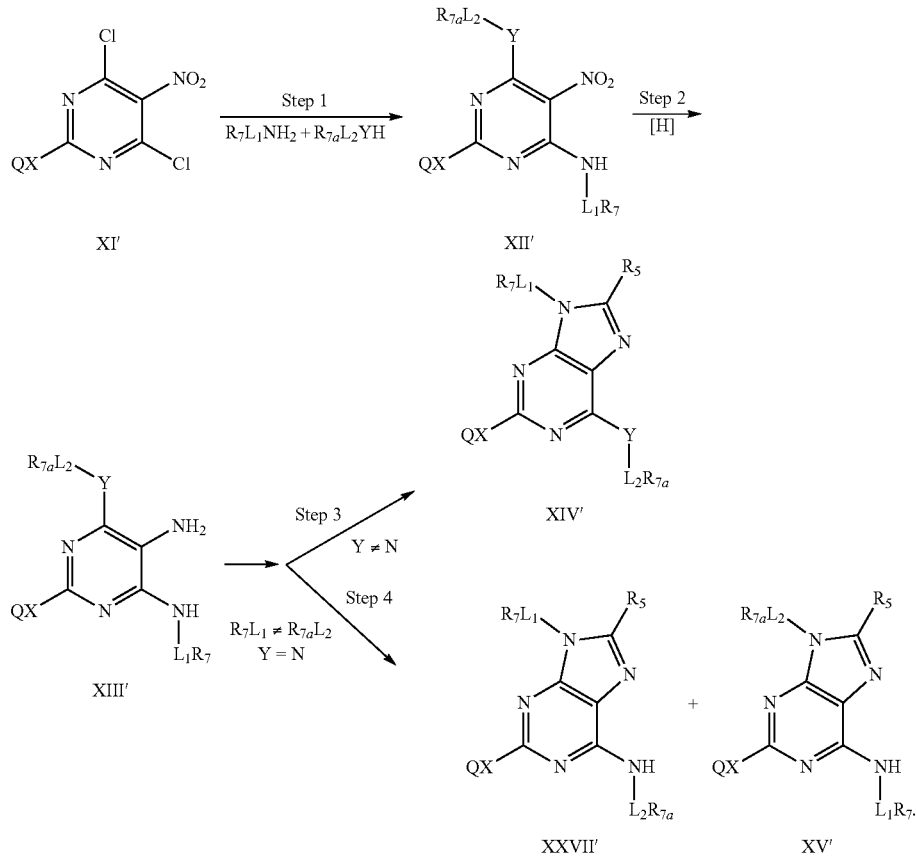

Step 1

Dichloro-nitropyrimidine XI' may be reacted with nucleophiles R$_7$L$_1$NH$_2$ and R$_{7a}$L$_2$YH sequentially to afford substituted pyrimidine XII', in the presence of base such as triethylamine and diisopropylethylamine. Suitable solvents for this reaction include methylene chloride, acetonitrile, chloroform, and tetrahydrofuran. R$_7$ and R$_{7a}$ are each independently H, alkyl, heteroaryl or NR$_3$R$_4$, wherein the heteroaryl is optionally substituted by (C$_1$-C$_4$)alkyl; L$_1$ and L$_2$ are each independently alkyl or alkenyl containing from 2 to 10 carbon atoms; wherein that R$_7$L$_1$ of purine compounds XIV' and XXVII' is alkyl, alkenyl, aryl, aralkyl, heterocycle, or alkylheterocycle and that R$_{7a}$L$_2$ of purine compound XV' is alkyl, alkenyl, aryl, aralkyl, heterocycle, or alkylheterocycle.

Step 2

Reduction of substituted pyrimidine XII' using reducing agent such as H$_2$, hydrosulfite, or SnCl$_2$, affords amino pyrimidine XIII'. Suitable solvents for this reaction include acetonitrile, ethanol, methanol, and tetrahydrofuran.

Step 3

In the instance that Y is not nitrogen, condensation of amino pyrimidine XIII' with nucleophile bearing R$_5$ in the Step 4

In the instance that Y is nitrogen and R$_7$L$_1$ and R$_{7a}$L$_2$ are not the same, condensation of amino pyrimidine XIII' with nucleophile bearing R$_5$ in the presence of base such as triethylamine and diisopropylethylamine affords a mixture of purine compounds XXVII' and XV'. Suitable nucleophiles include R$_5$COCl. R$_5$CHO may also be used as nucleophile followed by oxidation using oxidant such as chloranil or iodine. Suitable solvents for this reaction include methylene chloride, acetonitrile, chloroform, and tetrahydrofuran.

Purine compounds XXV' and XXVI' may be prepared as shown in Scheme 4.

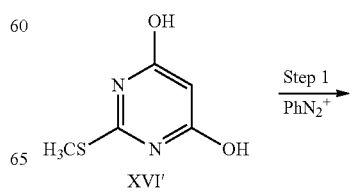

-continued

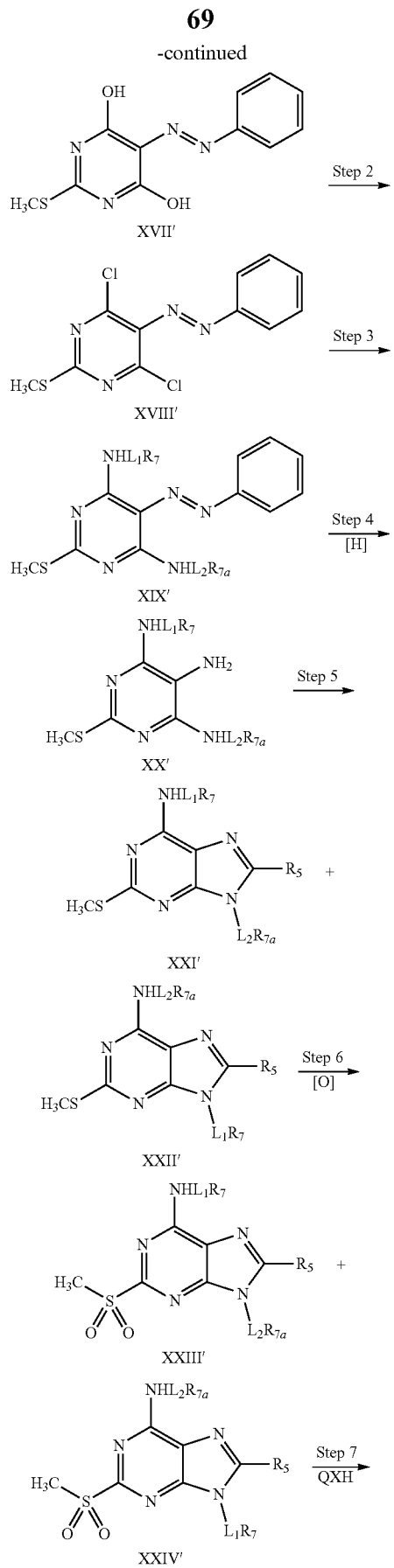

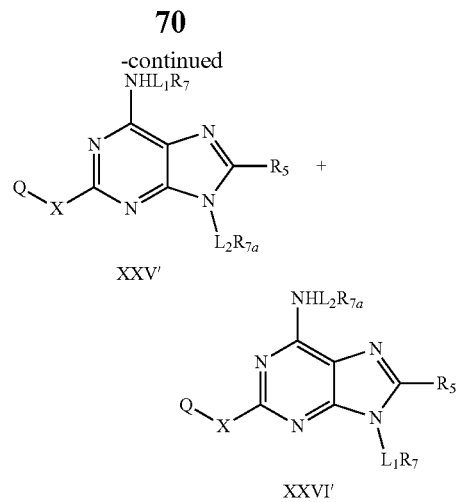

Step 1
Reaction of dihydroxy-pyrimidine XVI' with benzenediazonium affords diazene XVII'. Suitable solvents for this reaction include water and aqueous acetone.

Step 2
Chlorination of diazene XVII' with chlorinating agents such as phosphorous oxychloride or thionyl chloride affords dichloropyrimidine phenyldiazene XVIII'. Suitable solvents for this reaction include methylene chloroform, toluene.

Step 3
Reaction of dichloropyrimidine phenyldiazene XVIII' with nucleophiles $R_7L_1NH_2$ and $R_{7a}L_2NH_2$ sequentially affords disubstituted pyrimidine phenyldiazene XIX'. $R_7$ and $R_{7a}$ are each independently H, alkyl, heteroaryl or $NR_3R_4$, wherein the heteroaryl is optionally substituted by $(C_1-C_4)$ alkyl; $L_1$ and $L_2$ are each independently alkyl or alkenyl containing from 2 to 10 carbon atoms; provided that $R_7L_1$ of purine compound XXVI' is alkyl, alkenyl, aryl, aralkyl, heterocycle, or alkylheterocycle and that $R_{7a}L_2$ of purine compound XXV' is alkyl, alkenyl, aryl, aralkyl, heterocycle, or alkylheterocycle.

Step 4
Reduction of disubstituted pyrimidine phenyldiazene XIX' with hydrogen or hydrosulfite affords aminopyrimidine XX'. Suitable solvents for this reaction include tetrahydrofuran, ethanol, methanol, and water.

Step 5
Condensation of amino pyrimidine XX' with nucleophile bearing $R_5$ in the presence of base such as triethylamine and diisopropylethylamine affords a mixture of purine compounds XXI' and XXII'. Suitable nucleophiles include $R_5COCl$. $R_5CHO$ may also be used as nucleophile followed by oxidation using oxidant such as chloranil or iodine. Suitable solvents for this reaction include chloroform, methylene chloride, acetonitrile, and tetrahydrofuran.

Step 6
Oxidation of purine compounds XXI' and XXII' using oxidating agents such as affords methylsulfonyl purine compounds XXIII' and XXIV'. Suitable oxidating agents include peracids, permanganate, and hydrogen peroxide.

Step 7
Reaction of methylsulfonyl purine compounds XXIII' and XXIV' with nucleophile QXH affords a mixture of puridine compounds XXV' and XXVI'. Suitable solvents for this reaction include chloroform, ethanol, methylene chloride, acetonitrile, and tetrahydrofuran.

Purine compounds XXXII' may be prepared as shown in Scheme 5.

Scheme 5

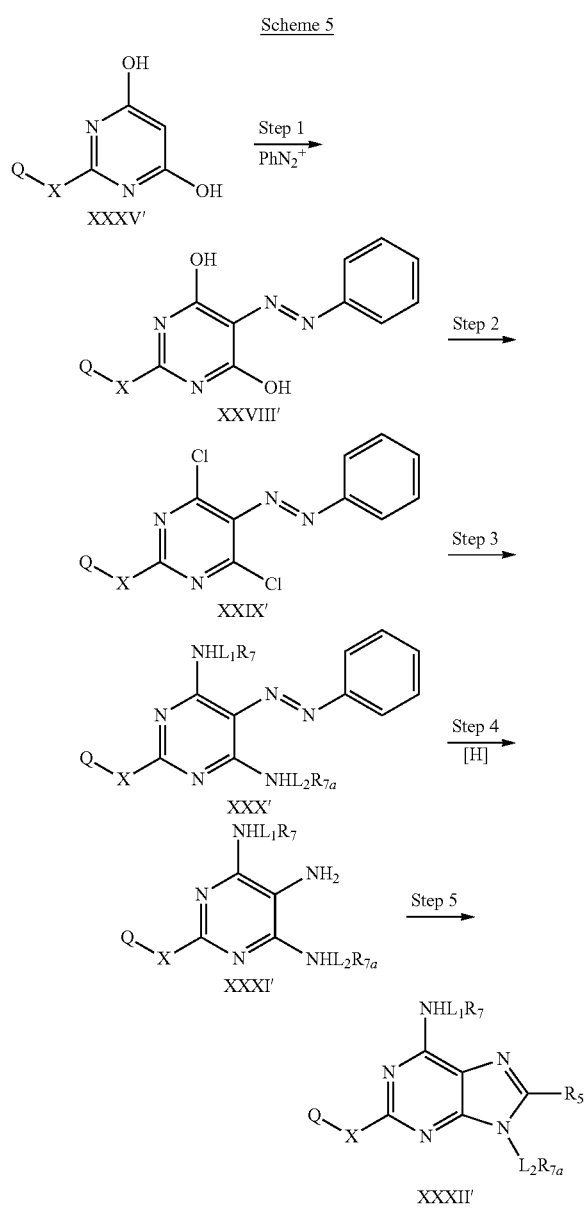

Step 1
Reaction of dihydroxy-pyrimidine XXXV' with benzenediazonium affords diazene XXVIII'. Suitable solvents for this reaction include water and aqueous acetone.

Step 2
Chlorination of diazene XXVIII' with chlorinating agents such as phosphorous oxychloride or thionyl chloride affords dichloropyrimidine phenyldiazene XXIX'. Suitable solvents for this reaction include methylene chloroform, toluene.

Step 3
Reaction of dichloropyrimidine phenyldiazene XXIX' with nucleophiles $R_7L_1NH_2$ and $R_{7a}L_2NH_2$ sequentially affords disubstituted pyrimidine phenyldiazene XXX'. $R_7$ and $R_{7a}$ can be the same or different and are each independently H, alkyl, heteroaryl or $NR_3R_4$, wherein the heteroaryl is optionally substituted by $(C_1-C_4)$alkyl; $L_1$ and $L_2$ are each independently alkyl or alkenyl containing from 2 to 10 carbon atoms; provided that $R_7L_1$ of purine compound XXX' is alkyl, alkenyl, aryl, aralkyl, heterocycle, or alkylheterocycle and that $R_{7a}L_2$ of purine compound XXX' is alkyl, alkenyl, aryl, aralkyl, heterocycle, or alkylheterocycle.

Step 4
Reduction of disubstituted pyrimidine phenyldiazene XXX' with hydrogen, ammonium formate, $Na_2S_2O_4$, or hydrosulfite affords aminopyrimidine XXXI'. Suitable solvents for this reaction include tetrahydrofuran, ethanol, methanol, and water.

Step 5
Condensation of amino pyrimidine XXXI' with nucleophile bearing $R_5$ or a precursor thereof affords compounds XXXII'. Bases may be used for this reaction. Suitable bases include triethylamine and diisopropylethylamine. Suitable nucleophiles include $R_5COCl$, trimethylorthoformate (wherein $R_5$ is H), or carbonyldiimidazole (wherein $R_5$ is OH). $R_5CHO$ may also be used as nucleophile followed by oxidation using oxidant such as chloranil or iodine. Suitable solvents for this reaction include chloroform, methylene chloride, acetonitrile, and tetrahydrofuran.

Purine compounds XXXIV' may be prepared as shown in Scheme 6.

Scheme 6

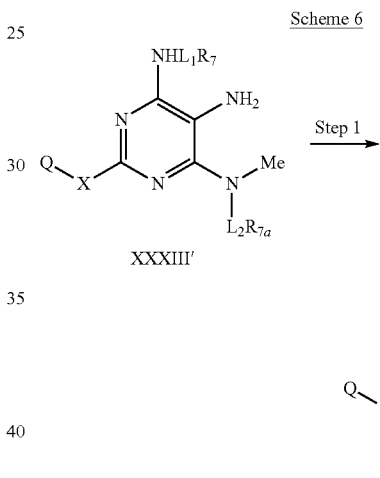

Step 1
Cyclization of amino pyrimidine XXXIII' affords compounds XXXIV'. Bases may be used for this reaction. Suitable bases include triethylamine and diisopropylethylamine. Trimethylorthoformate maybe used in this reaction. Suitable solvents for this reaction include chloroform, methylene chloride, acetonitrile, and tetrahydrofuran.

In addition, other compounds of formulae I-IV may be prepared by the procedures generally known to those skilled in the art. In particular, the following examples provide additional methods for preparing compounds of this invention.

The invention will now be further described by the working examples as below, which are preferred embodiments of the invention. These examples are illustrated rather than limiting, and it is to be understood that there may be other embodiments that fall within the spirit and scope of the invention as defined by the claims appended hereto.

Pharmaceutical Compositions

This invention also provides a pharmaceutical composition comprising at least one of the compounds as described herein or a pharmaceutically-acceptable salt or solvate thereof, and a pharmaceutically-acceptable carrier.

In yet another aspect, a pharmaceutical composition is described, comprising at least one a compound of Formula I, or a pharmaceutically acceptable salt thereof, and a pharmaceutically-acceptable carrier or diluent,

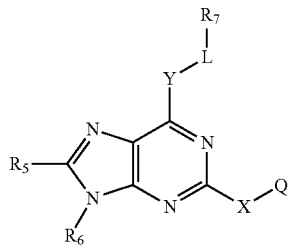

(I)

wherein

X is absent or is an alkyl, alkylamino, cycloalkyl, aryl, or heterocycle;

Q is H, $(CH_2)_q NR_1R_2$, $NR_1(CH_2)_p NR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(\!=\!O)R_{12}$, $(CH_2)_p OR_a$, and $(CH_2)_p NR_bR_c$, in which p is 2-4;

$R_7$ is H, alkyl, heteroaryl or $NR_3R_4$, wherein the heteroaryl is optionally substituted by $(C_1-C_4)$alkyl;

$R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle;

Y is oxygen, sulfur, or $NR_{11}$, where $R_{11}$ is hydrogen, alkyl, cycloalkyl, alkenyl, or aryl group;

$R_{12}$ is alkyl, aryl, or heterocycle;

L is alkyl or alkenyl containing from 2 to 10 carbon atoms;

$R_5$ is hydrogen, halogen, cyano, nitro, $CF_3$, $OCF_3$, alkyl, cycloalkyl, alkenyl, aryl, heterocycle, $OR_a$, $SR_a$, $S(\!=\!O)R_a$, $S(\!=\!O)_2R_a$, $NR_bR_c$, $S(\!=\!O)_2NR_bR_c$, $C(\!=\!O)OR_a$, $C(\!=\!O)R_a$, $C(\!=\!O)NR_bR_c$, $OC(\!=\!O)R_a$, $OC(\!=\!O)NR_bR_c$, $NR_bC(\!=\!O)OR_a$, or $NR_bC(\!=\!O)R_a$;

$R_6$ is hydrogen, alkyl, alkenyl, $(CH_2)_rC(\!=\!O)O(C_1-C_4)$alkyl, aryl, aralkyl, benzyl, heterocycle, $(CH_2)_p NR_bR_c$, or alkylheterocycle, wherein r is 0-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle;

provided that when $R_5$ and $R_6$ are H or $C_1-C_3$ alkyl, then Q is not H.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as butylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The term "carrier" denotes an organic or inorganic ingredient, natural or synthetic, with which the active ingredient is combined to facilitate the application. The components of the pharmaceutical compositions also are capable of being comingled with the compounds of the present invention, and with each other, in a manner such that there is no interaction which would substantially impair the desired pharmaceutical efficiency.

As set out above, certain embodiments of the present pharmaceutical agents may be provided in the form of pharmaceutically-acceptable salts. The term "pharmaceutically-acceptable salt", in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al., (1977) "Pharmaceutical Salts", *J. Pharm. Sci.* 66:1-19.)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, butionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra.)

Wetting agents, emulsifiers and lubricants, such as sodium lauryl sulfate, magnesium stearate, and polyethylene oxide-polybutylene oxide copolymer as well as coloring agents, release agents, coating agents, sweetening, flavoring and perfuming agents, preservatives and antioxidants can also be present in the compositions.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polybutylene oxide copolymer; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxybutylmethyl cellulose), lubricant, inert diluent, preservative, disintegrant (for example, sodium starch glycolate or cross-linked sodium carboxymethyl cellulose), surface-active or dispersing agent. Molded tablets, may be, made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxybutylmethyl cellulose in varying butortions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if apbutriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isobutyl alcohol, ethyl carbonate, ethyl acetate, benzyl alcohol, benzyl benzoate, butylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxybutyl-.beta.-cyclodextrin, may be used to solubilize compounds.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active pharmaceutical agents of the invention.

Formulations of the present invention which are suitable for vaginal administration also include pessaries, tampons, creams, gels, pastes, foams or spray formulations containing such carriers as are known in the art to be apbutriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or butellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary butellants, such as chlorofluorohydrocarbons and volatile unsubstituted hydrocarbons, such as butane and butane.

Transdermal patches have the added advantage of providing controlled delivery of a compound of the present invention to the body. Such dosage forms can be made by dissolving, or dispersing the pharmaceutical agents in the buter medium. Absorption enhancers can also be used to increase the flux of the pharmaceutical agents of the invention across the skin. The rate of such flux can be controlled, by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle. One strategy for depot injections includes the use of polyethylene oxide-polybutylene oxide copolymers wherein the vehicle is fluid at room temperature and solidifies at body temperature.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations are also prepared by entrapping the drug in liposomes or microemulsions, which are compatible with body tissue.

When the compounds of the present invention are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the compound of the present invention may be administered concurrently with another anti-inflammatory or immunesupressant agent); such as but not limited to NSAIDS, DMARDS, Steroids, or biologics such as antibody therapies) or they may achieve different effects (e.g., control of any adverse effects).

The compounds of the invention may be administered intravenously, intramuscularly, intraperitoneally, subcutaneously, topically, orally, or by other acceptable means. The compounds may be used to treat arthritic conditions in mammals (i.e., humans, livestock, and domestic animals), birds, lizards, and any other organism, which can tolerate the compounds.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Administration to a Subject

Some aspects of the invention involve administering an effective amount of a composition to a subject to achieve a specific outcome. The small molecule compositions useful according to the methods of the present invention thus can be formulated in any manner suitable for pharmaceutical use.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the compound can be administered to a subject by any mode allowing the compound to be taken up by the appropriate target cells. "Administering" the pharmaceutical composition of the present invention can be accomplished by any means known to the skilled artisan. Specific routes of administration include but are not limited to oral, transdermal (e.g., via a patch), parenteral injection (subcutaneous, intradermal, intramuscular, intravenous, intraperitoneal, intrathecal, etc.), or mucosal (intranasal, intratracheal, inhalation, intrarectal, intravaginal, etc.). An injection can be in a bolus or a continuous infusion.

For example the pharmaceutical compositions according to the invention are often administered by intravenous, intramuscular, or other parenteral means, or by biolistic "gene-gun" application to the epidermis. They can also be administered by intranasal application, inhalation, topically, orally, or as implants, and even rectal or vaginal use is possible. Suitable liquid or solid pharmaceutical preparation forms are, for example, aqueous or saline solutions for injection or inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer R (1990) *Science* 249: 1527-33, which is incorporated herein by reference.

The concentration of compounds included in compositions used in the methods of the invention can range from about 1 nM to about 100 μM. Effective doses are believed to range from about 10 picomole/kg to about 100 micromole/kg.

The pharmaceutical compositions are preferably prepared and administered in dose units. Liquid dose units are vials or ampoules for injection or other parenteral administration. Solid dose units are tablets, capsules, powders, and suppositories. For treatment of a patient, depending on activity of the compound, manner of administration, purpose of the administration (i.e., prophylactic or therapeutic), nature and severity of the disorder, age and body weight of the patient, different doses may be necessary. The administration of a given dose can be carried out both by single administration in the form of an individual dose unit or else several smaller dose units. Repeated and multiple administration of doses at specific intervals of days, weeks, or months apart are also contemplated by the invention.

The compositions can be administered per se (neat) or in the form of a pharmaceutically acceptable salt. When used in medicine the salts should be pharmaceutically acceptable, but non-pharmaceutically acceptable salts can conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Compositions suitable for parenteral administration conveniently include sterile aqueous preparations, which can be isotonic with the blood of the recipient. Among the acceptable vehicles and solvents are water, Ringer's solution, phosphate buffered saline, and isotonic sodium chloride solution. In addition, sterile, fixed oils are conventionally employed as a solvent or suspending medium. For this purpose any bland fixed mineral or non-mineral oil may be employed including synthetic mono- or diglycerides. In addition, fatty acids such as oleic acid find use in the preparation of injectables. Carrier formulations suitable for subcutaneous, intramuscular, intraperitoneal, intravenous, etc. administrations can be found in *Remington's Pharmaceutical Sciences*, Mack Publishing Company, Easton, Pa.

The compounds useful in the invention can be delivered in mixtures of more than two such compounds. A mixture can further include one or more adjuvants in addition to the combination of compounds.

A variety of administration routes is available. The particular mode selected will depend, of course, upon the particular compound selected, the age and general health status of the subject, the particular condition being treated, and the dosage required for therapeutic efficacy. The methods of this invention, generally speaking, can be practiced using any mode of administration that is medically acceptable, meaning any mode that produces effective levels of response without causing clinically unacceptable adverse effects. Preferred modes of administration are discussed above.

The compositions can conveniently be presented in unit dosage form and can be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Equivalents

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional informa-

EXAMPLES

Example 1

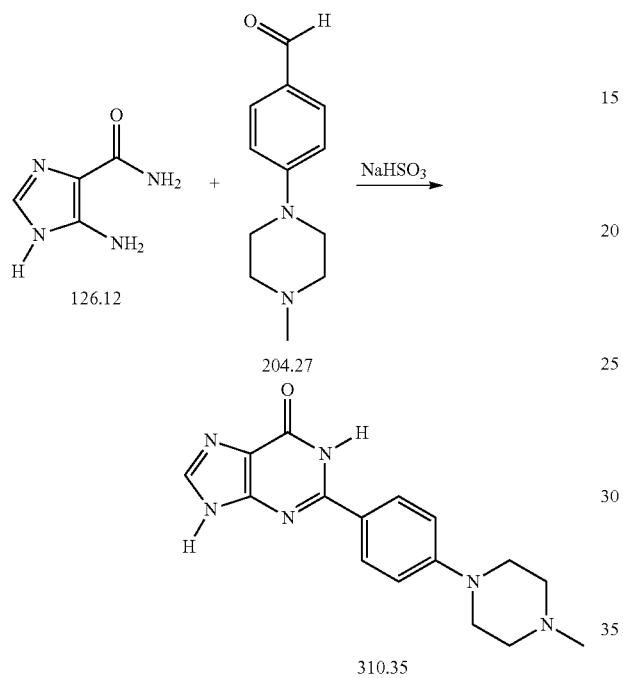

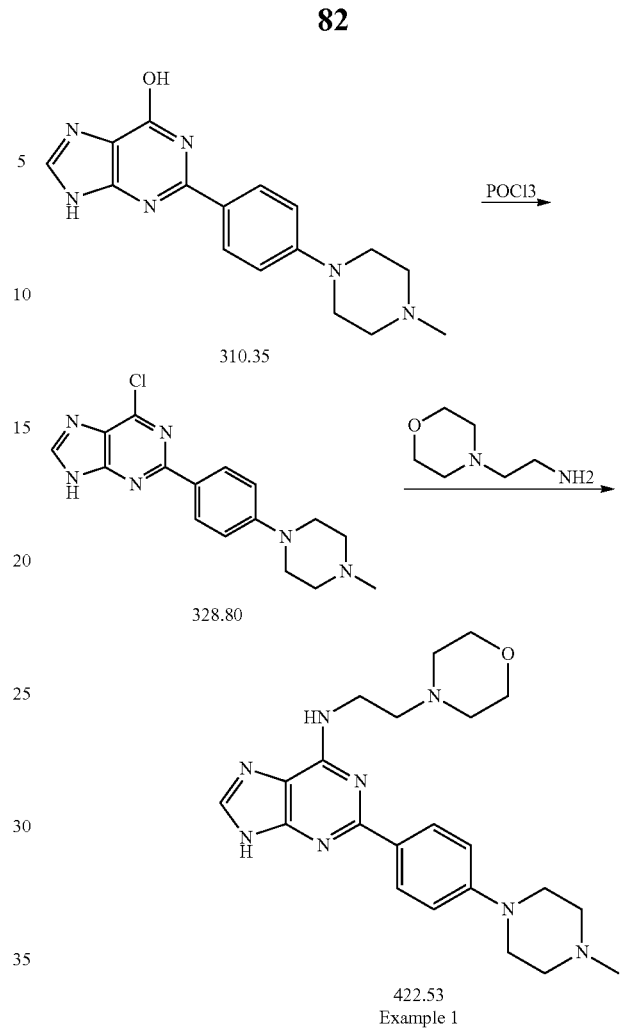

Example 1

A mixture of 5-aminoimidazole-4-carboxamide (12.6 gm, 0.10 moles), N-methyl-N'-(4-formylphenyl)piperazine (20.4 gm, 0.10 moles), sodium metabisulfite (14.3 gm, 0.075 moles) and water (1.4 mL) in dimethylacetamide (150 mL) was heated at 150° C. with stirring for 2 hours. The heat was removed and water (300 mL) was cautiously added. The resulting brown solution was then cooled in an ice bath with stirring. The solid which separated was isolated by filtration, washed with water and dried. TLC (silica, 25% methanol in methylene chloride) showed the presence of two products; a bright yellow compound with rf=0.42 and a colorless, blue fluorescent compound with rf=0.20. The total yield was 5.0 gm.

The crude product was dissolved in 30% methanol in chloroform (200 mL) and silica gel (75 gm) was added. This mixture was stripped of solvent under vacuum to give the product mixture adsorbed to silica. This material was deposited on top of a silica column (18 in×2 in). The column was then developed using 30% methanol in chloroform using 5 psi nitrogen to accelerate the process. The two compounds were cleanly separated with the yellow compound eluting first. The fractions containing the separated compounds were evaporated to give the yellow compound in a yield of 2.45 gm and the colorless compound in a yield of 2.49 gm. The NMR of the latter compound was consistent with the quinazolinone structure.

The compound from above (1.35 gm, $4.3 \times 10^{-3}$ moles) was suspended in chlorobenzene (10 mL) and phosphorous oxychloride (10 mL) was added followed by diisopropylethylamine (1.1 gm, 1.5 mL, $8.6 \times 10^{-3}$ moles). This mixture was stirred at 130° C. under argon for 5 hours. The excess phosphorous oxychloride was removed by distillation and, after cooling, the chlorobenzene mixture was stirred with dichloromethane (250 mL) and 5% sodium bicarbonate solution (200 mL) until all of the solid had dissolved in the dichloromethane (about 2 hours). The dichloromethane solution was isolated, dried over magnesium sulfate and then filtered and evaporated under vacuum. The brown residue was then dissolved in n-butanol (10 mL) and N-2-aminoethylmorpholine (2.0 mL) was added. This solution was then heated at reflux overnight. After cooling, the reaction was diluted with dichloromethane (100 mL). This solution was extracted with 5% hydrochloric acid solution (2×50 mL). The combined acidic extracts were washed with dichloromethane (50 mL) and were then made basic by the addition of solid sodium carbonate. This mixture was extracted with dichloromethane (2×50 mL). The combined extracts were dried over magnesium sulfate. After filtering to remove the drying agent, the extracts were evaporated under vacuum. The remaining solid was purified by chromatography on silica using 20% methanol in chloroform as eluent. The fractions containing the product were pooled and evaporated to provide the desired compound in a yield of 123 mg. (6.8% from the hydroxy compound). The NMR was consistent with the structure. LC/MS: M+1=423.31.

Hydrochloride salt formation: The adenine (100 mg, 2.4×10⁻⁴ moles) was dissolved in boiling ethanol (4 mL). To this solution was added concentrated hydrochloric acid (60λ). The solution was cooled which caused the tris-hydrochloride salt to crystallize as solid. This was isolated by filtration and was washed with ethanol followed by diethyl ether. The solid salt was dried under vacuum. Yield=87.3 mg, Mw=531.9.

Example 54

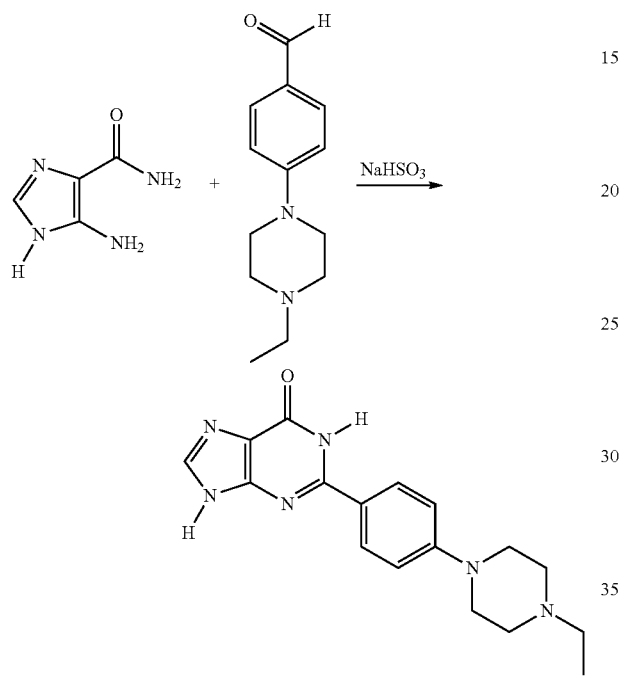

A mixture of 5-aminoimidazole-4-carboxamide (6.3 gm, 0.05 moles), N-ethyl-N'-(4-formylphenyl)piperazine (10.9 gm, 0.05 moles), sodium metabisulfite (7.13 gm, 0.037 moles) and water (675 µL) in dimethylacetamide (75 mL) was heated at 150° C. with stirring for 90 minutes. The heat was removed and water (150 mL) was cautiously added. The resulting brown solution was then cooled in an ice bath with stirring. The solid which separated was isolated by filtration, washed with water and dried. TLC (silica, 25% methanol in methylene chloride) showed the presence of two products; a bright yellow compound with rf=0.48 and a colorless, blue fluorescent compound with rf=0.25. The total yield was 2.4 gm.

The crude product was dissolved in 20% methanol in chloroform (200 mL) and silica gel (25 gm) was added. This mixture was stripped of solvent under vacuum to give the product mixture adsorbed to silica. This material was deposited on top of a silica column (18 in×2 in). The column was then developed using 20% methanol in chloroform using 5 psi nitrogen to accelerate the process. The two compounds were cleanly separated with the yellow compound eluting first. The fractions containing the separated compounds were evaporated to give the yellow compound in a yield of 0.77 gm and the colorless compound in a yield of 0.90 gm. The NMR of the latter compound was consistent with the quinazolinone structure.

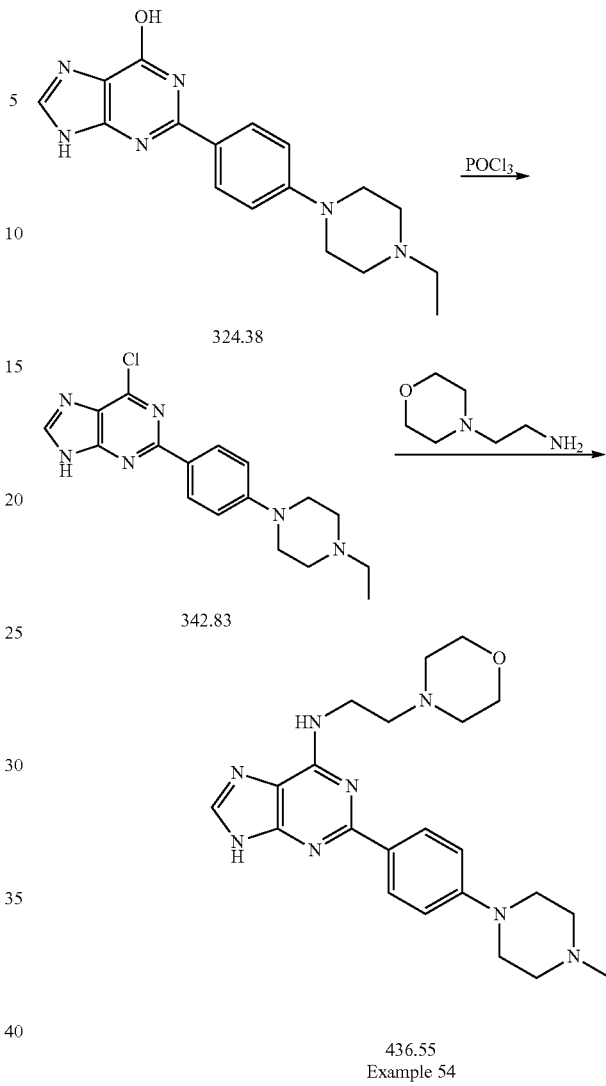

436.55
Example 54

The compound from above (0.90 gm, 2.77×10⁻³ moles) was suspended in chlorobenzene (20 mL) and phosphorous oxychloride (1.0 mL) was added. This mixture was stirred at 130° C. under argon for 9 hours. After cooling the chlorobenzene was decanted from the dark brown solid. The solid was stirred with dichloromethane (250 mL) and 5% sodium bicarbonate solution (200 mL) until all of the solid had dissolved in the dichloromethane (about 2 hours). The dichloromethane solution was isolated, dried over magnesium sulfate and then filtered and evaporated under vacuum. The brown residue was then dissolved in n-butanol and N-2-aminoethylmorpholine (2.0 mL) was added. This solution was then heated at reflux for 3 hours. After cooling, the reaction was filtered to remove some insoluble material and was then diluted with diethyl ether (200 mL). This solution was extracted with 5% hydrochloric acid solution (2×50 mL). The combined acidic extracts were washed with diethyl ether (100 mL) and were then made basic by the addition of solid sodium carbonate. This mixture was extracted with dichloromethane (2×50 mL). The combined extracts were dried over magnesium sulfate. After filtering to remove the drying agent, the extracts were evaporated under vacuum. The remaining solid was purified by chromatography on silica using 20% methanol in chloroform as eluent. The fractions containing the product were pooled and evaporated to provide the desired compound in a yield of 90 mg. (7.4% from the hydroxy compound). The NMR was consistent with the structure.

Example 55

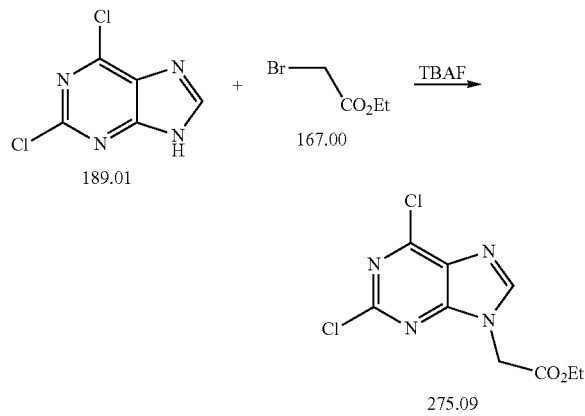

A solution of 2,4-dichloropurine (1.0 gm, $5.3 \times 10^{-3}$ moles) and ethyl bromoacetate (1.67 gm, $1.0 \times 10^{-3}$ moles) in tetrahydrofuran (5 mL) was treated with a solution of tetrabutylammonium fluoride (10 mL, 1.0M, $1.0 \times 10^{-2}$ moles). After stirring for 30 minutes a TLC (silica, 10% methanol in methylene chloride) showed that the starting material (Rf=0.38) had been cleanly converted to a single product (Rf=0.74). The reaction was diluted in diethyl ether (100 mL) and this solution was washed with water (2×50 mL). After drying over magnesium sulfate, the solution was filtered to remove the drying agent and the filtrates were evaporated under vacuum. The solid white residue was recrystallized from ethyl acetate (5 mL) and hexane (20 mL) to give the crystalline product in a yield of 0.95 gm (65.2%).

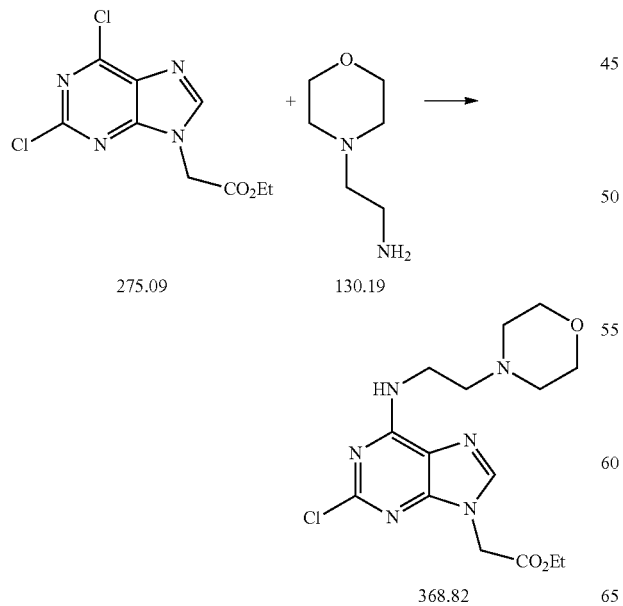

The carboethoxypurine (0.95 gm, $3.45 \times 10^{-3}$ moles) and N-2-aminoethylmorpholine (583 mg, 5884, $4.48 \times 10^{-3}$ moles) were combined in 2-methyltetrahydrofuran (10 mL) and 2-propanol (3 mL). After being heated at reflux for 60 minutes, a TLC (silica, 10% methanol in methylene chloride) showed that there was a little starting material left. More N-2-aminoethylmorpholine (315 mg, 3184, $2.42 \times 10^{-3}$ moles) was added and heating was continued for 15 minutes. A TLC (silica, 10% methanol in methylene chloride) showed that the starting material (Rf=0.74) had been cleanly converted to a single product (Rf=0.33). The reaction was cooled and diluted with methylene chloride (100 mL). This solution was washed with saturated sodium bicarbonate (50 mL) followed by water (50 mL) and was then dried over magnesium sulfate. The solution was filtered to remove the drying agent and the filtrates were evaporated under vacuum to give an oil. The oil was dissolved in diethyl ether (15 mL) and this solution was cooled in the refrigerator. The product crystallized as a white solid and was isolated by filtration. After washing with diethyl ether and drying there was obtained 0.98 gm (77%) of the purified product as an off white solid.

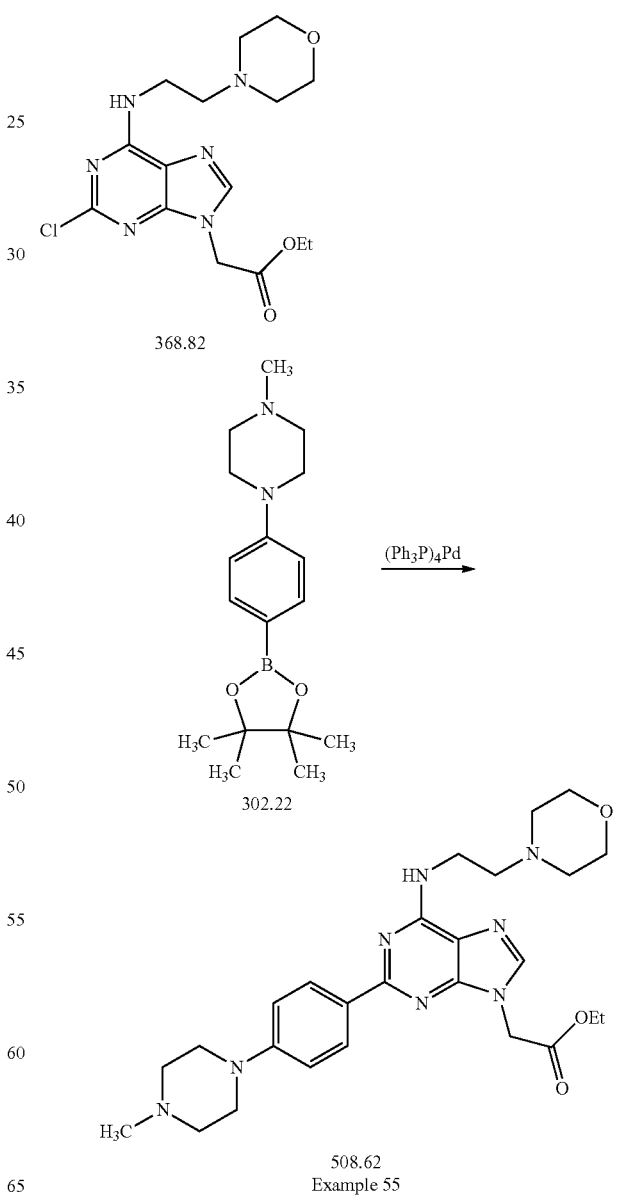

In a round bottom flask with a stir bar the following were combined:

| | | | |
|---|---|---|---|
| 1. | The chloroadenine derivative from above. | 0.50 gm | $1.36 \times 10^{-3}$ moles |
| 2. | The piperazine boronic acid ester | 0.45 gm | $1.50 \times 10^{-3}$ moles |
| 3. | Potassium carbonate | 0.11 gm | $7.70 \times 10^{-4}$ moles |
| 4. | Tetrakis triphenylphosphine palladium | 34.5 mg | $2.99 \times 10^{-5}$ moles |
| 5. | Acetonitrile | 5 mL | |
| 6. | Water | 5 mL | |

The flask was evacuated and flushed with argon before being heated at 70° C. for 90 minutes. TLC (silica, 105 methanol in methylene chloride) showed the formation of two product spots. One blue fluorescent compound (Rf=0.17) and a non-fluorescent compound (Rf=0.15). It appeared that the starting adenine (Rf=0.33) had been consumed. The reaction was cooled and was partitioned between water (100 mL) and methylene chloride (100 mL). The organic solution was isolated and dried over magnesium sulfate. After filtration the solvents were removed under vacuum and the residue was purified by chromatography on silica and the product was eluted by gradually changing the eluent to 20% methanol in methylene chloride. The fractions containing the product were pooled and evaporated to give the purine in a yield of 63 mg. $^1$H NMR: 1.22 ppm, Triplet, 3H, 2.50 ppm, multiplet, 4H, 2.83 ppm, doublet, 3H, 3.02 ppm, triplet, 2H, 3.18 ppm, multiplet, 4H, 3.58 ppm, multiplet, 8H, 3.95 ppm, doublet, 6H, 4.19 ppm, quartet, 2H, 5.15 ppm, singlet, 2H, 7.05 ppm, doublet, 2H, 8.15 ppm, singlet, 1H, 8.24 ppm, doublet, 2H.

The purine (63 mg, $1.2\times10^{-4}$ moles) was dissolved in methanol (3 mL) and a solution of sulfuric acid in methanol (104 µL of a 233 mg/mL solution, $2.46\times10^{-4}$ moles) was added. After cooling in the refrigerator, the solid bisulfate salt was isolated by centrifugation. After washing (7 mL of 50/50 methanol/ethyl ether), the solid was dried under vacuum to give the bisulfate salt (Mw=704.78) as a tan solid. Yield was 47.1 mg.

Example 56

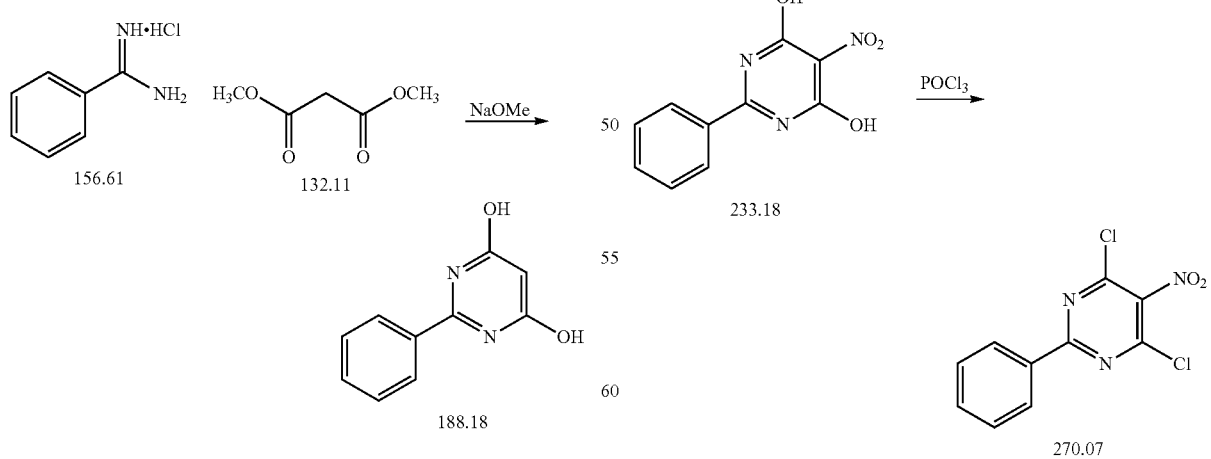

Benzamidine hydrochloride (26.0 gm, 0.166 moles) and dimethyl malonate (21.9 gm, 0.166 moles) were combined in dry methanol (200 mL). This mixture was stirred as 30% sodium methoxide in methanol (89.7 gm, 0.498 moles) was added. A precipitate of sodium chloride formed and this mixture was stirred at 55° C. for 2 hours. The reaction mixture was diluted with water (500 mL) to form a clear solution. This was acidified by the addition of acetic acid (35 mL) causing a white precipitate to quickly form. After stirring for 30 minutes, the solid was isolated by filtration. The filter cake was washed, in turn with water, methanol and acetone. After drying, the 2-phenyl-4,6-dihydroxypyrimidine was obtained in a yield of 25 gm (80%) as a white solid.

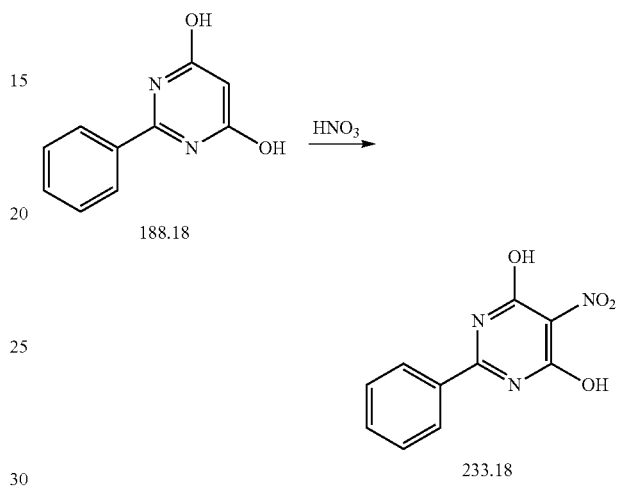

A mixture of 2-phenyl-4,6-dihydroxypyrimidine (15.6 gm, $8.29\times10^{-2}$ moles) and acetic acid (45 mL) were swirled together as 90% nitric acid was slowly added by pasteur pipette. Once the addition was complete, the resulting red solution was stirred at 50° C. for 45 minutes. Then water (150 mL) was added and the resulting mixture was stirred on ice. Once cooled, the solid was isolated by filtration and was washed with water. The solid was then washed with 2-propanol and dried to provide the nitropyrimidine as a purple solid in a yield of 5.3 gm (27.4%).

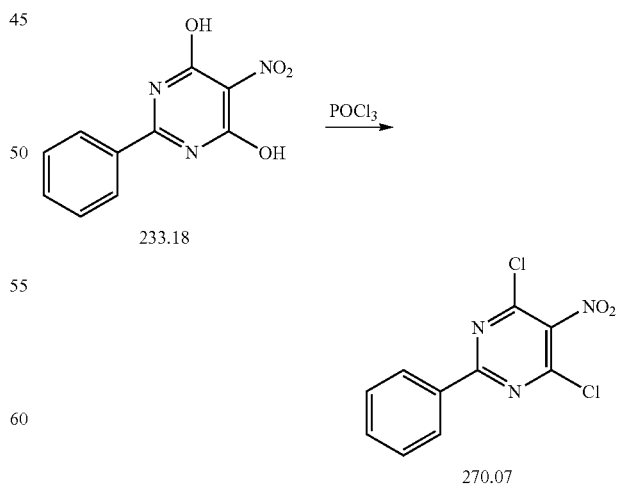

A slurry of 2-phenyl-4,6-dihydroxy-5-nitropyrimidine (5.3 gm, $2.27\times10^{-2}$ moles) in phosphorous oxychloride (23 mL) was stirred as diisopropylethylamine (7.0 mL) was slowly added. The resulting orange solution was heated at 100° C. for one hour. Excess phosphorous oxychloride was removed under reduced pressure and the residual material was treated with ice and water (100 gm). The yellow, solid precipitate was extracted into ethyl acetate (200 mL) and this solution was washed with brine. After drying over magnesium sulfate, the solution was filtered and evaporated under reduced pressure. The remaining solid was recrystallized from 2-propanol to provide the 2-phenyl-4,6-dichloro-5-nitropyrimidine as a yellow solid in a yield of 3.2 gm (52%).

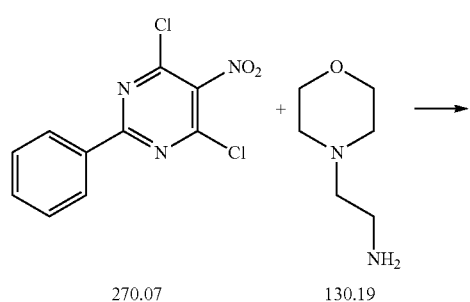

270.07    130.19

A mixture of 2-phenyl-4,6-dichloro-5-nitropyrimidine (3.2 gm, $1.18 \times 10^{-2}$ moles) and N-2-aminoethylmorpholine (3.39 gm, 3.42 mL, $2.6 \times 10^{-2}$ moles) with diisopropylethylamine (4.50 mL) in 2-propanol (50 mL) was heated to boiling. After 2 hours at reflux the hot solution was cooled on ice. Upon cooling, the product crystallized as a yellow solid. This was isolated by filtration, washed with 2-propanol and dried to provide the product in a yield of 4.6 gm, (85.2%).

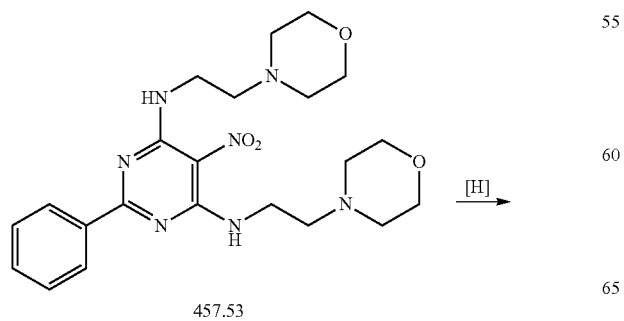

457.53

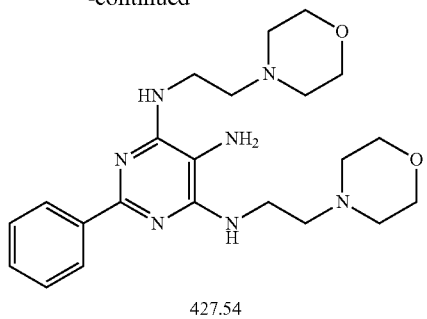

427.54

The nitro pyrimidine (1.83 gm, $4.0 \times 10^{-3}$ moles) was stirred in methanol (20 mL) and THF (10 mL). To this was added ammonium formate (1.3 gm) dissolved in water (4 mL) along with 10% palladium on carbon (200 mg). After being heated at reflux for 3 hours, TLC (silica, 10% methanol in methylene chloride) showed consumption if the nitro compound (Rf=0.65) with a single product (Rf=0.13). After cooling, the catalyst was removed by filtration and the filtrates were diluted with methylene chloride (200 mL). The solution was washed with water (50 mL) and dried over magnesium sulfate. After filtration to remove the magnesium sulfate, the solvents were removed under reduced pressure to provide the triaminopyrimidine as a pale pink solid.

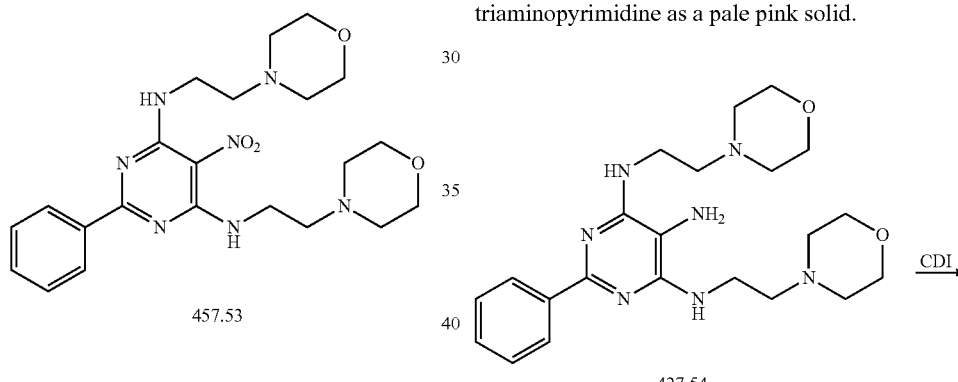

427.54

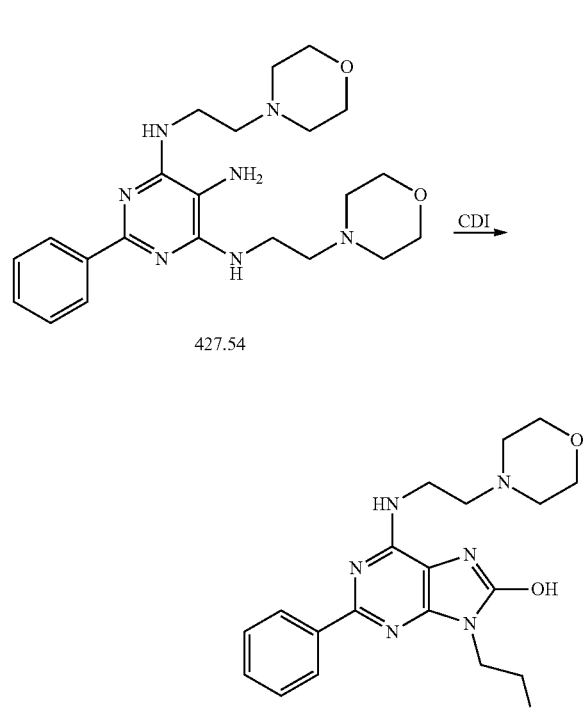

Example 56
453.54

The triaminopyrimidine from above was stirred in methylene chloride (30 mL) and carbonyl diimidazole (0.65 gm) was added. A pale pink solution soon formed which was stirred overnight. Water (20 mL) was added and stirring was continued for 30 minutes. Methylene chloride (100 mL) was added and the mixture was washed with water (50 mL). The methylene chloride solution was dried over magnesium sulfate before being filtered and evaporated under reduced pressure. The residual white solid was purified by chromatography on silica using 10% methanol in methylene chloride as eluent. The fractions containing the product were pooled and evaporated to provide Example 56 as a white powder in a yield of 919 mg (51%). LC/MS: M+1=454.32. $^1$H NMR: 2.5 ppm, multiplet, 12H, 3.25 ppm, multiplet, 4H, 3.55 ppm, multiplet, 6H, 4.0 ppm, multiplet, 2H, 7.3 ppm, multiplet, 3H, 8.3 ppm, multiplet, 2H.

Example 57

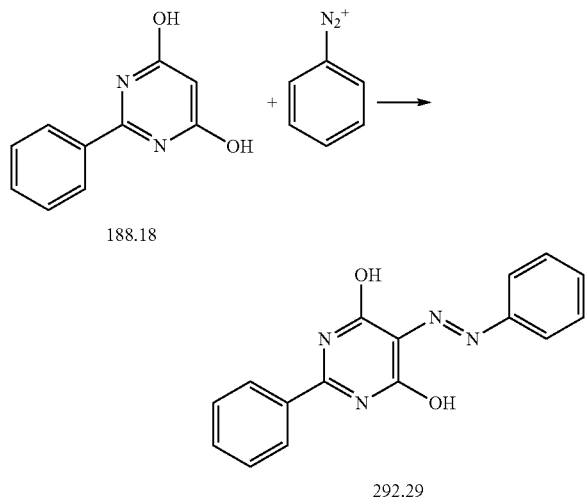

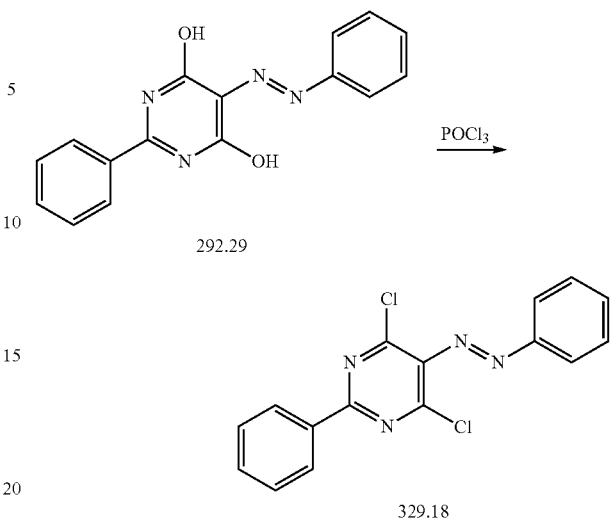

Solution 1:

Aniline (9.3 gm, 0.10 moles) was dissolved in water (200 mL) and Ice (100 gm) containing concentrated hydrochloric acid (20 mL). This solution was stirred as a solution of sodium nitrite (6.9 gm, 0.10 moles) dissolved in water (50 mL) was dripped in. Once the addition was complete the diazonium solution was kept on ice as solution 2 was prepared.

Solution 2:

Sodium hydroxide (24 gm, 0.60 moles) and 2-phenyl-4,6-dihydroxypyrimidine (18.8 gm, 0.10 moles) were dissolved in water (200 mL) and once dissolution was complete, ice (100 gm) was added.

Solution 1 was slowly poured into solution 2 at ice temperature with stirring. The resulting bright orange solution was stirred and the sodium salt of the azo compound soon crystallized forming a thick slurry. After 30 minutes, the thick slurry was acidified with concentrated hydrochloric acid and after sitting for 30 minutes, the azo compound was isolated by filtration. The damp solid was washed with water and dried to provide the azopyrimidine as a yellow solid in a yield of 12.8 gm (43.7%)

The dihydroxyphenylazopyrimidine (11.7 gm, 0.04 moles) was powdered and mixed with phosphorous oxychloride (45 mL). This mixture was stirred as diisopropylethylamine (12.3 mL) was slowly added. The resulting orange slurry was heated at reflux for 1 hour. Upon cooling, excess phosphorous oxychloride was removed under reduced pressure. The residual material was treated with ice and this was then extracted with methylene chloride (300 mL). The methylene chloride extracts were washed with water (2×150 mL) before being dried over magnesium sulfate. After filtration, the solvent was removed under reduced pressure. The residual material was stirred with a 50/50 mixture of ethyl acetate and hexane (50 mL). The resulting solid was isolated by filtration and was washed with a 50/50 mixture of ethyl acetate and hexane. After drying, there was obtained 10.5 gm (79.7%) of the product as an orange solid.

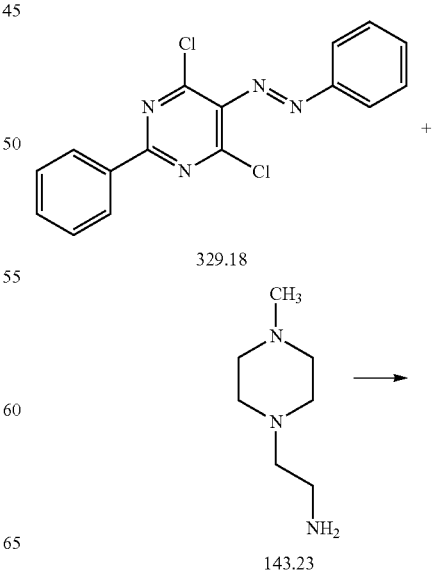

-continued

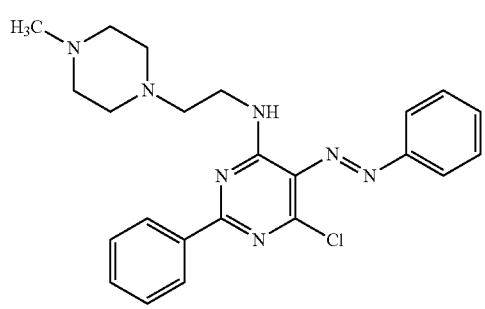

435.95

The dichloropyrimidine (2.30 gm, $6.98 \times 10^{-3}$ moles) was dissolved in methylene chloride and N-methyl-N'-(2-aminoethyl)piperazine (1.0 gm, $6.98 \times 10^{-3}$ moles) was added. After stirring at room temperature for 1 hour, TLC (silica, 10% methanol in methylene chloride) showed some remaining starting material (Rf=0.91) along with a single product (Rf=0.32). Diisopropylethylamine (0.902 gm, 1.22 mL, $6.98 \times 10^{-3}$ moles) was added and this solution was heated at 45° C. for 90 minutes. After cooling, the methylene chloride was removed under reduced pressure and the remaining material was purified by chromatography on silica using 15% methanol in methylene chloride as eluent. The fractions containing the product were pooled and evaporated to provide 2.1 gm (69%) of the product as an orange solid.

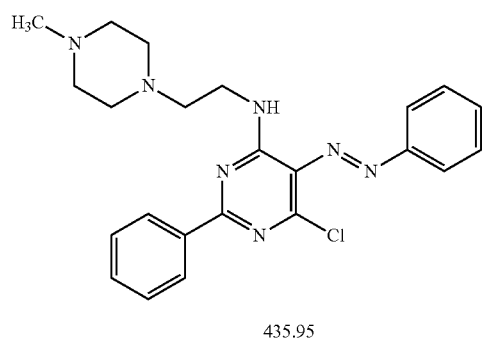

435.95

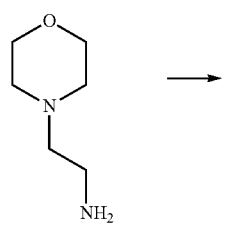

130.19

-continued

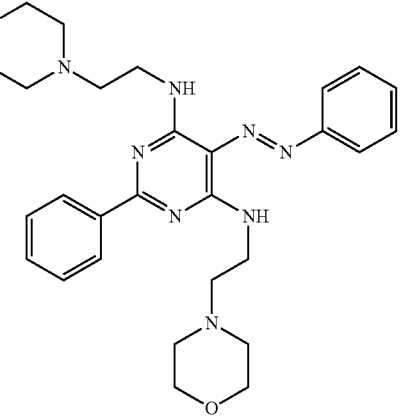

529.68

The monochloropyrimidine (1.7 gm, $3.9 \times 10^{-3}$ moles) and N-(2-aminoethyl)morpholine (5.08 gm, $3.9 \times 10^{-2}$ moles) were combined and heated at 150° C. A dark orange solution formed upon heating and after heating for 15 minutes, TLC (15% methanol in methylene chloride) showed clean conversion to a single compound (Rf=0.37). The solution was cooled to 60° C. and 2-propanol (25 mL) was added. Upon cooling, the product crystallized as a yellow solid. This was isolated by filtration, washed with 2-propanol and dried to give 1.7 gm (82.3%) of the diaminophenylazopyrimidine.

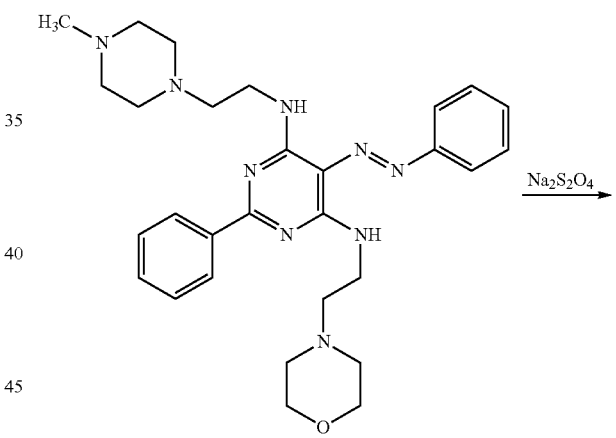

529.68

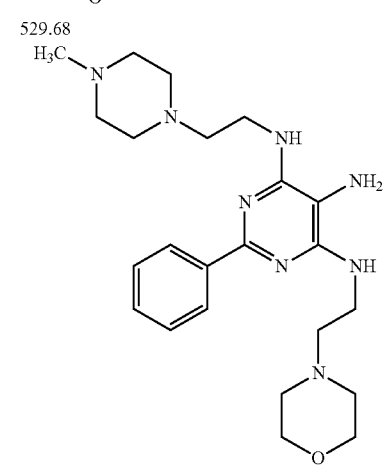

440.58

The azopyrimidine (1.7 gm, 3.2×10⁻³ moles) was stirred in water (25 mL) containing acetic acid (1.0 mL). This mixture was heated at 65° C. forming an orange solution. To this stirred solution was added sodium dithionite (3 gm) in 3 equal portions over 5 minutes. After the last addition, a colorless solution had formed. After stirring at 65° C. for an additional 15 minutes the solution was cooled and made basic by the addition of potassium carbonate. The oil which had separated was extracted into methylene chloride (100 mL) and the extracts were dried over magnesium sulfate. After filtration, the methylene chloride was evaporated under reduced pressure. The remaining material was used in the next step without purification.

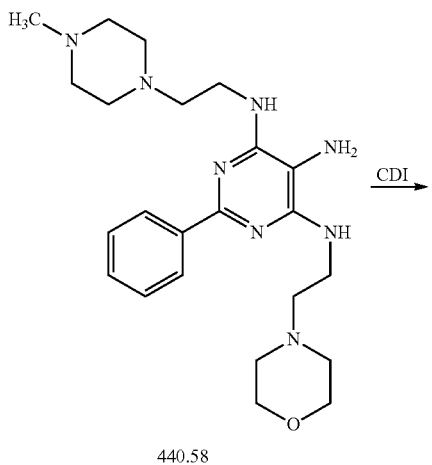

440.58

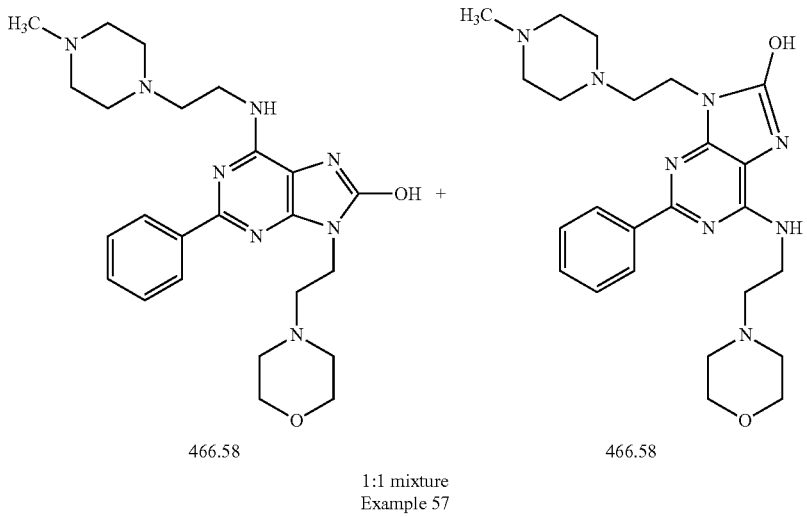

466.58          466.58

1:1 mixture
Example 57

The triaminopyrimidine from above was dissolved in methylene chloride (25 mL). To this solution was added carbonyldiimidazole (800 mg, 4.9×10⁻³ moles) and this solution was stirred at room temperature overnight. The solvents were removed under reduced pressure and the remaining material was purified by chromatography on silica using 12.5% methanol in methylene chloride as eluent. To elute the product, the eluent was changed to 1% methylamine and 25% methanol in methylene chloride. The fractions containing the product were pooled and evaporated under reduced pressure. The resulting oil quickly solidified upon standing. The solid was triturated in diethyl ether and was then isolated by filtration. This provided a mixture of isomers in a 1:1 ratio as determined by NMR. The yield was 730 mg. LC/MS: M+1=467.37

Example 58

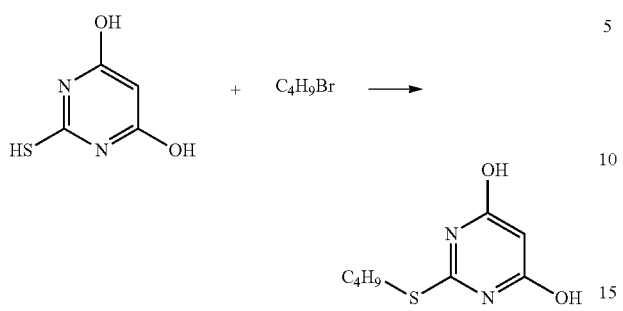

Thiobarbituric acid (14.4 gm, 0.10 moles) and n-butyl bromide (15.07 gm, 11.84 mL, 0.11 moles) were combined in methanol (300 mL), water (100 mL) and 30% sodium methoxide in methanol (19.81 gm, 0.11 moles). This mixture was stirred and heated to reflux, the heat was removed and stirring was continued as the temperature fell to room temperature. Solid sodium hydroxide (4.4 gm, 0.11 moles) was added and the resulting hazy solution was stirred at room temperature overnight. The slurry which had formed was heated to reflux to provide a clear solution. Hot water (400 mL) was added followed by acetic acid (15 mL). Upon cooling to room temperature a slurry had formed. The solid was isolated by filtration and was washed with water before being dried to provide 14.5 gm (72%) of the product as a white solid.

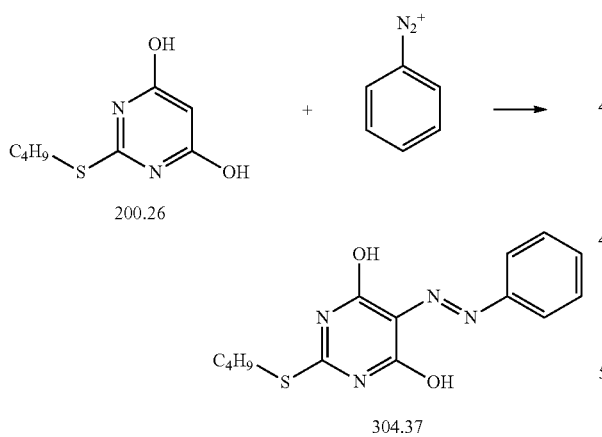

Solution 1:
Aniline (6.56 gm, 0.07 moles) was dissolved in water (200 mL) and Ice (100 gm) containing concentrated hydrochloric acid (14 mL). This solution was stirred as a solution of sodium nitrite (4.9 gm, 0.07 moles) dissolved in water (50 mL) was dripped in. Once the addition was complete the diazonium solution was kept on ice as solution 2 was prepared.
Solution 2:
Sodium hydroxide (16.9 gm, 0.42 moles) and 2-butylthio-4,6-dihydroxypyrimidine (14.1 gm, 0.07 moles) were dissolved in water (200 mL) and once dissolution was complete, ice (100 gm) was added.

Solution 1 was slowly poured into solution 2 at ice temperature with stirring. The resulting bright orange solution was stirred and the sodium salt of the azo compound soon crystallized forming a thick slurry. After 30 minutes, the thick slurry was acidified with concentrated hydrochloric acid and after sitting for 30 minutes, the azo compound was isolated by filtration. The damp solid was washed with water and dried to provide the azopyrimidine as a yellow solid in a yield of 19.3 gm (90.6%).

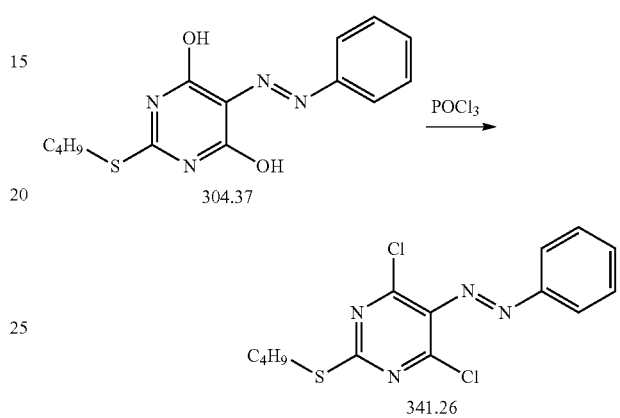

The dihydroxybutylthioazopyrimidine (18.6 gm, 0.061 moles) was powdered and mixed with phosphorous oxychloride (80 mL). This mixture was stirred as diisopropylethylamine (20 mL) was slowly added. The temperature rose to 60° C. The resulting orange solution was heated at reflux for 1 hour. Upon cooling, excess phosphorous oxychloride was removed under reduced pressure. The residual material was treated with ice and this was then extracted with methylene chloride (250 mL). The methylene chloride extracts were washed with water (200 mL) followed by 5% sodium bicarbonate (200 mL) before being dried over magnesium sulfate. After filtration, the solvent was removed under reduced pressure to give 20 gm of the product as an red oil.

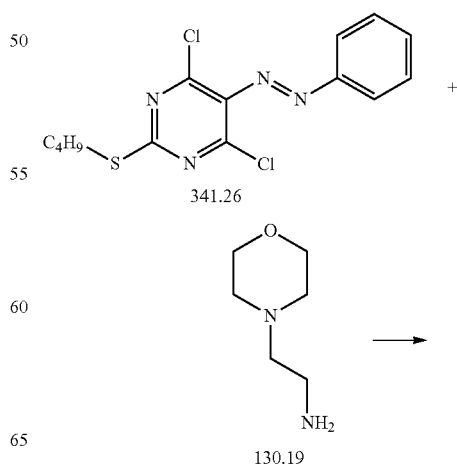

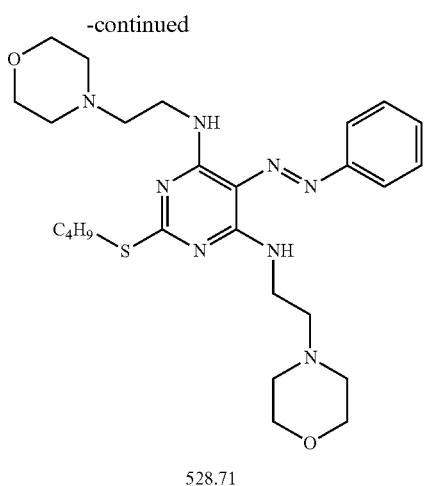

528.71

A mixture of 2-butylthio-4,6-dichloro-5-phenylazopyrimidine (6.82 gm, 2.0×10⁻² moles) and N-2-aminoethylmorpholine (10.4 gm, 8.0×10⁻² moles) in n-butanol (50 mL) was heated to boiling. After 2 hours at reflux the hot solution was diluted with 2-propanol (100 mL) and then cooled. Upon cooling, the product crystallized as a yellow solid. This was isolated by filtration, washed with 2-propanol and dried to provide the product in a yield of 6.8 gm, (64.3%).

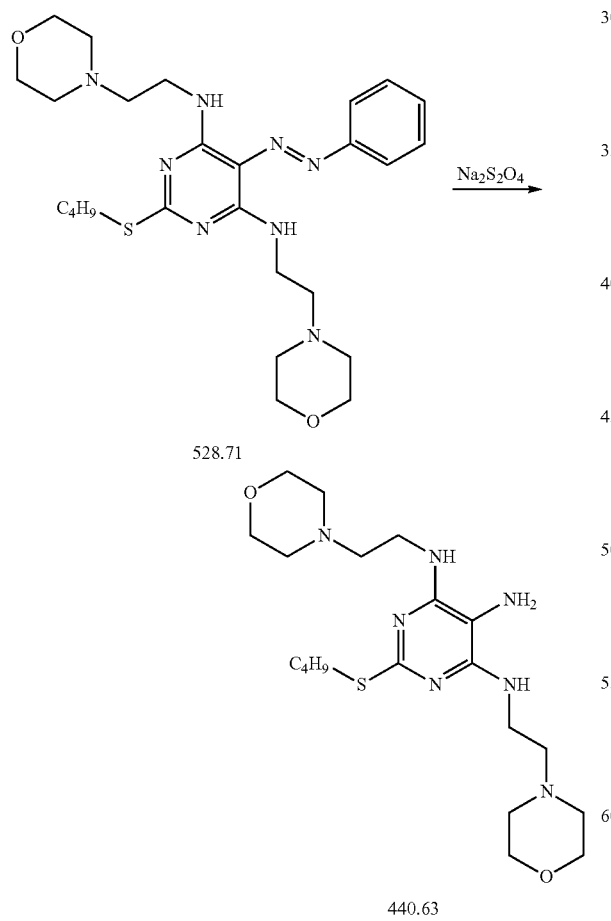

528.71

440.63

The azopyrimidine (6.8 gm, 1.29×10⁻² moles) was stirred in water (100 mL) containing acetic acid (4.0 mL) and concentrated hydrochloric acid (1.2 mL). This mixture was heated at 60° C. forming an orange solution. To this stirred solution was added sodium dithionite (14 gm) in 4 equal portions over 10 minutes. After the last addition, a pale yellow solution had formed. After stirring at 60° C. for an additional 30 minutes the solution was cooled and made basic by the addition of potassium carbonate. The oil which had separated was extracted into methylene chloride (200 mL) and the extracts were dried over magnesium sulfate. After filtration, the methylene chloride was evaporated under reduced pressure. The remaining material was used in the next step without purification.

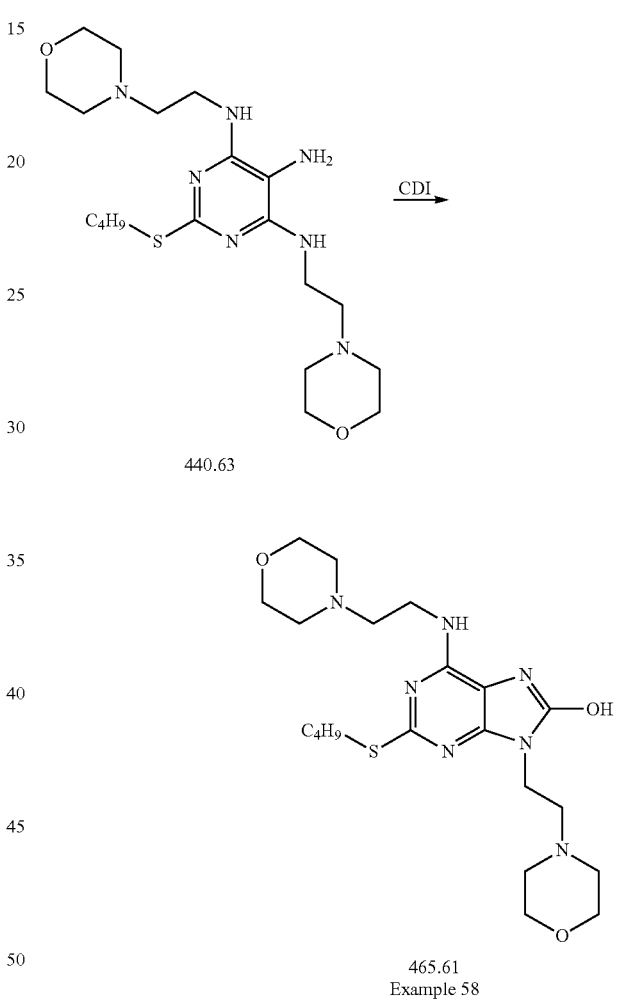

440.63

465.61
Example 58

The triaminopyrimidine from above was dissolved in methylene chloride (100 mL). To this solution was added carbonyldiimidazole (3.0 gm) and this solution was stirred at room temperature overnight. The solvents were removed under reduced pressure and the remaining material was dissolved in ethyl acetate (150 mL). The ethyl acetate solution was extracted with 5% hydrochloric acid (2×100 mL) and the combined extracts were washed with ethyl acetate (100 mL). The acidic aqueous extracts were made basic by the addition of potassium carbonate and the precipitated oil was extracted into methylene chloride (150 mL). After drying over magnesium sulfate the solution was filtered and the filtrates were evaporated under reduced pressure. The remaining material was purified by chromatography on silica using 10% methanol in methylene chloride as eluent. The fractions containing the product were pooled and evaporated under reduced pressure. The resulting oil quickly solidified upon standing to give the product as a white solid. The yield was 1.25 gm. LC/MS: M+1=466.4.

Example 59

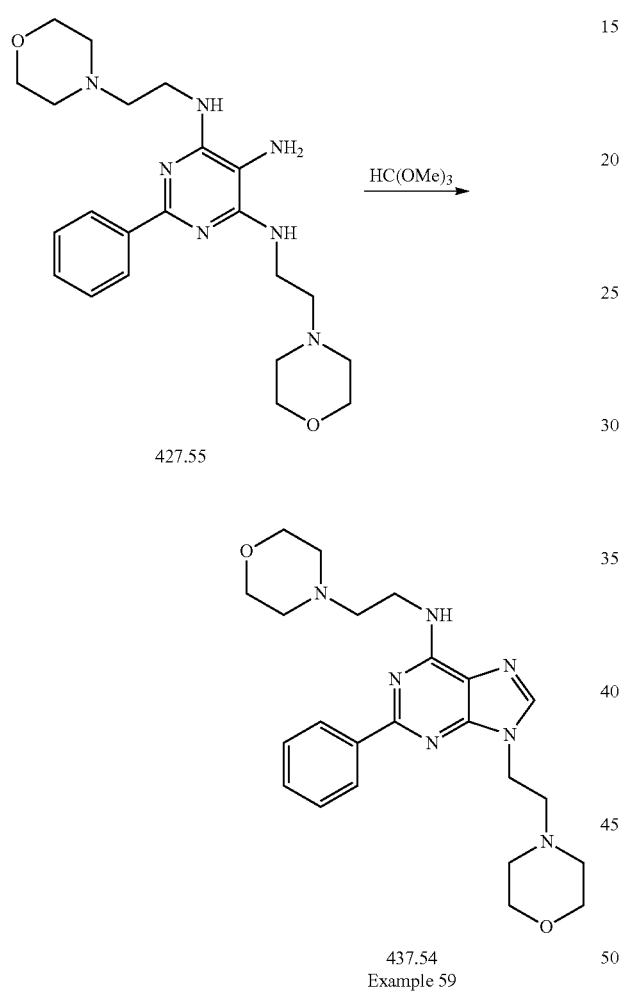

427.55

437.54
Example 59

The triaminopyrimidine from above was stirred in trimethylorthoformate (10 mL), and methanol (10 mL). To this solution was added concentrated hydrochloric acid (750 µL). Warming provided a clear pale yellow solution. This solution was stirred at room temperature overnight. The solvents were removed under reduced pressure and the remaining material was stirred with 10% potassium carbonate solution (50 mL) and methylene chloride (50 mL). The methylene chloride solution was dried over magnesium sulfate and the solution was filtered. The filtrates were evaporated under reduced pressure. The remaining material was purified by chromatography on silica using 10% methanol in methylene chloride as eluent. The fractions containing the product were pooled and evaporated under reduced pressure. The resulting oil was dissolved in diethyl ether causing the product to crystallize. The product was isolated by filtration, washed with diethyl ether and dried to give the product as a white solid. The yield was 200 mg. $^1$H NMR: 2.6 ppm, triplet, 8H, 2.7 ppm, triplet, 2H, 2.8 ppm, triplet, 2H, 3.7 ppm, triplet, 4H, 3.8 ppm, triplet, 4H, 4.0 ppm, multiplet, 2H, 4.4 ppm, triplet, 2H, 6.5 ppm, triplet, 1H, 7.4 ppm, multiplet, 3H, 7.9 ppm, singlet, 1H, 8.5 ppm, multiplet, 2H. LC/MS: M+1=438.4.

Example 60

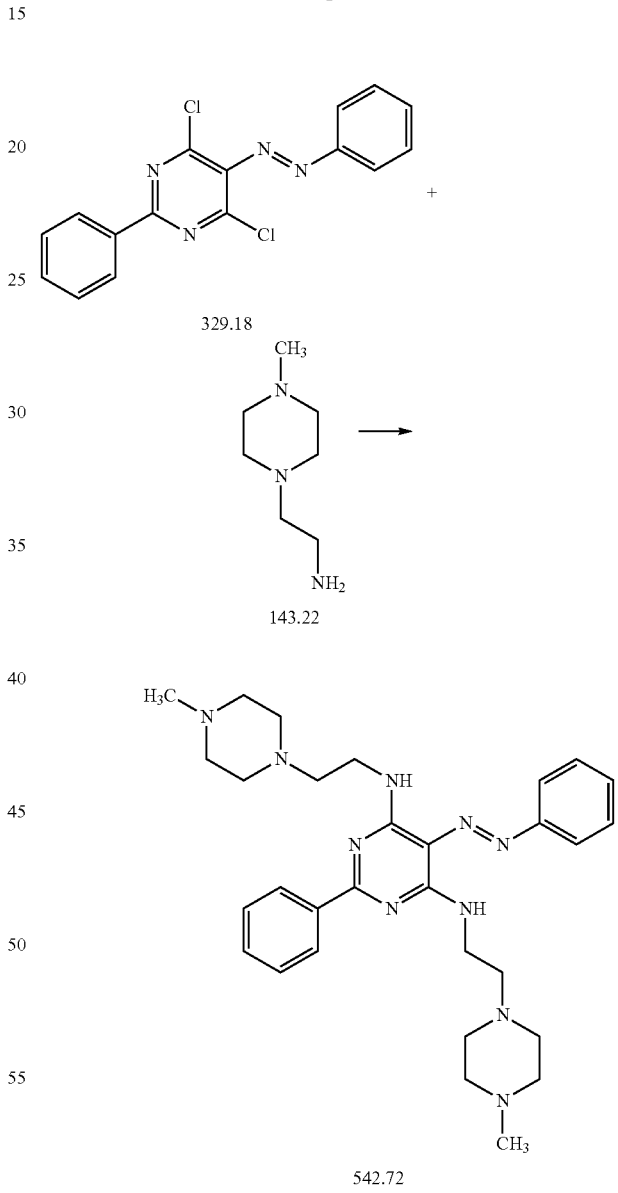

329.18

143.22

542.72

The dichloropyrimidine (3.29 gm, 0.01 moles) was dissolved in n-butanol (30 mL) and N-methyl-N'-(2-aminoethyl)piperazine (3.0 gm, $2.1 \times 10^{-2}$ moles) was added. This mixture was heated to 115° C. forming a dark orange solution. After 2 hours, TLC (silica, 25% methanol in methylene chloride)

showed some remaining starting material along with a single product. Diisopropylethylamine (02.58 gm, 0.02 moles) was added along with additional N-methyl-N'-(2-aminoethyl)piperazine (1.0 gm, $7.0 \times 10^{-3}$ moles) and this solution was heated at 115° C. for an additional 2 hours. After cooling the reaction was diluted with hexane (100 mL) and this solution was extracted with water (50 mL). The hexane solution was dried over magnesium sulfate, filtered and the solvents were removed under reduced pressure. The remaining orange solid was boiled in hexane (50 mL) and then cooled on ice. The solid was isolated by filtration, washed with hexane and dried. Yield was 3.0 gm, (55%).

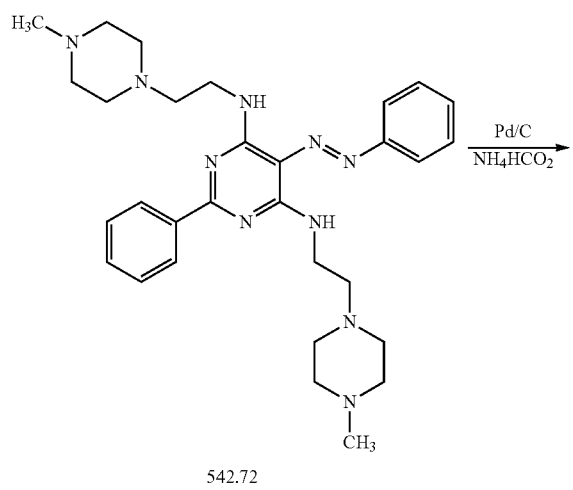

The phenylazopyrimidine (3.0 gm, $5.53 \times 10^{-3}$ moles) was stirred in methanol (30 mL) and THF (30 mL). To this was added ammonium formate (3.0 gm) dissolved in water (6 mL) along with 10% palladium on carbon (200 mg). After being heated at 55° C. for 15 minutes, TLC (silica, 25% methanol in methylene chloride) showed consumption of the azo compound. Water (10 mL) was added and stirring was continued for 5 minutes. After cooling, the catalyst was removed by filtration and the filtrates were made basic by the addition of potassium carbonate (4 gm). After stirring for 5 minutes the mixture was extracted with methylene chloride (200 mL). The solution was dried over magnesium sulfate. After filtration to remove the magnesium sulfate, the solvents were removed under reduced pressure. To the oily remainder was added 1:1 diethyl ether and hexane (100 mL). After stirring for 5 minutes the solvents were decanted and the triamine was dried under vacuum. This was used in the next step without further purification.

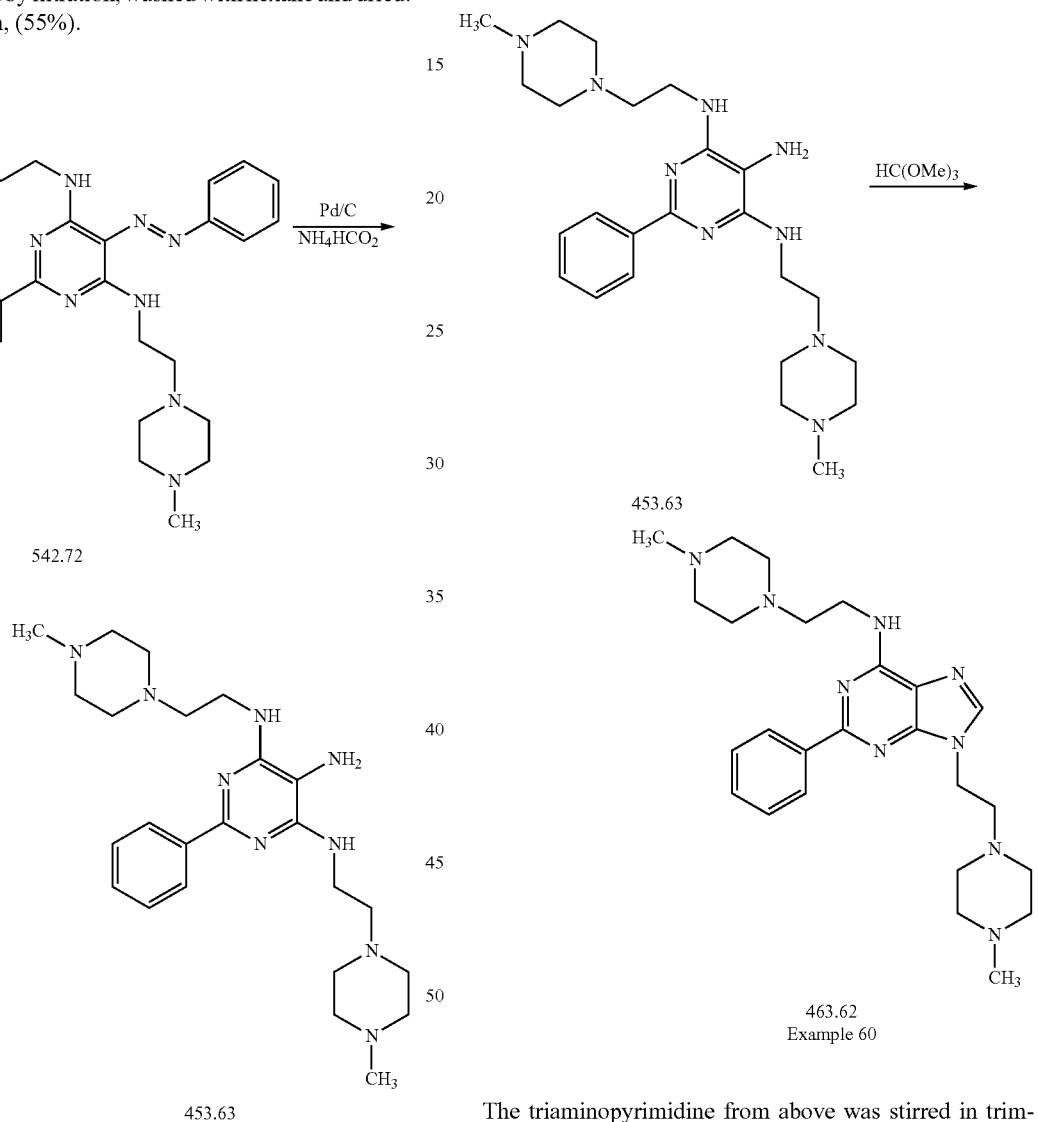

The triaminopyrimidine from above was stirred in trimethylorthoformate (30 mL), and methanol (30 mL). To this solution was added concentrated hydrochloric acid (3.0 mL). This solution was stirred at room temperature for 4 hours. The solvents were removed under reduced pressure and the remaining material was stirred with 5% potassium carbonate solution (200 mL) and methylene chloride (200 mL). The methylene chloride solution was dried over magnesium sulfate and the solution was filtered. The filtrates were evaporated under reduced pressure. The remaining material was dissolved in ethanol (100 mL) and sulfuric acid (1.08 gm, $1.1 \times 10^{-2}$ moles) dissolved in ethanol (20 mL) was added. The sulfate salt precipitated and was isolated by filtration. The salt was washed with ethanol and then washed with diethyl ether and dried to give the product as a solid. The yield was 2.7 gm. LC/MS: M+1=464.5.

Example 61

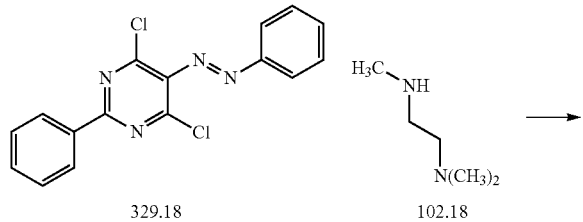

329.18   102.18

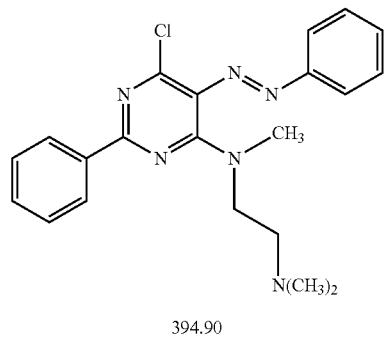

394.90

The dichloropyrimidine (3.29 gm, 0.01 moles) was dissolved in 2-propanol (30 mL) and N,N,N'trimethylethylenediamine (1.12 gm, 0.011 moles) was added. This slurry was heated at 60° C. which caused the formation of a clear dark orange solution. The heating was continued for 15 minutes. After cooling on ice a solid had separated. This was isolated by filtration and was washed with 2-propanol, followed by diethyl ether. After drying there was obtained 3.7 gm (86%) of the product as the orange hydrochloride salt.

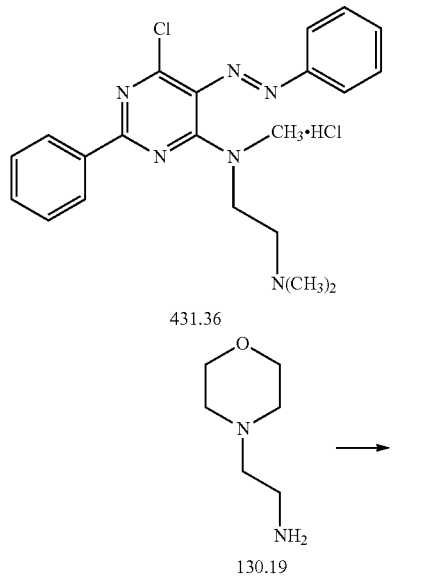

431.36

130.19

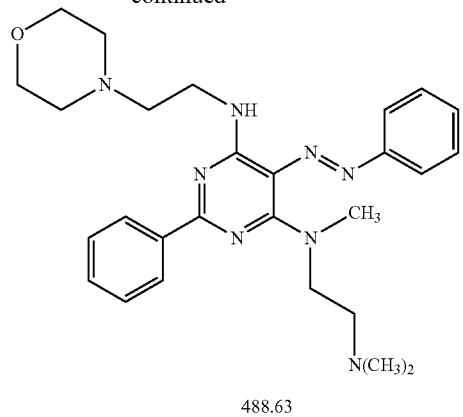

488.63

The monochloropyrimidine (3.7 gm, $8.58 \times 10^{-3}$ moles) and N-(2-aminoethyl)morpholine (3.35 gm, $2.57 \times 10^{-2}$ moles) were combined in n-butanol (40 mL) and heated at 115° C. A dark orange solution formed upon heating and after heating for 10 minutes, TLC (10% methanol in methylene chloride) showed clean conversion to a single compound (Rf=0.63). After cooling, the butanol was removed under reduced pressure. The remaining material was purified by chromatography on silica using 10% methanol in methylene chloride as eluent. The fractions containing the product were pooled and evaporated to give an oil that solidified upon standing. Yield was 3.5 gm of the diaminophenylazopyrimidine.

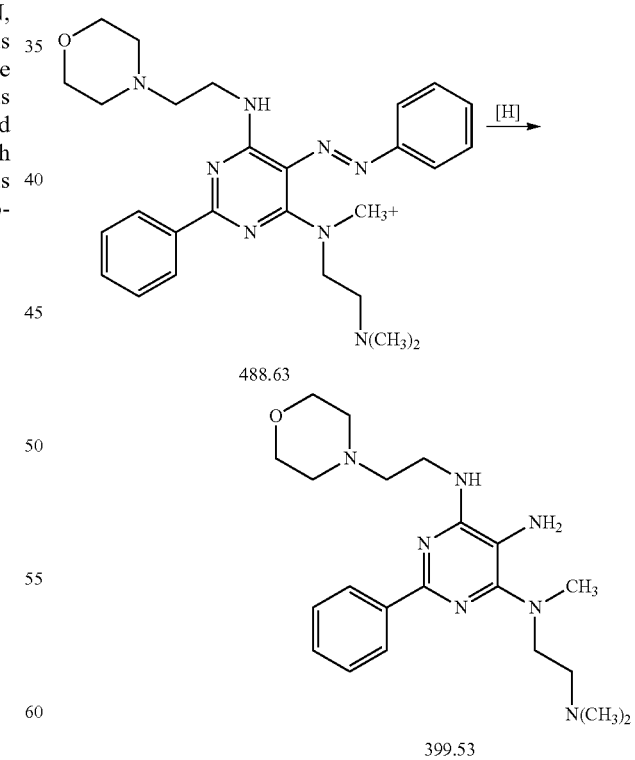

488.63

399.53

The phenylazopyrimidine (3.5 gm, $7.2 \times 10^{-3}$ moles) was stirred in methanol (50 mL) and THF (50 mL). To this was added ammonium formate (5.0 gm) dissolved in water (10 mL) along with 10% palladium on carbon (200 mg). After being heated at 60° C. for 60 minutes, TLC (silica, 25% methanol in methylene chloride) showed consumption of the azo compound. Water (20 mL) was added and stirring was continued for 5 minutes. After cooling, the catalyst was removed by filtration and the filtrates were evaporated under reduced pressure. The remaining aqueous material was made basic by the addition of potassium carbonate (5 gm). After stirring for 5 minutes the mixture was extracted with methylene chloride (200 mL). The solution was dried over magnesium sulfate. After filtration to remove the magnesium sulfate, the solvents were removed under reduced pressure. To the oily remainder was added hexane (100 mL). After stirring for 5 minutes the solvents were decanted and the triamine was dried under vacuum. This was used in the next step without further purification.

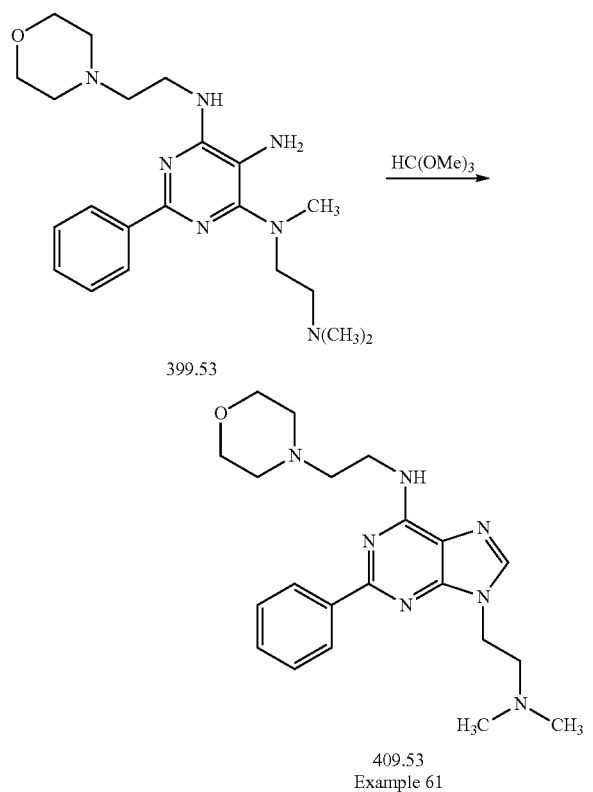

The triaminopyrimidine from above was stirred in trimethylorthoformate (30 mL), and methanol (30 mL). To this solution was added concentrated hydrochloric acid (3.5 mL). This solution was stirred at room temperature for 90 min. The solvents were removed under reduced pressure and the remaining material was stirred with 10% potassium carbonate solution (100 mL) and methylene chloride (150 mL). The methylene chloride solution was dried over magnesium sulfate and the solution was filtered. The filtrates were evaporated under reduced pressure. The remaining material was purified by chromatography on silica using 15% methanol in methylene chloride. The fractions containing the product were pooled and evaporated under reduced pressure. The remaining material (645 mg) was dissolved in ethanol (25 mL) and diethyl ether (25 mL). To this solution was added sulfuric acid (307 mg, $3.13 \times 10^{-3}$ moles) dissolved in ethanol (2 mL). The sulfate salt precipitated and was isolated by filtration. The salt was washed with diethyl ether and dried to give the product as a solid. The yield was 710 mg. LC/MS: M+1=410.5.

Example 62

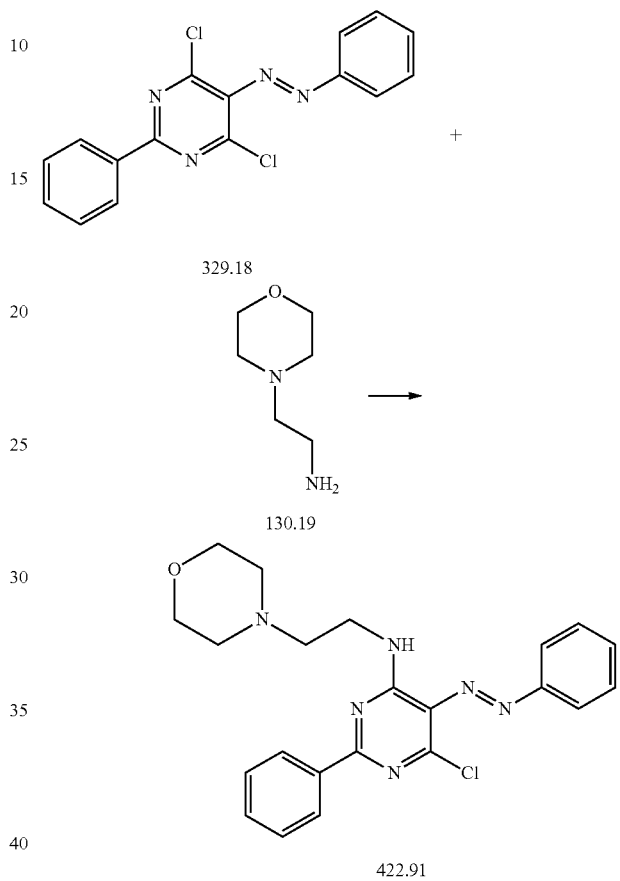

The dichloropyrimidine (3.29 gm, 0.01 moles) was stirred in 2-propanol with N-(2-aminoethyl)morpholine (1.43 gm, 0.011 moles) and diisopropylethylamine (1.29 gm, 0.01 moles). This was heated to reflux and n-butanol (15 mL) was added. After heating at reflux for 15 minutes, TLC (silica, 50% ethyl acetate in hexane) showed a single product had formed (Rf=0.53) After cooling, the solid product was isolated by filtration, washed with 2-propanol and dried. The yield was 3.9 gm (92.2%) of the product as an orange solid.

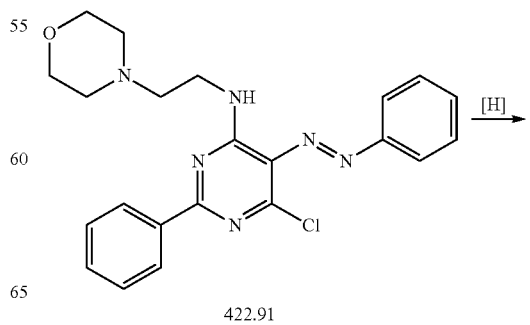

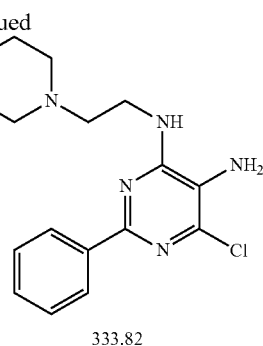

333.82

The phenylazopyrimidine (1.0 gm, $2.36 \times 10^{-3}$ moles) and tetrabutylammonium chloride (1.0 gm) were stirred in methanol (15 mL) and THF (35 mL). To this was added ammonium formate (1.0 gm) dissolved in water (2 mL) along with 10% palladium on carbon (250 mg). After being heated at 60° C. for 150 minutes, TLC (silica, 10% methanol in methylene chloride) showed consumption of the azo compound. Ethyl acetate (100 mL) and 5% potassium carbonate were added. The ethyl acetate solution was dried over magnesium sulfate. After filtration to remove the magnesium sulfate, the solvents were removed under reduced pressure. This was used in the next step without further purification.

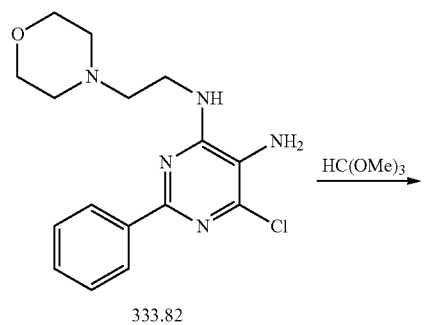

333.82

HC(OMe)₃ →

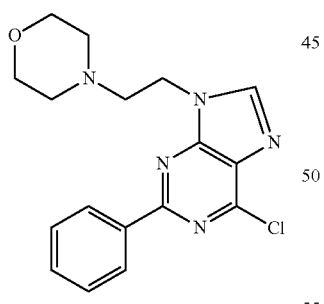

343.81

The crude diamine from above was stirred in trimethylorthoformate (30 mL), and methanol (30 mL). To this solution was added concentrated hydrochloric acid (3.0 mL). This solution was stirred at room temperature for overnight. The solvents were removed under reduced pressure and the remaining material was stirred with 10% potassium carbonate solution (100 mL) and methylene chloride (100 mL). The methylene chloride solution was dried over magnesium sulfate and the solution was filtered. The filtrates were evaporated under reduced pressure. The remaining material was purified by chromatography on silica using 10% methanol in methylene chloride. The fractions containing the product were pooled and evaporated under reduced pressure. The remaining material was used in the next step.

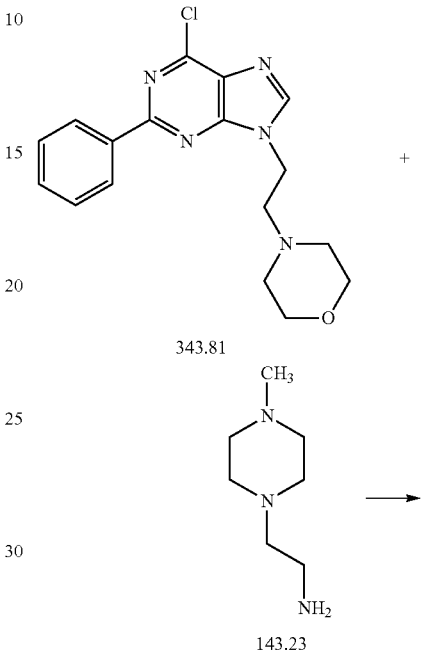

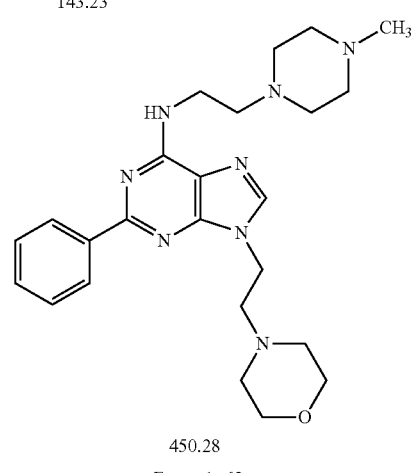

450.28
Example 62

The chloropurine from above was dissolved in n-butanol (15 mL) and N-methyl-N'-(2-aminoethyl)piperazine (2.0 gm) was added. This solution was heated at 100° C. for 1 hour. TLC (silica, 25% methanol in methylene chloride) showed formation of a major product at Rf=0.46. The butanol was removed under reduced pressure. The remaining material was purified by chromatography on silica using 20% methanol in methylene chloride. The fractions containing the product were pooled and evaporated under reduced pressure. The remaining material (144.5 mg) was dissolved in ethanol (4 mL) and diethyl ether (25 mL). To this solution was added sulfuric acid (62.9 mg, $6.42 \times 10^{-4}$ moles) dissolved in ethanol (1 mL). The sulfate salt precipitated and was isolated by filtration. The salt was washed with diethyl ether and dried to give the product as a solid. The yield was 165 mg. LC/MS: M+1=451.4.

Example 63

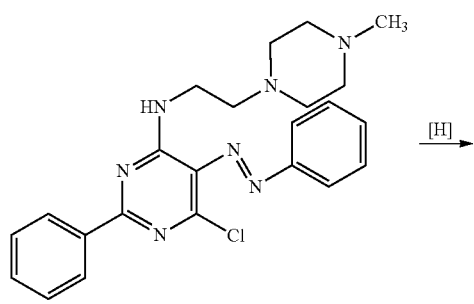

435.95

[H] →

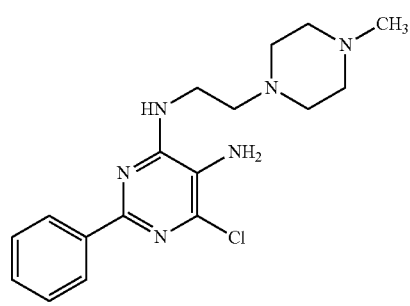

346.86

The phenylazopyrimidine (1.0 gm, 2.36×10⁻³ moles) and tetrabutylammonium chloride (1.0 gm) were stirred in methanol (15 mL) and THF (35 mL). To this was added ammonium formate (1.0 gm) dissolved in water (2 mL) along with 10% palladium on carbon (250 mg). After being heated at reflux for 5 minutes a colorless solution had formed. The solution was filtered and the filtrates were evaporated under reduced pressure. The remaining material was partitioned between water (100 mL) and methylene chloride (150 mL). The methylene chloride solution was dried over magnesium sulfate, filtered and evaporated under reduced pressure. The remainder was used without purification for the next step.

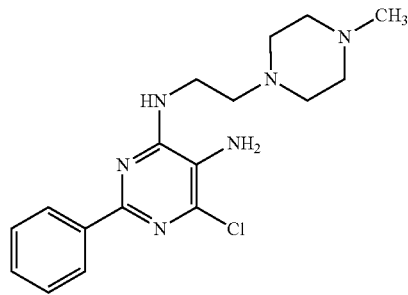

346.86

CDI →

-continued

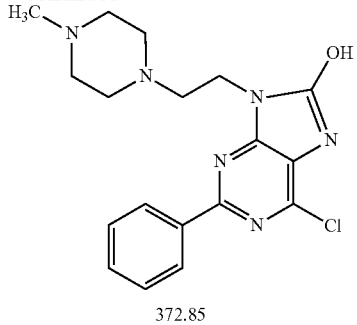

372.85

The chloropyrimidine from above was dissolved in methylene chloride (25 mL). To this solution was added carbonyldiimidazole (1.49 gm, 9.16×10⁻³ moles) and this solution was stirred at room temperature overnight. The solvents were removed under reduced pressure and the remaining material was purified by chromatography on silica using 15% methanol in methylene chloride as eluent. The fractions containing the product were pooled and evaporated under reduced pressure. The resulting Tan solid was isolated in a yield of 560 mg.

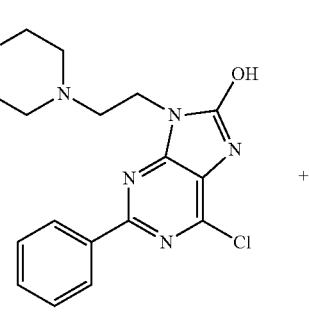

372.85

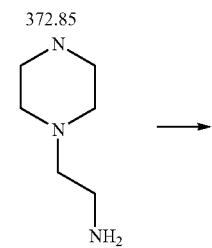

130.11

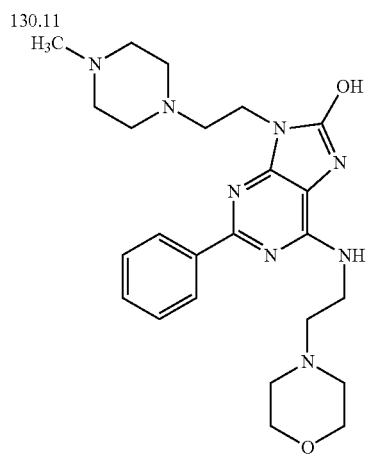

466.58
Example 63

The chloropurine from above (560 mg, $1.2 \times 10^{-3}$ moles) was dissolved in n-butanol (10 mL) and N-(2-aminoethyl) morpholine (312 mg, $2.4 \times 10^{-3}$ moles) was added. This solution was heated at reflux for 2 hours. TLC (silica, 25% methanol in methylene chloride) showed little conversion so the butanol was evaporated at 140° C. The remaining material was heated, neat, at 140° C. for 30 minutes. After cooling, the remaining brown oil was purified by chromatography on silica using 12.5% methanol in methylene chloride as eluent. To elute the product, the eluent was changed to 1% methylamine and 25% methanol in methylene chloride. The fractions containing the product were pooled and evaporated under reduced pressure to give 124 mg of product. This material (124 mg) was dissolved in methanol (10 mL) and to this solution was added sulfuric acid (52.3 mg, $5.33 \times 10^{-4}$ moles) dissolved in methanol (1 mL). The methanol was removed under reduced pressure and diethyl ether (30 mL) was added. The sulfate salt precipitated and was isolated by filtration. The salt was washed with diethyl ether and dried to give the product as a solid. The yield was 123 mg. LC/MS: M+1=467.5.

TLR9 Antagonist Assay

HEK-Blue™-hTLR9 cells were obtained from InvivoGen Inc. and used to determine test compound antagonism of human TLR9 (hTLR9) driven responses. HEK-Blue™-hTLR9 cells are designed for studying the stimulation of human TLR9 by monitoring the activation of NF-kB. As described by the manufacturer, "HEK-Blue™-hTLR9 cells were obtained by co-transfection of the hTLR9 gene and an optimized secreted embryonic alkaline phosphatase (SEAP) reporter gene into HEK293 cells. The SEAP reporter gene is placed under the control of the IFN-b minimal promoter fused to five NF-kB and AP-1 binding sites. Stimulation with a TLR9 ligand activates NF-kB and AP-1 which induces the production of SEAP. Levels of SEAP can be easily determined with QUANTI-Blue™ a detection medium that turns purple/blue in the presence of alkaline phosphatase".

TLR9 Antagonism Assay

Day 1:

A cell suspension of HEK-Blue™-hTLR9 cells at ~450,000 cells per ml in test medium which contained 5% (v/v) heat inactivated FBS was prepared. 180 ul of cell suspension (~80,000 cells) was added per well of a flat-bottom 96-well plate and place in an incubator at 37° C. for overnight.

Day 2

Test compounds were serially diluted in test medium, generally starting at 10 uM, and diluting by 3 fold in a 96 well master plate. 20 ul of diluted test compound was transferred using a 12 channel multi-channel pipet to the cell plate and incubated at 37° C. for 1 hour. Then 20 ul of an hTLR9 agonist (such as ODN 2006, 1 µM) was added to each well and the plate incubated at 37° C. overnight.

Day 3

Invivogen's QUANTI-Blue™ was prepared following the manufacturer's instructions. 180 ml of resuspended QUANTI-Blue™ was added per well of a flat bottom 96-well plate. 20 µl per well of induced HEK-Blue™-hTLR9 cells supernatant was then added to the plate and the plate was incubated at 37° C. for 1-3 h. SEAP levels were determined using a spectrophotometer at 620 nm.

Calculation of $IC_{50}$

The concentration dependent inhibition of hTLR9 dependent SEAP production was expressed as the concentration of compound which produced half the maximal level of SEAP induced by the hTLR agonist alone. Percent activity was calculated for each observation using the formula: % activity=((observed O.D.−background O.D.)/(agonist only O.D.−background O.D.))*100. The 50% inhibitory concentration ($IC_{50}$) was calculated by using a 4 parameter Hill plot sigmoidal curve fit where the inflection point of the sigmoidal curve is defined as the point of 50% activity. The results are summarized in Table 3.

TABLE 3

| hTLR9 antagonism | |
|---|---|
| Examples | $IC_{50}$ (nM) |
| Example 54 | 142 |
| Example 1 | 72 |
| Example 55 | 5200 |
| Example 56 | 8010 |
| Example 57 | 271 |
| Example 58 | 11150 |
| Example 59 | 7533 |
| Example 60 | 604 |
| Example 61 | 2735 |
| Example 62 | 3293 |
| Example 63 | 497 |

The Effects of Test Articles on Toll-Like Receptor (TLR) Knockdown Following a Single Intraperitoneal Dose to Male C57Bl/6 Mice.

Toll-Like Receptor (TLR) knockdown effect of test articles was evaluated in a C57Bl/6J mouse. Primary end points included a terminal blood collection for analysis of cytokine production in response to CpG-DNA TLR9 agonist injection. Male C57Bl/6J mice, at ~8 weeks of age from Jackson Laboratories were used. Test groups were 3 mice per treatment group and the groups were administered test article in a series of descending doses within the range of 400 µg to 10 µg. Test article treatment was dosed at T=0 hr by intraperitoneal injection. Agonist (CpG ODN 1668) treatment was dosed one hour later, T=1 hr by intraperitoneal injection. Necropsy was performed 3 hours post agonist treatment, T=4 hr. Blood samples were collected into serum separator tubes, allowed to clot at room temperature for at least 20 minutes, centrifuged at ambient temperature at 3000 g for 10 minutes, and the serum was extracted. ELISA was performed to determine murine IL-12 levels following manufacture's protocol (BioLegend Inc.). Serum IL-12 levels were calculated and plotted versus administered dose of antagonist and inhibitory dose at 50% ($ID_{50}$) was determined. The results are shown in Table 4.

TABLE 4

| In vivo TLR antagonism | |
|---|---|
| Examples | µg $ID_{50}$ |
| Example 1 | 243 |
| Example 57 | 348 |
| Example 60 | 174 |

The invention claimed is:

1. A compound of formula I or a pharmaceutically acceptable salt thereof,

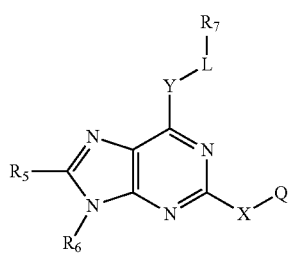

(I)

Wherein

X is an alkyl, alkylamino, cycloalkyl, aryl, or heterocycle;

Q is H, $(CH_2)_qNR_1R_2$, $NR_1(CH_2)_pNR_bR_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4;

$R_7$ is heteroaryl or $NR_3R_4$, wherein the heteroaryl is optionally substituted by $(C_1-C_4)$alkyl;

$R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle;

Y is $NR_{11}$, where $R_{11}$ is hydrogen, alkyl, cycloalkyl, alkenyl, or aryl group;

$R_{12}$ is alkyl, aryl, or heterocycle;

L is alkyl or alkenyl containing from 2 to 10 carbon atoms;

$R_5$ is hydrogen, halogen, cyano, nitro, $CF_3$, $OCF_3$, alkyl, cycloalkyl, alkenyl, aryl, heterocycle, $OR_a$, $SR_a$, $S(=O)R_a$, $S(=O)_2R_a$, $NR_bR_c$, $S(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, or $NR_bC(=O)R_a$;

$R_6$ is $(CH_2)_rC(=O)O(C_1-C_4)$alkyl, aryl, heterocycle, $(CH_2)_pNR_bR_c$, or alkylheterocycle, wherein r is 0-4 and p is 2-4;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

2. The compound of claim 1, wherein X is alkyl.

3. The compound of claim 1, wherein X is cycloalkyl.

4. The compound of claim 1, wherein X is heterocycle.

5. The compound of claim 1, wherein L is alkyl or alkenyl containing from 2 to 4 carbon atoms.

6. The compound of claim 1 having the structure of formula II:

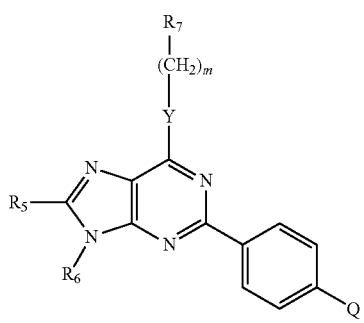

(II)

Wherein

Q is H, $(CH_2)_q NR_1R_2$, $NR_1(CH_2)_p NR_b R_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1$-$C_4)$alkyl, phenyl, benzyl, $C(\!=\!O)R_{12}$, $(CH_2)_p OR_a$, and $(CH_2)_p NR_b R_c$, in which p is 2-4;

$R_7$ is heteroaryl, wherein the heteroaryl is optionally substituted by $(C_1$-$C_4)$alkyl;

m is 2-6;

$R_{12}$ is alkyl, aryl, or heterocycle;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

7. The compound of claim 1 having the structure of formula III:

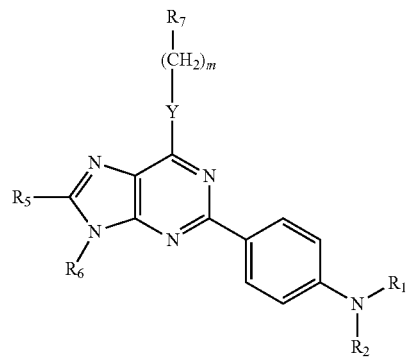

(III)

Wherein $R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1$-$C_4)$alkyl, phenyl, benzyl, $C(\!=\!O)R_{12}$, $(CH_2)_p OR_a$, and $(CH_2)_p NR_b R_c$, in which p is 2-4;

$R_7$ is heteroaryl, wherein the heteroaryl is optionally substituted by $(C_1$-$C_4)$alkyl;

m is 2-6;

$R_{12}$ is alkyl, aryl, or heterocycle;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

8. The compound of claim 1 having the structure of formula IV:

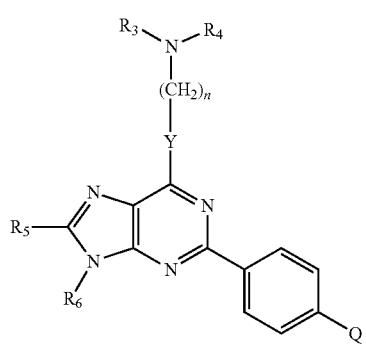

(IV)

Wherein

Q is H, $(CH_2)_q NR_1R_2$, $NR_1(CH_2)_p NR_b R_c$, $OR_1$, $SR_1$, or $CHR_1R_2$, in which q is 0 or 1 and p is 2-4;

$R_1$ and $R_2$ are each independently hydrogen, alkyl, alkenyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1$-$C_4)$alkyl, phenyl, benzyl, $C(\!=\!O)R_{12}$, $(CH_2)_p OR_a$, and $(CH_2)_p NR_b R_c$, in which p is 2-4;

n is 2-6;

$R_3$ and $R_4$ are each independently hydrogen, alkyl, cycloalkyl, alkenyl, aryl or alkylaryl, or $R_3$ and $R_4$ together with the nitrogen atom to which they are bonded form a heterocycle;

$R_{12}$ is alkyl, aryl, or heterocycle;

each occurrence of $R_a$ is independently hydrogen, alkyl, cycloalkyl, alkenyl, cycloalkenyl, alkynyl, heterocycle, or aryl; and each occurrence of $R_b$, and $R_c$ is independently hydrogen, alkyl, cycloalkyl, heterocycle, aryl, or said $R_b$ and $R_c$ together with the nitrogen atom to which they are bonded optionally form a heterocycle.

9. The compound of claim 1, wherein Q is H, $OR_1$, or $SR_1$.

10. The compound of claim 1, wherein $R_1$ and $R_2$ are each independently hydrogen, alkyl, cycloalkyl, alkylcycloalkyl, aryl, alkylaryl, heterocycle, alkylheterocycle, or $R_1$ and $R_2$ together with the nitrogen atom to which they are bonded form a heterocycle, which may be optionally substituted by from one to four groups which may be the same or different selected from $(C_1-C_4)$alkyl, phenyl, benzyl, $C(=O)R_{12}$, $(CH_2)_pOR_a$, and $(CH_2)_pNR_bR_c$, in which p is 2-4.

11. The compound of claim 1, wherein $NR_1R_2$, $NR_3R_4$, and $NR_bR_c$ are each independently a heterocycle selected from

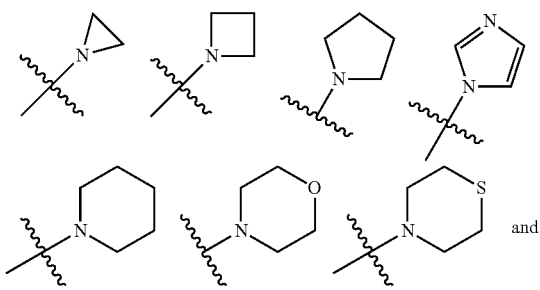

and in which $R_d$ is H, Me, Et, n-Pr, i-Pr, n-Bu, i-Bu, t-Bu, $CH_2CMe_3$, Ph, $CH_2Ph$, $C(=O)R_{12}$, $(CH_2)_pOR_a$, and $(CH_2)_pNR_{b'}R_{c'}$, wherein $R_{12}$ is alkyl, phenyl, or heterocycle; $R_{a'}$, $R_{b'}$ and $R_{c'}$ are each independently hydrogen, or $(C_1-C_4)$ alkyl, or $R_{b'}$ and $R_{e'}$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl; and p is 2-4.

12. The compound of claim 1, wherein $R_5$ is hydrogen, halogen, $(C_1-C_4)$alkyl, hydroxy, $(C_1-C_4)$alkoxy, $SR_a$, $S(=O)R_a$, $S(=O)_2R_a$, $S(=O)_2NR_bR_c$, in which $R_a$, $R_b$ and $R_c$ are each independently hydrogen or $(C_1-C_4)$alkyl.

13. The compound of claim 1, wherein $R_6$ is

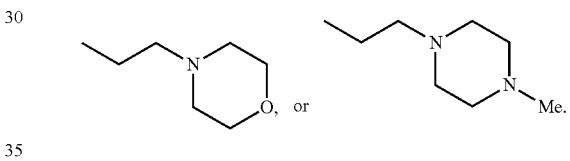

14. A compound of claim 1 selected from Tables 1-2 and Examples 15 and 55-63 shown below:

TABLE 1

| | | | wherein $R_7 = NR_3R_4$ | | | | | |
|---|---|---|---|---|---|---|---|---|
| Example No. | X | Q | Y | L | $R_3$ | $R_4$ | $R_5$ | $R_6$ |
| 15 | m-tolyl | N-methylpiperazine-CH3 | NH | —(CH$_2$)$_2$— | morpholine ($NR_3R_4$) | | H | pyridyl |

TABLE 2

| Example No. | X—Q | Y | L | $R_3$ | $R_4$ | $R_5$ | $R_6$ | $R_7$ |
|---|---|---|---|---|---|---|---|---|
| 55 | 4-tolyl-piperazine-CH3 | NH | —(CH$_2$)$_2$— | morpholine ($NR_3R_4$) | | H | —C(=O)OCH$_2$CH$_3$ | $NR_3R_4$ |

TABLE 2-continued

| Example No. | X—Q | Y | L | R$_3$ | R$_4$ | R$_5$ | R$_6$ | R$_7$ |
|---|---|---|---|---|---|---|---|---|
| 56 | tolyl | NH | —(CH$_2$)$_2$— | | NR$_3$R$_4$ = N-methylmorpholine | OH | N-propylmorpholine | NR$_3$R$_4$ |
| 57 | tolyl | NH | —(CH$_2$)$_2$— | | NR$_3$R$_4$ = N,N'-dimethylpiperazine | OH | N-propylmorpholine | NR$_3$R$_4$ |
| 58 | C$_4$H$_9$—S— | NH | —(CH$_2$)$_2$— | | NR$_3$R$_4$ = N-methylmorpholine | OH | N-propylmorpholine | NR$_3$R$_4$ |
| 59 | tolyl | NH | —(CH$_2$)$_2$— | | NR$_3$R$_4$ = N-methylmorpholine | H | N-propylmorpholine | NR$_3$R$_4$ |
| 60 | tolyl | NH | —(CH$_2$)$_2$— | | NR$_3$R$_4$ = N,N'-dimethylpiperazine | H | N-propyl-N'-methylpiperazine | NR$_3$R$_4$ |
| 61 | tolyl | NH | —(CH$_2$)$_2$— | | NR$_3$R$_4$ = N-methylmorpholine | H | N,N-dimethylaminopropyl | NR$_3$R$_4$ |
| 62 | tolyl | NH | —(CH$_2$)$_2$— | | NR$_3$R$_4$ = N,N'-dimethylpiperazine | H | N-propylmorpholine | NR$_3$R$_4$ |

TABLE 2-continued

| Example No. | X—Q | Y | L | R₃ | R₄ | R₅ | R₆ | R₇ |
|---|---|---|---|---|---|---|---|---|
| 63 | (methylphenyl) | NH | —(CH₂)₂— | NR₃R₄ = (N-methylpiperazinyl) | | Me | OH | (2-morpholinoethyl) NR₃R₄. |

15. A pharmaceutical composition comprising at least one compound according to claim 1 and a pharmaceutically-acceptable carrier or diluent.

16. A method of treating an autoimmune disease in a mammalian species having TLR-mediated immunostimulation, comprising administering to the mammalian species a therapeutically effective amount of at least one compound according to claim 1.

17. The method of claim 16, wherein the autoimmune disease is selected from cutaneous and systemic lupus erythematosus, insulin-dependent diabetes mellitus, rheumatoid arthritis, multiple sclerosis, atherosclerosis, psoriasis, psoriatic arthritis, inflammatory bowel disease, ankylosing spondylitis, autoimmune hemolytic anemia, Behget's syndrome, Goodpasture's syndrome, Graves' disease, Guillain-Barre syndrome, Hashimoto's thyroiditis, idiopathic thrombocytopenia, io myasthenia gravis, pernicious anemia, polyarteritis nodosa, polymyositis/dermatomyositis, primary biliary sclerosis, sarcoidosis, sclerosing cholangitis, Sjogren's syndrome, systemic sclerosis (scleroderma and CREST syndrome), Takayasu's arteritis, temporal arteritis, and Wegener's granulomatosis.

18. A method of inhibiting TLR-mediated immunostimulation in a mammalian species in need thereof, comprising administering to the mammalian species a therapeutically effective amount of at least one compound according to claim 1.

19. A method of inhibiting TLR-mediated immunostimulatory signaling, comprising contacting a cell expressing a TLR with an effective amount of at least one compound according to claim 1.

* * * * *